US011793854B2

(12) United States Patent
Wagner, Jr. et al.

(10) Patent No.: US 11,793,854 B2
(45) Date of Patent: Oct. 24, 2023

(54) METHODS FOR REDUCING SYMPTOMS OF MULTIPLE SCLEROSIS USING A SIX-AMINO ACID LONG PEPTIDE THAT INHIBITS CD40-CD150 INTERACTION

(71) Applicant: OP-T LLC, Denver, CO (US)

(72) Inventors: David Hal Wagner, Jr., Denver, CO (US); Martin Glenn Yussman, Denver, CO (US); Charles W. Henry, Denver, CO (US); Gisela M. Vaitaitis, Centennial, CO (US)

(73) Assignee: OP-T LLC, Aurora, CO (US)

( * ) Notice: Subject to any disclaimer, the term of this patent is extended or adjusted under 35 U.S.C. 154(b) by 0 days.

(21) Appl. No.: 16/827,523

(22) Filed: Mar. 23, 2020

(65) Prior Publication Data

US 2020/0297795 A1    Sep. 24, 2020

Related U.S. Application Data

(60) Provisional application No. 62/821,941, filed on Mar. 21, 2019.

(51) Int. Cl.
| | |
|---|---|
| *A61K 38/10* | (2006.01) |
| *A61K 38/00* | (2006.01) |
| *C07K 14/00* | (2006.01) |
| *A61K 38/08* | (2019.01) |
| *A61K 45/06* | (2006.01) |
| *A61P 25/28* | (2006.01) |
| *A61K 38/07* | (2006.01) |

(52) U.S. Cl.
CPC .............. *A61K 38/08* (2013.01); *A61K 38/07* (2013.01); *A61K 38/10* (2013.01); *A61K 45/06* (2013.01); *A61P 25/28* (2018.01)

(58) Field of Classification Search
CPC ............ C07K 2317/76; C07K 16/2827; C07K 16/2818; C07K 16/28; C07K 14/705; A61K 2039/505; A61K 38/00; A61K 38/1709; A61K 39/0008; A61K 38/08; A61P 25/00; A61P 37/02; A61P 21/00; A61P 25/02; A61P 21/04; G01N 33/6896
See application file for complete search history.

(56) References Cited

U.S. PATENT DOCUMENTS

| | | | |
|---|---|---|---|
| 6,264,951 B1 | 7/2001 | Armitage | |
| 6,319,671 B1 | 11/2001 | U'ren et al. | |
| 6,812,203 B1* | 11/2004 | Pype | A61P 37/06 514/20.6 |
| 7,087,573 B1 | 8/2006 | Lazarus | |
| 7,098,322 B2* | 8/2006 | Pype | A61P 43/00 536/23.1 |
| 7,189,518 B2 | 3/2007 | Schonbeck et al. | |
| 7,601,335 B2* | 10/2009 | McCutcheon | A61P 19/02 424/9.2 |
| 7,741,280 B2 | 6/2010 | Guichard et al. | |
| 8,476,008 B2 | 7/2013 | Nagalla et al. | |
| 9,409,987 B2* | 8/2016 | Toporik | A61K 39/0008 |
| 9,562,088 B2* | 2/2017 | Wagner | C07K 14/70575 |
| 10,882,911 B2* | 1/2021 | Park | C07K 16/2875 |
| 11,130,795 B2 | 9/2021 | Wagner | |
| 2004/0072750 A1 | 4/2004 | Phillips et al. | |
| 2005/0101769 A1* | 5/2005 | Pype | A61P 9/10 530/350 |
| 2006/0234316 A1 | 10/2006 | Wagner | |
| 2007/0041971 A1 | 2/2007 | Wagner | |
| 2007/0243259 A1 | 10/2007 | Sung et al. | |
| 2008/0050369 A1 | 2/2008 | Yellin et al. | |
| 2008/0058360 A1 | 3/2008 | Schonbeck et al. | |
| 2010/0062471 A1 | 3/2010 | Kantor et al. | |
| 2010/0172869 A1 | 7/2010 | Masuoka | |
| 2011/0177556 A1 | 7/2011 | Prussak et al. | |
| 2011/0229495 A1 | 9/2011 | Wagner | |
| 2013/0203719 A1 | 8/2013 | Kalergis et al. | |

(Continued)

FOREIGN PATENT DOCUMENTS

| | | |
|---|---|---|
| WO | WO-1999/011263 A1 | 3/1999 |
| WO | WO-2005/006949 A2 | 1/2005 |

(Continued)

OTHER PUBLICATIONS

Christensen et al.,PLos One; 2013; 8:e57820. doi:10.1371/journal.pone.0057820.*
Aarts et al.,Chapter 2, Front. Immunol. 2017; 8:1791; 24-45.*
Waid et al., J. Neuroimmunol. 2014; 270:75-85.doi:10.1016/j.jneuroim.2014.03.009.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Gerritse et al. PNAS, 1996; 93:2499-2504.*

(Continued)

*Primary Examiner* — Chang-Yu Wang
(74) *Attorney, Agent, or Firm* — Foley Hoag LLP; Brendan T. Jones; David E. Shore

(57) ABSTRACT

Methods and materials for treating and preventing autoimmune diseases, in particular, multiple sclerosis (MS) including small peptides are capable of interacting with CD40, thereby altering and/or modulating the ability of CD40 to interact with CD154, which apparently affects inflammation; and/or the use of such peptides in reducing the inflammatory response, and in particular, the autoimmune inflammatory response; and/or the use of such short peptides to prevent or reverse autoimmune disease, and particularly, multiple sclerosis, in individuals; and/or methods and materials for detecting T-cells that express CD40 (Th40 cells). Also provided are kits for reducing inflammation, treating autoimmune diseases, or detecting Th40 cells. Additionally, methods and apparatuses to administer the peptide are provided.

8 Claims, 23 Drawing Sheets

Specification includes a Sequence Listing.

(56) References Cited

U.S. PATENT DOCUMENTS

| | | | |
|---|---|---|---|
| 2013/0209463 A1* | 8/2013 | Rotman | A61P 9/14 424/134.1 |
| 2013/0236495 A1* | 9/2013 | Wagner | C07K 14/70575 424/278.1 |
| 2013/0306034 A1 | 11/2013 | Hamedovic et al. | |
| 2014/0044641 A1* | 2/2014 | Toporik | A61P 15/00 424/1.49 |
| 2014/0135684 A1 | 5/2014 | Kuo et al. | |
| 2014/0170141 A1* | 6/2014 | Toporik | A61K 45/06 424/134.1 |
| 2016/0296609 A1* | 10/2016 | Oh | C07K 16/28 |
| 2016/0347816 A1* | 12/2016 | Toporik | A61P 9/00 |
| 2016/0356771 A1 | 12/2016 | Smith et al. | |
| 2017/0108514 A1* | 4/2017 | Wagner | G01N 15/1459 |
| 2017/0232062 A1* | 8/2017 | Rotman | A61K 38/1709 424/134.1 |
| 2017/0306034 A1* | 10/2017 | Honczarenko | A61P 7/04 |
| 2017/0355747 A1* | 12/2017 | Wagner | C07K 14/70575 |
| 2018/0194829 A1* | 7/2018 | Toporik | A61P 43/00 |
| 2018/0194847 A1* | 7/2018 | Park | A61P 7/00 |
| 2019/0194290 A1 | 6/2019 | Wagner, Jr. et al. | |
| 2019/0231848 A1* | 8/2019 | Rotman | A61P 13/12 |
| 2019/0263888 A1* | 8/2019 | Wagner, Jr. | C07K 14/70575 |
| 2020/0072837 A1* | 3/2020 | Wagner, Jr. | G01N 33/56972 |
| 2020/0297795 A1 | 9/2020 | Wagner, Jr. et al. | |
| 2020/0326333 A1* | 10/2020 | Wagner, Jr. | G01N 33/56972 |
| 2021/0008162 A1* | 1/2021 | Wagner, Jr. | A61K 38/08 |
| 2021/0332104 A1 | 10/2021 | Wagner, Jr. et al. | |

FOREIGN PATENT DOCUMENTS

| | | |
|---|---|---|
| WO | WO-2007/090280 A1 | 8/2007 |
| WO | WO-2010/055510 A2 | 5/2010 |
| WO | WO-2012/154215 A1 | 11/2012 |
| WO | WO-2015/148389 A2 | 10/2015 |
| WO | WO2019/136307 * | 7/2019 |
| WO | WO-2019/136307 A1 | 7/2019 |
| WO | WO-2020/210726 A1 | 10/2020 |

OTHER PUBLICATIONS

Abdelhak et al. Front. Neurol.2017; doi:10.3389/fneur.2017.00234.*

Boon et al. J. Immunol. 2001; 167:2942-2949.*

Jensen et al. Eur. J. Neurol. 2001; 8:321-328.*

Laman et al. Multiple Sclerosis, 1998; 4:147-153.*

Laman et al. Eur. J. Immunol. 2002; 32:2218-2228.*

Fox, "Clinical features, pathogenesis, and treatment of Sjogren's syndrome," Current Opinion in Rheumatology, 8(5): 438-445 (1996).

Huseby et al., "A pathogenic role for myelin-specific CD8+ T cells in a model for multiple sclerosis," Journal of Experimental Medicine, 194(5): 669-679 (2001).

Lutterotti et al., "Antigen-specific tolerance by autologous myelin peptide-coupled cells: a phase 1 trial in multiple sclerosis," Science Translational Medicine, 5(188) 21 pages (2013).

Rivera et al., "Using Th40:Treg Ratio as a Predictor of Multiple Sclerosis and Other Autoimmune Diseases, University of Notre Dame, 2013, retrieved from www.ucdenver.edu/academics/colleges/medicalschool/centersM!ebbWaring/Documents/Summer%20Students0/o202013/Erika%20Rivera%20Poster%20Final.pdf, 1 page."

Thorsby et al., "Particular HLA-DQ molecules play a dominant role in determining susceptibility or resistance to Type 1 (insulin-dependent) diabetes mellitus," Diabetologia, 36(5): 371-377 (1993).

Vaitaitis et al., "Th40 cells (CD4+CD40+ Tcells) drive a more severe form of Experimental Autoimmune Encephalomyelitis than conventional CD4 T cells," PLoS One, 12: e0172037 (2017).

Wagner et al., "Expression of CD40 identifies a unique pathogenic T cell population in type 1 diabetes," PNAS, 99(6): 3782-3788 (2002).

"Society commits $19.4 Million for New MS Research Projects," National Multiple Sclerosis Society, 2013 retrieved from http://vitaminad.nositio.net/news/New_Research_Fall_2013.pdf, 28 pages.

Aarts et al., "Inhibition of CD4-TRAF6 interactions by the small molecule Inhibitor 6877002 reduces neuroinflammation," Journal of Neuroinflammation, 14(105): 105-118 (2017).

Allen et al., "Therapeutic peptidomimetic strategies for autoimmune diseases: costimulation blockade," The Journal of Peptide Research, 65(6): 591-604 (2005).

Anderson et al., "Multiple sclerosis, seizures, and antiepileptics: role of IL-18, IDO, and melatonin," European Journal of Neurology, 18(5): 680-685 (2011).

Angelini et al., "Analysis of HLA DP, DQ, and DR alleles in adult Italian rheumatoid arthritis patients," Human Immunology, 34(2): 135-141 (1992).

Arbour et al., "A new clinically relevant approach to expand myelin specific T cells," Journal of Immunological Methods, 310(1-2): 53-61 (2006).

Armitage et al., "CD40L: a multi-functional ligand," Seminars in Immunology, 5: 401-412 (1993).

Aruffo et al., "The CD40 Ligand, gp39, Is Defective in Activated T Cells from Patients with X-Linked Hyper-IgM Syndrome," Cell, 72: 291-300 (1993).

Attwood et al., "The Babel of Bioinformatics," Science, 290(5491): 471-473 (2000).

Bai et al., "Cerebrospinal Fluid and Blood Cytokines as Biomarkers for Multiple Sclerosis: A Systematic Review and Meta-Analysis of 226 Studies With 13,526 Multiple Sclerosis Patients," Front. Neurosci., 2019, 13: 1026.

Baker et al., "CD40 on NOD CD4 T cells contributes to their activation and pathogenicity," Journal of Autoimmunity, 31(4): 385-392 (2008).

Balasa et al., "CD40 Ligand-CD40 Interactions Are Necessary for the Initiation of Insulitis and Diabetes in Nonobese Diabetic Mice," The Journal of Immunology, 159: 4620-4627 (1997).

Barker et al., "Prediction of Autoantibody Positivity and Progression to Type 1 Diabetes: Diabetes Autoimmunity Study in the Young (DAISY)," Journal of Clinical Endocrinology & Metabolism, 89(8):3896-3902 (2004).

Becker et al., "CD40, an extracellular receptor for binding and uptake of Hsp70-peptide complexes," The Journal of Cell Biology, 158(7): 1277-1285 (2002).

Bee et al., "Exploring the Dynamic Range of the Kinetic Exclusion Assay in Characterizing Antigen-Antibody Interactions," Pios One, 7(4): e36261 (2012).

Benveniste et al., "Molecular regulation of CD40 gene expression in macrophages and microglia," Brain, Behavior, and Immunity, 18(1): 7-12 (2004).

Bojadzic et al., "CD40-targeting KGYY15 peptides do not efficiently block the CD40-CD40L interaction," Diabetologia, 62: 2158-2160 (2019).

Bonifacio, "Predicting Type 1 Diabetes Using Biomarkers," Diabetes Care, 38: 989-996 (2015).

Bourgeois et al., "A Role for CD40 Expression on CD8+ T cells in the Generation of CD8+ T Cell Memory," Science, 297: 2060-2063 (2002).

Bretscher, "The two-signal model of lympocyte activation twenty-one years later," Immunology Today, 13(2): 74-76 (1992).

Burge et al., "The Role of a Coronary Artery Calcium Scan in Type 1 Diabetes," Diabetes Technology & Therapeutics, 18(9): 594-603 (2016).

Buzzard et al., "Multiple Sclerosis: Basic and Clinical," Adv. Neurobiol., 2017, 15: 211-252.

Campean et al., "CD40-CD154 expression in calcified and non-calcified coronary lesions of patients with chronic renal failure," Atherosclerosis, 190(1): 156-166 (2007).

Carter et al., "CD40 engagement of CD4+CD40+ T cells in a neo-self antigen disease model ablates CTLA-4 expression and indirectly impacts tolerance," European Journal of Immunology, 42: 424-435 (2012).

Ceccarelli et al., "Microglia extracellular vesicles: focus on molecular composition and biological function," Biochem. Soc. Trans., 2021, 49(4): 1779-1790.

(56) References Cited

OTHER PUBLICATIONS

Chatzigeorgiou et al., "Blocking CD40-TRAF6 signaling is a therapeutic target in obesity-associated insulin resistance," PNAS, 111(7): 2686-2691 (2014).
Chen et al., "CD40/CD40L dyad in the inflammatory and immune responses in the central nervous system," Cell Mol. Immunol., 2006, 3(3): 163-169.
Cipollone et al., "Enhanced soluble CD40 ligand contributes to endothelial cell dysfunction in vitro and monocyte activation in patients with diabetes mellitus: effect of improved metabolic control," Diabetologia, 48: 1216-1224 (2005).
Cooper et al., "Cutting Edge: TCR Revision Occurs in Germinal Centers," The Journal of Immunology, 173: 6532-6536 (2004).
Davidson et al., "Co-Stimulatory Blockade in the Treatment of Murine Systemic Lupus Erythematosus," Ann. NY Acad. Sci, 987: 188-198 (2003).
De Ramon et al., "CD154-CD40 T-cell co-stimulation pathway is a key mechanism in kidney ischemia-reperfusion injury," Kidney International, 88: 538-549 (2015).
Deambrosis et al., "Inhibition of CD40-CD154 costimulatory pathway by a cyclic peptide targeting CD154," J. Mol. Med., 87: 181-197 (2009).
DeGraba et al., "Efficacy of an Interdisciplinary Intensive Outpatient Program in Treating Combat-Related Traumatic Brain Injury and Psychological Health Conditions," Front Neurol, 2020, 11: 580182.
Devaraj et al., "Increased Monocytic Activity and Biomarkers of Inflammation in Patients With Type 1 Diabetes," Diabetes, 55: 774-779 (2006).
Druzd et al., "Lymphocyte Circadian Clocks Control Lymph Node Trafficking and Adaptive Immune Responses," Immunity, 2017; 46: 120-32 [PubMed: 28087238].
Durie et al., "Prevention of Collagen-Induced Arthritis with an Antibody to gp39, the Ligand for CD40," Science, 261: 1328-1330 (1993).
Edwards et al., "Interleukin-6 is associated with acute concussion in military combat personnel," BMC Neurol., 2020, 20(1): 209.
Elliott et al., "Chronic white matter lesion activity predicts clinical progression in primary progressive multiple sclerosis," Brain a Journal of Neurology, 2019, 142(9): 2787-2799.
Ellmark et al., "Modulation or the CD40-CD40 ligand interaction using human anti-CD40 single-chain antibody fragments obtained from the n-CoDeR phage display library," Immunology, 106: 456-463 (2002).
Eshaghi et al., "Progression of regional grey matter atrophy in multiple sclerosis," Brain a Journal of Neurology, 2018, 141(6): 1665-1677.
Extended European Search Report for EP Application No. 18877124.0 dated Jul. 26, 2021.
Extended European Search Report for EP Application No. 19736089.4 dated Nov. 5, 2021.
Extended European Search Report for EP Application No. EP 11835055 dated Mar. 31, 2014.
Extended European Search Report for EP Application No. EP 18162234 dated Nov. 30, 2018.
Extended European Search Report for EP Application No. PCT/US2015/022033 dated Mar. 22, 2018.
Extended European Search Report for European Patent Application No. 15768543.9, dated Mar. 22, 2018, 6 pages.
Fan et al., "The emerging role of exosome-derived non-coding RNAs in cancer biology," Cancer Lett., 2018, 414: 107-115.
Fanslow et al., "Recombinant CD40 Ligand Exerts Potent Biologic Effect on T Cells," Journal of Immunology, 152: 4262-4269 (1994).
Fisniku et al., "Disability and T2 MRI lesions: a 20-year follow-up of patients with relapse onset of multiple sclerosis," Brain, 131(3): 808-817 (2008).
Fox, "Clinical features, pathogenesis, and treatment of Sjogren's syndrome," Current Opinion in Rheumatology, 8(5): 438-445 (1996) (Abstract Only).

Garlichs et al., "Upregulation of CD40 and CD40 ligand (CD154) in patients with moderate hypercholesterolemia," Circulation, 104: 2395-2400 (2001).
Girvin et al., "CD40/CD40L Interaction is Essential for the Induction of EAE in the Absence of CD28-Mediated Co-stimulation," Journal of Autoimmunity, 18(2): 83-94 (2002).
Giuliani et al., "Minocycline attenuates T cell and microglia activity to impair cytokine production in T cell-microglia interaction," Journal of Leukocyte Biology, 78: 135-143 (2005).
Goetzl et al., "Altered levels of plasma neuron-derived exosomes and their cargo proteins characterize acute and chronic mild traumatic brain injury," FASEB Jour., 2019, 33(4): 5082-5088.
Goetzl et al., "Traumatic brain injury increases plasma astrocyte-derived exosome levels of neurotoxic complement proteins," FASEB Jour., 2020, 34(2): 3359-3366.
Goodnow, "Pathways for self-tolerance and the treatment of autoimmune diseases," Lancet, 357: 2115-2121 (2001).
Goverman et al., "Transgenic mice that express a myelin basic protein-specific T cell receptor develop spontaneous autoimmunity," Cell, 72(4): 3018-3027 (1993).
Graber et al., "Interleukin-17 in transverse myelitis and multiple sclerosis," Journal of Neuroimmunology, 196(1-2): 124-132 (2008).
Grabstein, "The Regulation or T Cell-Dependent Antibody Formation in Vitro by CD40 Liqand and IL-2," The Journal of Immunology, 150(8): 3141-3147 (1993).
Grossman, "Avoiding Tolerance Against Prostatic Antigens With Subdominant Peptide Epitopes," Journal of Immunotherapy, 23(3): 237-241 (2001).
Guo et al., "CD40L-Dependant Pathway is Active at Various Stages of Rheumatoid Arthritis Disease Progression," The Journal of Immunology, 198: 4490-4501 (2017).
Hafler et al., "Risk alleles for multiple sclerosis identified by a genomewide study," New England Journal of Medicine, 357(9): 851-862 (2007).
Hamlett et al., "Neuronal exosomes reveal Alzheimer's disease biomarkers in Down syndrome," Alzheimers Dement., 2017, 13(5): 541-549.
Harrington et al., "Differential tolerance is induced in T cells recognizing distinct epitopes of myelin basic protein," Immunity, 8(5): 571-580 (1998).
Hart et al., "Preclinical assessment of therapeutic antibodies against human CD40 and human interleukin-12/23p40 in a nonhuman primate model of multiple sclerosis," Neurodegener. Dis., 2008, 5(1): 38-52.
Hartung et al., "Diagnosis of multiple sclerosis: revisions of the McDonald criteria 2017—continuity and change," Curr. Opin. Neurol., 2019, 32(3): 327-337.
Heath et al., "Monoclonal antibodies to murine CD40 define two distinct functional epitopes," Eur. J. Immunol., 24: 1828-1834 (1994).
Hemmer et al., "New concepts in the immunopathogenesis of multiple sclerosis," Nature Reviews Neuroscience, 3(4): 291-301 (2002).
Hernandez et al., "CD40-CD40 Ligand Interaction between Dendritic Cells and CDS+ T Celis Is Needed to Stimulate Maximal T Cell Responses in the Absence of CD4+ T Cell Help," The Journal of Immunology, 178: 2844-2852 (2007).
Hoffjan et al., "The genetics of multiple sclerosis: an update 2010," Molecular and Cellular Probes, 24(5): 237-243 (2010).
Homann et al., "CD40L Blockade Prevents Autoimmune Diabetes by Induction of Bitypic NK/DC Reaulatorv Geils," Immunity, 16: 403-415 (2002).
Howard et al., "Immunotherapy Targeting the CD40/CD154 Costimulatory Pathway for Treatment of Autoimmune Disease," Autoimmunity, 37(5): 411-418 (2004).
Huseby et al., "A pathogenic role for myelin-specific CD8+ T cells in a model for multiple sclerosis," Journal of Experimental Medicine, 194(5): 669-676 (2001).
Ichikawa et al., "Increased Fas antigen on T cells in multiple sclerosis," Journal of Neuroimmunology, 71(1-2): 125-129 (1996).

(56) References Cited

OTHER PUBLICATIONS

Iezzi et al., "CD40-CD40L cross-talk integrates strong antigenic signals and microbial stimuli to induce development of IL-17-producing CD4+ T cells," Proc Natl Acad Sci USA, 106: 876-881 (2009).
Ilonen et al., "Abnormalities within CD4 and CD8 T lymphocyte subsets in type 1 (insulin-dependent) diabetes," Clin. exp. Immunol., 85(2): 278-281 (1991).
International Preliminary Report on Patentability for International (PCT) Patent Application No. PCT/US11/56860 dated May 2, 2013, 8 pages.
International Preliminary Report on Patentability for International (PCT) Patent Application No. PCT/US2015/022033 dated Oct. 6, 2016, 17 pages.
International Preliminary Report on Patentability for International Application No. PCT/US2015/022033 dated Jul. 24, 2015.
International Search Report and Written Opinion for International (PCT) Patent Application No. PCT/US11/56860 dated May 4, 2012, 11 pages.
International Search Report and Written Opinion for International (PCT) Patent Application No. PCT/US2015/022033 dated Jul. 24, 2015, 20 pages.
International Search Report and Written Opinion for International Application No. PCT/US2019/012425 dated May 7, 2019.
International Search Report and Written Opinion for International Application No. PCT/US2020/027804 dated Jun. 22, 2020.
Kalatha et al., "Glial and neuroaxonal biomarkers in a multiple sclerosis (MS) cohort," Hell. J. Nucl .Med., 2019, 22 Suppl 2: 113-121.
Karpusas et al., "2 .ANG. crystal structure of an extracellular fragment of human CD40 ligand," Structure, 3,(10): 1031-1039 (1995).
Kennedy et al., "Acute Exercise Induces GLUT4 Translocation in Skeletal Muscle of Normal Human Subjects and Subjects With Type 2 Diabetes," Diabetes, 48: 1-6 (1999).
Kent et al., "Expanded T cells from pancreatic lymph nodes of type 1 diabetic subjects recognize an insulin epitope," Nature, 435(7039): 224-228 (2005).
Khambhati et al., "Immunotherapy for the prevention of atherosclerotic cardiovascular disease: Promise and possibilities," Atherosclerosis 276: 1-9 (2018).
Khan et al., "Differential peptide binding to CD40 evokes counteractive responses," Human Immunology, 73: 465-469 (2012).
King et al., "The Use of Animal Models in Diabetes Research," British Journal of Pharmacology, 166: 877-894 (2012).
Kitagawa et al., "Identification of three novel peptides that inhibit CD40-CD154 interaction," Mod. Rheumatol, 15: 423-426 (2005).
Kobata et al., "Role of costimulatory molecules in autoimmunity," Reviews in Immunogenetics, 2: 74-80 (2000).
Kuo et al., "IL-17 and CD40 ligand synergistically stimulate the chronicity of diabetic nephropathy," Nephrol Dial Transplant, 33: 248-256 (2018).
Kutzelnigg et al., "Cortical demyelination and diffuse white matter injury in multiple sclerosis," Brain a Journal of Neurology, 2005, 128(Pt 11): 2705-2712.
Laemmli ., "Cleavage of Structural Proteins during the Assembly of the Head of Bacteriophage T4," Nature, 227: 680-685 (1970).
Lederman et al., "Identification of a Novel Surface Protein on Activated CD4+ T Cells That Induces Contact-dependant B Cell Differentiation (Help)," J. Exp. Med., 175: 1091-1101 (1992).
Lederman et al., "Molecular Interactions Mediating T-B Lymphocyte Collaboration in Human Lymphoid Follicles: Roles of T Cell-B Cell-Activating Molecule (5c8 Antigen) and CD40 in Contact-Dependent Help," The Journal of Immunology, 149(12): 3817-3826 (1992).
Ledreux et al., "Assessment of Long-Term Effects of Sports-Related Concussions: Biological Mechanisms and Exosomal Biomarkers," Front. Neurosci. 2020, 14: 761.

Ledreux et al., "Small Neuron-Derived Extracellular Vesicles from Individuals with Down Syndrome Propagate Tau Pathology in the Wildtype Mouse Brain," J. Clin. Med., 2021, 10(17): 3931.
Lee et al., "Mouse models of atherosclerosis: a historical perspective and recent advances," Lipids in Health and Disease, 16: 1-11 (2017).
Liu et al., "CD127 expression inversely correlates with FoxP3 and suppressive function of human CD4+T reg cells," Journal of Experimental Medicine, 203(7): 1701-1711 (2006).
Liu et al., "NG2 glia are required for maintaining microglia homeostatic state," Glia, 2020, 68(2): 345-355.
Liu et al., "Targeted exosome-mediated delivery of opioid receptor Mu siRNA for the treatment of morphine relapse," Sci. Rep., 2015, 5: 17543.
Lovett-Racke et al., "Decreased dependence of myelin basic protein-reactive T cells on CD28-mediated costimulation in multiple sclerosis patients," Journal of Clincial Investigation, 101(4): 725-730 (1998).
Lucchinetti et al., "Inflammatory Cortical Demyelination in Early Multiple Sclerosis," New England Journal of Medicine, 365(23): 2188-2197 (2011).
Lutgens et al., "Long-term reversal of hypercholesterolemia in low density lipoprotein receptor (LDLR)-deficient mice by adenovirus-mediated LDLR gene transfer combined with CD154 blockade," Nature Medicine, 5: 1313-1316 (1999).
Lutterotti et al., "Antigen-specific tolerance by autologous myelin peptide-coupled cells: a phase 1 trial in multiple sclerosis," Science Translational Medicine, 5(188) 20 pages (2013).
Macaron et al., "Diagnosis and Management of Progressive Multiple Sclerosis," Biomedicines, 2019, 7(56): 23 pages.
Mackey et al., "Calcifications, arterial stiffness, and atherosclerosis," Atherosclerosis, Large Arteries and Cardiovascular Risk. Adv Cardiol., 44: 234-244 (2008).
Maggi et al., "Chronic White Matter Inflammation and Serum Neurofilament Levels in Multiple Sclerosis," Neurology 2021, 97(6): e543-e553.
Marsh, "Nomenclature for factors of the HLA system, updated Jan. 2012," Human Immunology, 73: 593-596 (2012).
Mayo Clinic Diabetes, mayoclinic.org/diseases-conditions/diabetes/symptoms-causes/syc-2037 1444?; pp. 1-7; mayoclinic.org/diseases-conditions/diabetes/diagnosis-treatment/drc-20371451?p=1; pp. 1-1 1, downloaded Feb. 20, 2012. (Year: 2012).
Mayo Clinic: Arteriosclerosis / Athersclerosis, mayoclinic.org/diseases-conditions/arteriosclerosis atherosclerosis/symptoms-causes /syc-20350569?, pp. 1-4; mayoclinic.org/diseases-conditions/arteriosclerosis-atherosclerosis/diagnosis-treatment/drc-20350575 ?p=1; pp. 1-7; downloaded Feb. 10, 2021. (Year: 2021).
McMahon et al., "Epitope spreading initiates in the CNS in two mouse models of multiple sclerosis," Nature Medicine, 11(3): 335-339 (2005).
Mcwhirter et al., "Crystallographic analysis of CD40 recognition and signaling by human TRAF2," Proc. Natl. Acad. Sci. USA, 96: 8408-8413 (1999).
Miller et al., "Antigen presentation in the CNS by myeloid dendritic cells drives progression of relapsing experimental autoimmune encephalomyelitis," Annals of the New York Academy of Sciences, 1103: 179-191 (2007).
Miller et al., "Clinically isolated syndromes," Lancet Neurology, 11(2): 157-169 (2012).
Miller et al., "The role of magnetic resonance techniques in understanding and managing multiple sclerosis," Brain, 121: 3-24 (1998).
Miller et al., "Virus-induced autoimmunity: epitope spreading to myelin autoepitopes in Theiler's virus infection of the central nervous system," Advances in Virus Research, 56: 199-217 (2001).
Munroe et al., "Pro-Inflammatory—Adaptive Cytokines and Shed Tumor Necrosis Factor Receptors are Elevated Preceding Systemic Lupus Erythematosus Disease Flare," Arthritis Rheumatol., 66(7): 1888-1899 (2014).
Najafian et al., "T cell costimulatory pathways: blockade for autoimmunity," Expert Opin. Biol. Ther., 2003, 3(2): 227-236.
Nguyen et al., "CD+CD40+ T cell levels predict risk of developing type I diabetes pre-diabetics," J Invest Med, Abstract, 62(1): 151-152 (2014).

(56) References Cited

OTHER PUBLICATIONS

Notice of Allowance and Fees Due for U.S. Appl. No. 13/880,387 dated Sep. 21, 2016.
Nourelden et al., "Safety and Efficacy of Teplizumab for Treatment of Type One Diabetes Mellitus: A Systematic Review and Meta-Analysis," Endocr. Metab. Immune Disord Drug Targets, 10: Abstract Only (2020).
Nyakeriga et al., "TCR-induced T cell activation leads to simultaneous phosphorylation at Y505 and Y394 of p56(lck) residues," Cytometry A, 81(9): 797-805 (2012).
O'Connor et al., "Antibodies from inflamed central nervous system tissue recognize myelin oligodendrocyte glycoprotein," Journal of Immunology, 175(3): 1974-1982 (2005).
Ontaneda., "Progressive Multiple Sclerosis," *Continuum (Minneap Minn)*, 2019, 25(3): 736-752.
Peng et al., "Microglia-Derived Exosomes Improve Spinal Cord Functional Recovery after Injury via Inhibiting Oxidative Stress and Promoting the Survival and Function of Endothelia Cells," *Oxid. Med. Cell Longev.*, 2021, 2021: 1695087.
Poggi et al., "The inflammatory receptor CD40 is expressed on human adipocytes: contribution to crosstalk between lymphocytes and adipocytes," Diabetologia, 52: 1152-1163 (2009).
Polman et al., "Diagnostic criteria for multiple sclerosis: 2010 revisions to the McDonald criteria," Annals of Neurology, 69(2): 292-302 (2011).
Polman et al., "Drug treatment of multiple sclerosis," Medicine Cabinent, 173: 398-402 (2000).
Polman et al., "Multiple sclerosis diagnostic criteria: three years later," Multiple Sclerosis Journal, 11(1): 5-12 (2005).
Pullen et al., "CD40 Signaling through Tumor Necrosis Factor Receptor-associated Factors (TRAFs)," The Journal of Biological Chemistry, 274(20): 14246-14254 (1999).
Pulliam et al., "Plasma neuronal exosomes serve as biomarkers of cognitive impairment in HIV infection and Alzheimer's disease," *J. Neurovirol.*, 2019, 25(5): 702-709.
Quezada et al., "Distinct Mechanisms of Action of Anti-CD154 in Early Versus Late Treatment of Murine Lupus Nephritis," Arthritis & Rheumatism, 48(9): 2541-2554 (2003).
Ramsdell et al., "CD40 Ligand Acts As a Costimulatory Signal for Neonatal Thymic Gamma Delta T Cells," The Journal of Immunology, 152: 2190-2197 (1994).
Resetkova et al., "Antibody to gp39, the Ligand for CD40 Significantly Inhibits the Humoral Response from Graves' Thyroid Tissues Xenografted into Severe Combined Immunodeficient (SCID) Mice," Thyroid, 6(4): 267-273 (1996).
Richards et al., "A peptide containing a novel FPGN CD40-binding sequence enhances adenoviral infection of murine and human dendritic cells," Eur. J. Biochem., 270: 2287-2294 (2003).
Rivera et al., "Using Th40:Treg Ratio as a Predictor of Multiple Sclerosis and Other Autoimmune Diseases, University of Notre Dame, 2013, retrieved from http:/iwww.ucdenver.edu/academics/ colleges/medicalschool/centersM!ebbWaring/Documents/Summer% 20Students0/o202013/Erika%20Rivera%20Poster%20Final.pdf, 1 page."
Rolink et al., "The SCID but Not the RAG-2 Gene Product Is Required for S?-S? Heavy Chain Class Switching," Immunity, 5(4): 319-330 (1996).
Rosetti et al., "The many faces of Mac-1 in autoimmune disease," Immunological Reviews, 269: 175-193 (2016).
Ruiz et al., "Resolution of inflammation during multiple sclerosis," *Semin. Immunopathol.*, 2019, 41(6): 711-726.
Russo et al., "Platelet-Activating Factor Mediates CD40-Dependent Angiogenesis and Endothelial-Smooth Muscle Cell Interaction," The Journal of Immunology, 5489-5497 (2003).
Santilli et al., "CD40/CD40L system and vascular disease," *Intern. Emerg. Med.*, 2007, 2(4): 256-268.
Sarawar et al., "Stimulation via CD40 can substitute for CD4 T cell function in preventing reactivation of latent herpesvirus," PNAS, 98: 6325-6329 (2001).

Sawcer et al., "Genetic risk and a primary role for cell-mediated immune mechanisms in multiple sclerosis," Nature, 476(7359): 214-219 (2011).
Sawcer, "The complex genetics of multiple sclerosis: pitfalls and prospects," Brain, 131: 3118-3131 (2008).
Schonbeck et al., "Molecules in focus, CD154 (CD40 ligand)," The International Journal of Biochemistry & Cell Biology 32: 687-693 (2000).
Schonbeck et al., "The CD40/CD154 receptor/ligand dyad," CMLS—Cellular and Molecular Life Sciences, 58: 4-43 (2001).
Schuh et al., "Features of Human CD3+CD20+ T Cells," *J. Immunol.*, 2016, 197(4): 1111-1117.
Seijkens et al., "CD40-CD40L: linking pancreatic, adipose tissue and vascular inflammation in type 2 diabetes and its complications," Diab Vasc Dis Res, 10: 115-122 (2012).
Seko et al., "Expression of Tumor Necrosis Factor (TNF) Receptor/ Ligand Superfamily Co-Stimulatory Molecules CD40, CD30L, CD27L, and Ox40L in Murine Hearts with Chronic Ongoing Myocarditis Caused by Coxsackie Virus B3," J. Pathol., 188: 423-430 (1999).
Sharma et al., "Glioma-derived exosomes drive the differentiation of neural stem cells to astrocytes," *PLoS One* 2020, 15(7): e0234614.
Siebert et al., "An analytical workflow for investigating cytokine profiles," Cytometry A, 73(4): 289-298 (2008).
Siracusa et al., "Astrocytes: Role and Functions in Brain Pathologies," *Front. Pharmacol.* 2019, 10: 1114.
Skolnick et al., "From genes to protein structure and function: novel applications of computational approaches in the genomic era," Trends in Biotech, 18: 34-39 (2000).
Smith et al., "Multi-peptide coupled-cell tolerance ameliorates ongoing relapsing EAE associated with multiple pathogenic autoreactivities," Journal of Autoimmunity, 27(4): 218-231 (2007).
Steck et al., "Genetics of type 1 c!iabetes," Clinical Chemistry, 57(2): 176-185 (2011).
Stein et al., "Long-term reversal of hypercholesterolemia in low density lipoprotein receptor (LDLR)-deficient mice by adenovirus-mediated LDLR gene transfer combined with CD154 blockade," The Journal of Gene Medicine, 2(1): 41-51 (2000).
Stumpf et al., "Enhanced levels or CD154 (CD40 ligand) on platelets in patients with chronic heart failure," The European Journal of Heart Failure, 5: 629-637 (2003).
Stys et al., "Recent advances in understanding multiple sclerosis," *F1000Res*, 2019, 8: 8 pages.
Sun et al., "Characterization and Biomarker Analyses of Post-COVID-19 Complications and Neurological Manifestations," *Cells*, 2021, 10(386): 17 pages.
Sun et al., "Co-stimulation agonists as a new immunotherapy for autoimmune diseases," Trends in Molecular Medicine, 9(11): 483-489 (2003).
Takada et al., "Integrin Binding to the Trimeric Interface of CD40L Plays a Critical Role in CD40/CD40L Signaling," J. Immunol., 203: 1383-1391 (2019).
Takahashi et al., "The role of extracellular vesicle microRNAs in cancer biology," *Clin. Chem. Lab Med.*, 2017, 55(5): 648-656.
Takeda et al., "Neuronal Differentiation of Human Mesenchymal Stem Cells Using Exosomes Derived from Differentiating Neuronal Cells," *PLoS One*, 2015, 10(8): e0135111.
Thorsby et al., "Particular HLA-DQ molecules play a dominant role in determining susceptibility or resistance to Type 1 (insulin-dependent) diabetes mellitus," Diabetologia, 36(5): 371-377 (1993)(Abstract Only).
Thouvenot., "Update on clinically isolated syndrome," *Presse Med.*, 2015, 44(4 Pt 2): e121-136.
Toubi et al., "The Role of CD40-CD154 Interactions in Autoimmunity and the Benefit of Disrupting this Pathway," Autoimmunity, 37: 457-464 (2004).
Townsend et al., "CD40 signaling regulates innate and adaptive activation of microglia in response to amyloid b-peptide," Eur. J. Immunol., 35: 901-910 (2005).
Vaitaitis et al., "Cutting Edge: CD40-Induced Expression of Recombination Activating Gene (RAG) 1 and RAG2: A Mechanism for the Generation of Autoaggressive T Cells in the Periphery," The Journal of Immunology, 170: 3455-3459 (2003).

(56) References Cited

OTHER PUBLICATIONS

Vaitaitis et al., "A CD40 targeting peptide prevents severe symptoms in experimental autoimmune encephalomyelitis," *J. Neuroimmunol.*, 2019, 332: 8-15.
Vaitaitis et al., "A CD40-targeted peptide controls and reverses type 1 diabetes in NOD mice," Diabetologia, 57: 2366-2373 (2014).
Vaitaitis et al., "An Alternative Role for Foxp3 As an Effector T Cell Regulator Controlled through CD40," The Journal of Immunology, 191: 717-725 (2013).
Vaitaitis et al., "Biomarker discovery in pre-Type 1 Diabetes; Th40 cells as a predictive risk factor," *J. Clin. Endocrinol. Metab.*, 2019, 104(9): 4127-4142.
Vaitaitis et al., "CD40 glycoforms and TNF-receptors 1 and 2 in the formation of CD40 receptor(s) in autoimmunity," Molecular Immunology, 47: 2303-2313 (2010).
Vaitaitis et al., "CD40 interacts directly with RAG1 and RAG2 in autoaggressive T cells and Fas prevents CD40 induced RAG expression," Cellular and Molecular Immunology, 10(6): 483-489 (2013).
Vaitaitis et al., "CD40-mediated signalling influences trafficking, T-cell receptor expression, and T-cell pathogenesis, in the NOD model of type 1 diabetes," Immunology, 152: 243-254 (2017).
Vaitaitis et al., "CD40-targeted peptide proposed for type 1 diabetes therapy lacks relevant binding affinity to its cognate receptor Reply to Pagni PP, Wolf A, Lo Conte M et al [letter]," Diabetologia, 62: 1730-1731 (2019).
Vaitaitis et al., "Galectin-9 Controls CD40 Signaling through a Time Independent Mechanism and Redirects the Cytokine Profile of Pathogenic T Cells in Autoimmunity," PLoS One, 7(6): e38708:1-13 (2012).
Vaitaitis et al., "High Distribution of CD40 and TRAF2 in TMO T Cell Rafts Leads to Preferential Survival of this Auto-Aggressive Population in Autoimmunity," PLoS One, 3(4): e2076: 1-11 (2008).
Vaitaitis et al., "Th40 cells (CD4+CD40+ Tcells) drive a more severe form of Experimental Autoimmune Encephalomyelitis than conventional CD4 T cells," PLoS One, 12: e0172037 pp. 1-24 (2017).
Vaitaitis et al., "The Expanding Role of TNF-Receptor Super Family Member CD40 (tnfrsf5) in Autoimmune Disease: Focus on Th40 Cells," Current Immunology Reviews, 6(2): 130-136 (2010).
Van Kooten et al., "CD40-CD40 ligand," *J. Leukoc. Biol.*, 2000, 67(1): 2-17.
Varo et al., "Soluble CD40L—Risk Prediction After Acute Coronary Syndromes," Circulation, 108: 1049-1052 (2003).
Vaz et al., "Phenotypic Effects of Wild-Type and Mutant SOD1 Expression in N9 Murine Microglia at Steady State, Inflammatory and Immunomodulatory Conditions," *Front. Cell. Neurosci.*, 2019, 13: 109.
Verma et al., "Not Just an Adhesion Molecule: LFA-1 Contact Tunes the T Lymphocyte Program," The Journal of Immunology, 199: 1213-1221 (2017).
Wagner et al., "Expression of CD40 identifies a unique pathogenic T cell population in type 1 diabetes," PNAS, 99(6): 3782-3787 (2002).
Wagner et al., "Increased expression of CD40 on thymocytes and peripheral T cells in autoimmunity: A mechanism for acquiring changes in the peripheral T cell receptor repertoire," International Journal of Molecular Medicine, 4: 231-242 (1999).
Waid et al., "A unique T cell subset described as CD4loCD40+ T cells (TCD40) in human type 1 diabetes," Clinical Immunology, 124: 138-148 (2007).
Waid et al., "A unique T cell subset, Th40, are pathogenic and diagnostic in mulitple sclerosis," Journal of Immunology, 186(1): Meeting Abstract (2011).
Waid et al., "Disruption of the homeostatic balance between autoaggressive (CD4+CD40+) and regulatory (CD4+CD25+FoxP3+) T cells promotes diabetes," Journal of Leukocyte Biology, 84: 431-439 (2008).
Waid et al., "Peripheral CD4loCD40+ auto-aggressive T cell expansion during insulin-dependent diabetes mellitus," Eur. J. Immunol, 34: 1488-1497 (2004).
Walling et al., "LFA-1 in T Cell Migration and Differentiation," Frontiers in Immunology, 9: Article 952 (2018).
Winer et al., "B Lymphocytes promote insulin resistance through modulation of T Lymphocytes and production of pathogenic IgG antibody," Nat Med, 17: 610-617 (2011).
Winston et al., "Assessing Neuronal and Astrocyte Derived Exosomes From Individuals With Mild Traumatic Brain Injury for Markers of Neurodegeneration and Cytotoxic Activity," *Front. Neurosci.*, 2019, 13: 1005.
Wucherpfennig et al., "A Review of T-Cell Receptors in Multiple Sclerosis: Clonal Expansion and Persistence of Human T-Cells Specific for an Immunodominant Myelin Basic Protein Peptidea," Annals of the New York Academy of Sciences, 756(1): 241-258 (1995).
Yu et al., "Reduced oligodendrocyte exosome secretion in multiple system atrophy involves SNARE dysfunction," *Brain a Journal of Neurology*,, 2020, 143(6): 1780-1797.
Yu et al., "Targeting CD40 with a Selective Phage Display Derived Peptide," pp. 61-74.
Zhang et al., "T cell and antibody responses in remitting-relapsing experimental autoimmune encephalomyelitis in (C57BL/6 × SJL) F1 mice," Journal of Neuroimmunology, 148(1-2): 1-10 (2004).
Zhang et al., "The regulation of integrin function by divalent cations," Cell Adhesion & Migration, 6(1): 20-29 (2012).

\* cited by examiner

% Diabetes Inhibition with CD40 Ligand Inhibitory Peptide

| | |
|---|---|
| 6-mer = | A-K-K-G-Y-Y (SEQ ID NO: 29) |
| 8-mer = | A-K-K-G-Y-Y-T-M (SEQ ID NO: 5) |
| 10-mer = | W-A-K-K-G-Y-Y-T-M-K (SEQ ID NO: 24) |
| 13-mer = | V-L-Q-W-A-K-K-G-Y-Y-T-M-K (SEQ ID NO: 25) |
| 15-mer = | V-L-Q-W-A-K-K-G-Y-Y-T-M-K-S-N (SEQ ID NO: 7) |
| 24-mer = | A-A-S-V-L-Q-W-A-K-K-G-Y-Y-T-M-K-S-N-L-V-V-L-E-N (SEQ ID NO: 32) |

ELISA measuring CD40 in blood samples

FIG. 9

| SEQ ID NO: 9 | 24-mer | AASVLQWAKKGYYTMKSNLVMLEN | 2 min. |
| SEQ ID NO: 7 | 15-mer | VLQWAKKGYYTMKSN | >100 hr. |
| SEQ ID NO: 25 | 13-mer | VLQWAKKGYYTMK | 30 hr. |
| SEQ ID NO: 24 | 10-mer | WAKKGYYTMK | 2 hr. |
| SEQ ID NO: 6 | 8-mer | AKKGYYTM | 1 hr. |
| SEQ ID NO: 29 | 6-mer | AKKGYY | 30 min. |

FIG. 10

(SEQ ID NO: 7) VLQWAKKGYYTMKSN  mouse
(SEQ ID NO: 8) VLQWAEKGYYTMSNN  human

EAE Course

EAE course

Th40 IL-10; dLN

Th40 IL-10; Spleen

Conv. CD4 IL-10; dLN

Conv. CD4 IL-10; Spleen

Th40 TNFα

Th40 IFNγ

Th40 IL-2

Th40 IL-17

Th40 effector (CD44+CD62L-)

Th40 central (CD44+CD62L+)

Conv. CD4 effector (CD44+CD62L-)

Conv. CD4 central (CD44+CD62L+)

(SEQ ID NO: 3)

SEQUENCE LISTING

<160> NUMBER OF SEQ ID NOS: 31

<210> SEQ ID NO 1
<211> LENGTH: 260
<212> TYPE: PRT
<213> ORGANISM: Mus musculus

<400> SEQUENCE: 1

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 2
<211> LENGTH: 261
<212> TYPE: PRT
<213> ORGANISM: Homo sapiens

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val

```
                50                  55                  60
Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Thr Lys Lys Glu Asn Ser Phe Glu
                100                 105                 110

Met Gln Lys Gly Asp Gln Asn Pro Gln Ile Ala Ala His Val Ile Ser
                115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 4
<212> TYPE: PRT
<213> ORGANISM: Mus muculus

<400> SEQUENCE: 3

Lys Gly Tyr Tyr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Lys Lys Gly Tyr Tyr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Ala Lys Lys Gly Tyr Tyr Thr Met
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Ala Glu Lys Gly Tyr Tyr Thr Met
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Val Leu Gln Trp Ala Lys Lys Gly Tyr Tyr Thr Met Lys Ser Asn
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Val Leu Gln Trp Ala Glu Lys Gly Tyr Tyr Thr Met Ser Asn Asn
1               5                   10                  15

<210> SEQ ID NO 9
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 9

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11
```

```
Gly Leu Gln Trp Ala Lys Lys Gly Tyr Tyr Thr Met Lys Ser Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Val Gly Gln Trp Ala Lys Lys Gly Tyr Tyr Thr Met Lys Ser Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Val Leu Gly Trp Ala Lys Lys Gly Tyr Tyr Thr Met Lys Ser Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Val Leu Gln Gly Ala Lys Lys Gly Tyr Tyr Thr Met Lys Ser Asn
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Val Leu Gln Trp Gly Lys Lys Gly Tyr Tyr Thr Met Lys Ser Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Val Leu Gln Trp Ala Gly Lys Gly Tyr Tyr Thr Met Lys Ser Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Val Leu Gln Trp Ala Lys Gly Gly Tyr Tyr Thr Met Lys Ser Asn
```

```
<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Val Leu Gln Trp Ala Lys Lys Gly Gly Tyr Thr Met Lys Ser Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Val Leu Gln Trp Ala Lys Lys Gly Tyr Gly Thr Met Lys Ser Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Val Leu Gln Trp Ala Lys Lys Gly Tyr Tyr Gly Met Lys Ser Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Val Leu Gln Trp Ala Lys Lys Gly Tyr Tyr Thr Gly Lys Ser Asn
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

Ile Ser Gln Ala Val His Ala Ala His Ala Glu Ile Asn Glu Ala Gly
1               5                   10                  15

Arg

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23
```

Tyr Val Gln Gly Lys Ala Asn Leu Lys Ser Lys Leu Met Tyr Thr
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Trp Ala Lys Lys Gly Tyr Tyr Thr Met Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Val Leu Gln Trp Ala Lys Lys Gly Tyr Tyr Thr Met Lys
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Ala Ala Ser Val Leu Gln Trp Ala Lys Lys Gly Tyr Tyr Thr Met Lys
1               5                   10                  15

Ser Asn Leu Val Met Leu Glu Asn
            20

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 27

Lys Gly Tyr Tyr Thr Met
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 28

Ala Glu Lys Gly Tyr Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide

```
<400> SEQUENCE: 29

Ala Lys Lys Gly Tyr Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Ala Lys Gly Tyr Tyr Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Tyr Lys Asn Val Lys Gln Met Ala Tyr Trp Leu Thr Gly Lys Ser
1               5                   10                  15
```

METHODS FOR REDUCING SYMPTOMS OF MULTIPLE SCLEROSIS USING A SIX-AMINO ACID LONG PEPTIDE THAT INHIBITS CD40-CD150 INTERACTION

This invention was made with government support under grant number R41 AI113977 awarded by the National Institute of Allergy and Infectious Disease and grant number RG 5070-A-1 awarded by the National Multiple Sclerosis Society. The government may have certain rights in the invention.

REFERENCE TO SEQUENCE LISTING

This application contains a Sequence Listing submitted as an electronic text file entitled "OPB-00701_SL" having a size in bytes of 11,791 bytes and created Jun. 17, 2021. The information contained in this electronic file is hereby incorporated by reference in its entirety pursuant to 37 CFR 1.52(e)(5).

FIELD

The present developments relate to peptides that alter the interaction of CD40 and CD154, and the use of such compounds in modulating T-cell activity and in treating disease.

Multiple sclerosis (MS) is a complex disease of which the cause is still unknown. The disease may be triggered by an unidentified environmental factor in a person who is genetically predisposed to develop the condition.

BACKGROUND

Inflammation normally occurs in response to infection by invading micro-organisms. This inflammatory response is beneficial because it is an important part in localizing the infecting agent for removal by the immune system. However, in autoimmunity there is no infection, yet severe inflammation is present. The inflammation in this case—referred to as aseptic chronic inflammation (ACI)—is detrimental since it destroys normal tissues. The results of this aseptic inflammation are life-altering and in some cases life-threatening. Moreover, as with acute inflammation, this process is mediated by immune cells, including T-cells.

A major concern for modern medicine is how to control ACI such as that which occurs during autoimmune diseases, as well as how to control acute inflammation resulting from trauma. Inflammation, both chronic and acute, leads to tissue degeneration and eventual loss of function of major organs. ACI is not limited to a single disease, but is instrumental in numerous autoimmune diseases including, but not limited to type 1 diabetes, multiple sclerosis, systemic lupus erythematosa, rheumatoid arthritis, Crohn's disease, inflammatory bowel disease, chronic obstructive pulmonary disease including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome, acute lung injury, and ACI associated with organ transplantation.

Autoimmune disorders are classified into two types: organ-specific (directed mainly at one organ) and non-organ-specific (widely spread throughout the body). Examples of organ-specific autoimmune disorders are insulin-dependent Type 1 diabetes which affects the pancreas; Hashimoto's thyroiditis and Graves' disease, which affect the thyroid gland; pernicious anemia, which affects the blood; Addison's disease, which affects the adrenal glands; chronic active hepatitis, which affects the liver; myasthenia gravis which affects the muscle; and multiple sclerosis, which affects tissue of the nervous system. Examples of non-organ-specific autoimmune disorders are rheumatoid arthritis and polyglandular disease. Autoimmune diseases are often chronic, debilitating, and life-threatening. The National Institutes of Health (NIH) estimates that up to 23.5 million Americans suffer from autoimmune disease and that the prevalence is rising. It has been estimated that autoimmune diseases are among the ten leading causes of death among women in all age groups up to 65 years.

Acute inflammation, as observed during trauma or sepsis, is also immune cell mediated. While all of the molecular mediators in this process have not yet been identified, a prominent role for T cells, macrophages/monocytes, neutrophils etc., is strongly implicated. Therefore a system, method or composition or device to modulate these cell types would necessarily control the inflammatory response.

A unique T cell subset has been shown to be instrumental in the development of autoimmune disease. These cells are phenotypically characterized as CD4loCD40+ (Waid, D. M., et al., *Eur. J. of Immunol.*, 34:1488, 2004; Vaitaitis, G. M., et al., *Cutting Edge, J. Immunol.*, 170:3455, 2003; Wagner, D. H., Jr., et al., *Proc. Nat'l. Acad. Sci. USA*, 99:3782, 2002; Wagner, D. H., Jr., et al., *Int'l J. of Mol. Med.* 4:231, 1999) and CD4hiCD4+ and are referred to as Th40 cells. (Waid, D. M., et al. *Eur. J. of Immunol.* 34:1488, 2004; Vaitaitis, G. M., et al., *Cutting Edge, J. Immunol.* 170:3455, 2003; Wagner, D. H., Jr., et al., *Proc. Nat'l Acad. Sci. USA* 99:3782, 2002; Wagner, D. H., Jr., et al., *Int'l J. of Mol. Med.* 4:231, 1999). CD40 expression typically is associated with antigen presenting cells and the majority of prior art describes CD40 as being expressed on B cells, macrophages, monocytes, and other cells; however, CD40 proteins are also expressed on T cells (Waid, D. M., et al., 2004. *Eur. J. of Immunol.*, 34:1488, 2004; Vaitaitis, G. M., et al., *Cutting Edge, J Immunol.*, 170:3455, 2003; Wagner, D. H., Jr., et al., *Proc. Nat'l Acad. Sci. USA*, 99:3782, 2002; Wagner, D. H., et al., *Int'l. J of Mol. Med.*, 4:231, 1999; Bourgeois, C., et al., *Science*, 297:2060, 2002; Fanslow, W. C., et al., *J. of Immun.*, 152:4262, 1994; Ramsdell, F., et al., *J. of Immunol.* 152: 2190, 1994; Grabstein, K. H., et al., *J. of Immunol.*, 150: 3141, 1993; Armitage, R. J., et al., *Sem. in Immun.*, 5:401, 1993; Cooper, C. J., et al., *J of Immunol.*, 173:6532, 2004). While Th40 cells include a proportion of the peripheral CD4+ compartment in naïve, non-autoimmune mice (Waid, D. M., et al., *Eur. J. of Immunol.*, 34:1488, 2004; Wagner, D. H., Jr., et al., *Intl J. of Mol. Med.*, 4:231, 1999; Waid, D. M., et al., J. of Neuroimmunol., 270:1-2:75, 2014), and in humans (Waid. D. M., et al., *Clin. Immunol.* 124:138, 2007), this proportion is drastically expanded to as much as 50% of the CD4+ compartment in autoimmune prone mice (Waid, D. M., et al., *Eur. J. of Immunol.* 34:1488, 2004; Wagner, D. H., Jr., et al., *Proc. Nat'l Acad. Sci. USA* 99:3782, 2002; Wagner, D. H., et al., *Intl'l J. of Mol. Med.*, 4:231, 1999) and humans (Waid. D. M., et al., *Clin. Immunol.* 124:138, 2007; Waid, D. M., et al., J. of Neuroimmunol., 270:1-2:75, 2014). These T cells do not express early activation markers and occur in the naïve phenotype of non-challenged mice. There are CD4hi cells, especially in multiple sclerosis that express CD40, in addition to CD10 cells.

In NOD (non-obese diabetic) mice, a mouse model of Type 1 Diabetes, Th40 cells occur at exaggerated levels in spleen, lymph nodes and the pancreas, even prior to diabetes onset (Waid, D. M., et al., *Eur. J. of Immunol.* 34:1488, 2004;

Wagner, D. H., Jr., et al., *Proc. Nat'l Acad. Sci. USA* 99:3782, 2002). An elevated number and percentage of these T cells are seen in peripheral blood of type 1 diabetic (T1D) patients when compared to non-autoimmune controls and type 2 diabetic patients (Waid. D. M., et al., *Clin. Immunol.*, 124:138, 2007).

The observed increase in Th40 cells could mean that those T cells are antigen responsive or that CD40 expression is activation induced. Furthermore, several diabetogenic T cell clones are CD40+ (Wagner, D. H., Jr., et al., *Proc. Nat'l Acad. Sci. USA* 99:3782, 2002). Purified primary Th40 cells from NOD mice and from pre-diabetic NOD (12-weeks of age) mice successfully transfer type 1 diabetes to NOD/scid (Non-Obese Diabetic/Severe Combined Immunodeficiency) recipient mice, directly demonstrating pathogenicity of the Th40 T cell subset (Waid, D. M., et al., *Eur. J. of Immunol.* 34:1488, 2004; Wagner, D. H., Jr., et al., *Proc. Nat'l Acad. Sci. USA*, 99:3782, 2002). It has been shown that Th40 cells infiltrate islet beta cells destroying insulin production thus suggesting islet antigen specificity (Waid, D. M., et al., *Eur. J. of Immunol.* 34:1488, 2004; Wagner, D. H., Jr., et al., *Proc. Nat'l Acad. Sci. USA* 99:3782, 2002). It has also been shown that Th40 cells are required for diabetes transfer. Peripheral (spleen and regional lymph node) T cells that were CD40 depleted, then CD25, Treg, depleted were not capable of transferring diabetes to Scid (Severe Combined Immunodeficiency) recipients. Even though Treg cells were removed, if the auto-aggressive $CD40^+$ T cells subset is absent, disease transfer does not occur.

While Th40 cells are important in the development of autoimmunity, another important factor is expression of the CD40—Ligand, CD154. CD154 is temporally induced on activated T-cells in response to CD3/TCR stimulation (Lederman, S. et al., *J. of Exp. Med.*, 175:1091, 1992). CD154 expression has also been demonstrated on platelets, monocytes, basophils, eosinophils, dendritic cells, fibroblasts, smooth muscle, and endothelial cells (Russo, S. et al., *J. Immunol.* 171:5489, 2003; Stumpf, C., et al., *Eur. J. Heart Fail.*, 5:629, 2003; Schonbeck, U., et al., *Cell Mol. Life Sci.* 58:4, 2001). CD154 is a member of the tumor necrosis factor (TNF) super-family and a soluble form of CD154 (sCD154) has been described. (Russo, S., et al., *J. Immunol.* 171:5489 2003; Stumpf, C., et al., *Eur. J. Heart Fail* 5:629, 2003; Toubi, E., et al., *Autoimmunity* 37:457, 2004). Therefore, sCD154 may act like a cytokine. (Stumpf, C., et al., *Eur. J. Heart Fail.* 5:629, 2003). Even though CD154 has not been genetically linked in T1D studies, sCD154 is significantly elevated in T1D and may play a role in the disease process (Varo, N. et al., *Circulation* 107:2664, 2003; Cipollone, F., et al., *Diabetologia* 48:1216, 2005; Devaraj, S., et al., *Diabetes* 55:774, 2006). The importance of CD40—CD154 interaction in autoimmunity has been established (Wagner, D. H., Jr., et al., *Proc. Nat'l Acad. Sci. USA* 99:3782, 2002; Kobata, T., et al., *Rev. Immunogenet.* 2:74, 2000; Homann, D., et al., *Immunity* 16:403, 2002; Goodnow, C. C., et al., *Lancet* 357:2115, 2001; Balasa, B., et al., *J. of Immunol.* 159:4620, 1997). Blocking CD40—CD154 interaction may prevent collagen induced arthritis, (Dune, F. H., et al., *Science* 281:1328, 1993) experimental autoimmune encephalitis (Howard, L. M., et al., *Autoimmunity* 37:411, 2004), prostatitis (Grossman, M. E., et al., *J. Immunother.* 24:237, 2001), and T1D in the NOD mouse model (Dune, F. H. et al., *Science* 281:1328, 1993; Balasa, B. et al., *Journal of Immunology* 159:4620, 1997; Howard, L. M., et al., *Autoimmunity* 37:411, 2004; Grossman, M. E. et al., *J. Immunother.* 24:237, 2001). In the diabetes model, it was essential to administer a CD154 blocking antibody to NOD mice at 3-weeks of age because at 9-weeks, blocking antibodies had no effect on diabetes prevention (Balasa, B. et al., *J. of Immunol.* 159:4620, 1997).

Previous work has also demonstrated that the Th40 cell subset induces RAG1 and RAG2 (Recombination-Activating Genes) transcription, translation and nuclear translocation (Vaitaitis, G. M., et al., *Cutting Edge, J. Immunol.* 170:3455, 2003) when CD40 is engaged (Vaitaitis, G. M. et al., *Cutting Edge, J. Immunol.* 170:3455, 2003). CD3 engagement does not induce RAG1 or RAG2 in T-cells (Vaitaitis, G. M., et al., *Cutting Edge, J. Immunol.* 170:3455, 2003). Subsequent to RAG1/RAG2 induction, CD40-mediated T-cell receptor (TCR) revision occurs in peripheral T cells (Vaitaitis, G. M., et al., *Cutting Edge, J. Immunol.* 170:3455, 2003). CD40 induction of TCR revision is RAG dependent. T cells isolated from a TCR-Tg mouse undergo TCR revision when CD40 engaged, but T-cells from the TCR-Tg.RAG−/− mouse do not TCR revise when CD40 engaged (Wagner, D. H., Jr. et al., *Intl J. of Mol. Med.* 4:231, 1999).

CD40 is a 50-kDa integral membrane protein of the tumor necrosis factor receptor (TNF-R) family. It is constitutively expressed as a homotrimer (Foy T M, et al., *Ann. Rev. of Immunol.*, 14:591, 1996). In general, stimulation of all CD40-expressing cell types induces operations which contribute to inflammation, such as enhancement of costimulatory and adhesion molecules, and up-regulation of proteolytic enzymes (Mach, F. et al., *Atherosclerosis.* 137 Suppl: S89-95, 1998).

CD40's ligand—CD154—is a 39-kDa protein that belongs to the tumor necrosis factor (TNF) family. CD40 forms a trimer that binds CD154 at the interface of the three monomers. CD154 is expressed commonly on cells beyond the surface-expressed CD154, as CD154 may also exist in a soluble biologically active form (sCD154) that is shed from the cell surface after activation. The main source of sCD154 is platelets. (Kaufman, J., et al., *J. of Thrombosis and Haemostasis*, 5:788-96, 2007).

Interestingly, it appears that there may be several different forms of the CD40 receptor, either because of glycosylation differences in the protein itself, or because of the interaction of CD40 with other molecules. (Peters, A. L., et al., *Seminars in Immunology*, 21(5):293, 2009; Vaitaitis, G. M., et al., *Mol. Immunol.* 47(14):2303, 2010; Vaitaitis, G. M., et al., *PLoS One*, 7(6):38708, 2012). A less glycosylated form of CD40 appears to be associated with more activated cells. (Peters, A. L., et al., *Seminars in Immunology*, 21(5):293, 2009). Therefore, it may be suitable to target such activated immune cells specifically.

Multiple Sclerosis (MS) is an inflammatory demyelinating disease of the central nervous system (CNS). Additionally, not only is MS a disease of the CNS, but MS is primarily an autoimmune disease and several autoimmune components may drive the disease. The autoimmune aspect of the disease was elucidated primarily from studies in the Experimental Autoimmune Encephalomyelitis (EAE) mouse model and from analysis of lesions in the brain and spinal cord of human patients. Sclerotic lesions may form in the brain and spinal cord in both MS and EAE and involve infiltrating inflammatory cells, including macrophages, mast cells and T cells. (See e.g. Baeten, K., et al., *J. of Neuroimmunol.* 195:1, 2008; Hong, G. U., et al., *J. of Neuroimmunol.* 260:60, 2013; Howard, L. M., et al., *J. of Clin. Invest.* 103:281, 1999; Fletcher, J. M., et al., *Clin. And Exp. Immun.* 162:1, 2010; El-behi, M., et al., *J. Neuroimmune Pharmacol.* 5:189, 2010).

While CD8+ T cells may play a role in EAE and MS, CD4+ T cells may be the drivers of the disease. (Huseby, E. S., et al., *J. of Exp. Med.* 194:5, 2001; Denic, A., et al., *Expert. Opin. Ther. Targets,* 17(9):1053, 2013). Th1 cells, which produce IFNγ, TNFα, IL-1β and GM-CSF, may also be centrally involved in inflammation in the MS disease state. IL-6 which is a non-inflammatory cytokine, and originally described as a Th2, is also associated with inflammatory responses in MS. (Furuzawa, J., et al., *Autoimmunity Reviews* 6:169, 2007). More recently, it has been demonstrated that CD4+CD40+ T cells (Th40), which are capable of producing both Th1 and Th17 cytokines simultaneously, may drive a more severe form of EAE than conventional CD4+ T cells (Vaitaitis, G. M., et al., *PLoS One* 12:2, 2017).

The CD40-CD154 interaction is critical in EAE. (Vaitaitis, G. M., et al., *PLoS One* 12:2, 2017; Girvin, A. M., et al., *J. of Autoimmunity* 18:83, 2002). The classically described T cell co-stimulus is CD28 on T cells interacting with B7-1 or B7-2 on antigen presenting cells. Immunological testing has demonstrated that blocking CD28 interactions may result in anergy, or an absence of response from the treated cells or animal. (Oliveira-dos-Santos, A. J., et al., *J. Immunol.* 162:4490, 1999; Lenschow, D. J., et al., *Annu. Rev. Immunol.* 14:233, 1996). In EAE models, the contrary was shown. Early studies suggested that CD28 co-stimulation was crucial for EAE development (Oliveira-dos-Santos, A. J., et al., *J. Immunol.* 162:4490, 1999), and a later study using $CD28^{-/-}$ mice the initial disease induction challenge resulted in no disease (Girvin, A. M., et al., *J. of Autoimmunity* 18:83, 2002). However, a second challenge of the $CD28^{-/-}$ mice resulted in a much more severe fulminant EAE disease state. Under these conditions a treatment that did prevent disease was a CD40-CD154 block. (Girvin, A. M., et al., *J. of Autoimmunity* 18:83, 2002). These findings suggest that CD40 may be a central *nexus* for disease onset and severity and may also suggest that CD40 expression on T cells as an inflammatory co-stimulus and critical factor for disease development. Preventing the interaction of CD40 and CD154 in mice by using blocking antibodies decreases the severity and delays onset of EAE. (Hong, G. U., et al., *J. of Neuroimmunol.* 260:60, 2013; Girvin, A. M., et al., *J. of Autoimmunity* 18:83, 2002). Similar beneficial results from blocking the CD40-CD154 interaction using antibodies has been achieved in other autoimmune disease models (Toubi, E., et al., *Autoimmunity,* 37:6, 2004; Waid, D. M., et al., *E. J. Immunol.* 34: 1488, 2004); however, significant problems were encountered when antibodies were used in human trials (Boumpas, D. T., et al., *Arthritis Rheum.* 48:719-727, 2003; Sidiropoulos, P. I., et al., *Lupus,* 13:391-97, 2004).

Thus, multiple treatment options have been put forward to address and control both chronic and acute inflammation. Many approaches use non-steroidal anti-inflammatory drugs (NSAIDS) that attack the production of leukotrienes and prostaglandins, cellular products that cause localized inflammation. Other approaches use more powerful immunosuppressant drugs such as cyclophosphamide, methotrexate and azathioprine that suppress the immune response and stop the progression of the disease. Still other treatments involve the use of monoclonal antibodies (mAb) designed to alter the immune responses to self-tissues, as occurs during autoimmune diseases. However, all these treatments often have severe, long-term side effects.

Current immune-modulatory therapies may rely upon monoclonal antibody treatments that may give rise to complications. For example, antibodies administered to a subject may cross-react with unintended targets and cause severe nephritic complications and those that specifically act against CD154 may cause embolic complications (Boumpas, D. T., et al., *Arthritis Rheum.* 48:719-727, 2003; Sidiropoulos, P. I., et al., *Lupus,* 13:391-97, 2004). Antibodies as therapeutics may come with intrinsic problems in that they may be immunogenic in the recipient and they can bind to Fc-receptors on cells such as platelets, neutrophils, and macrophages, increasing risk of anaphylaxis.

Further, the CD40-CD154 interaction may play an important role in antibody generation which may indicate that administration of a monoclonal antibody could induce auto-antibody generation and further complications, which may inhibit the restoration of normal immune function (see generally Banchereau, J. et al., *Annu. Rev. of Immunol.* 12:881, 1994).

Other studies have demonstrated that blocking the CD154 interaction by using mAbs or limiting the CD40 receptor by monoclonal antibodies may abrogate atherosclerosis, and may confer a more favorable plaque phenotype characterized by lower inflammation and higher fibrosis (Donners, M. M. P. C., et al., *Hemostasis, Thrombosis, and Vascular Biology,* 111:9, 2008; Lutgens, E., et al., *PNAS,* 97:13, 2000; Lutgens, E., et al., *Nature Medicine,* 5:11, 1999; Mach, F., et al., *Nature,* 394:200, 1998; Schonbeck, U., et al., *PNAS,* 97:7458-63, 2000). These studies additionally demonstrated that neointimal formation and restenosis may be limited by blocking the CD154 interaction (Donners, M. M. P. C., et al., *Hemostasis, Thrombosis, and Vascular Biology,* 111:9, 2008). Studies concerning lupus nephritis may have demonstrated that blocking CD40 mediated signals can reduce anti-double-stranded DNA (anti-dsDNA) antibodies. Moreover, these studies may demonstrate that the reduction of anti-dsDNA was associated with increased serum complement levels and reduced glomerular inflammation, which may be viewed positively from a clinical perspective. However, the use of monoclonal antibodies to target the CD40/CD154 dyad was abandoned due to thromboembolic events which may have been related to the functioning of CD154 in thrombus stabilization. It is postulated that CD154 stabilize thrombi by interaction with the integrin $\alpha_{IIb}\beta_3$, and by inhibiting CD154, thrombi may be less stable, and consequently shed emboli causing thrombotic events (Andre, P., et al. *Nature Medicine,* 8:3, 2002).

Therefore, to overcome the possibly unreconcilable problems encountered by using antibodies, participants in research in the area have attempted to use F(ab) fragments of CD154 antibodies to attempt to block CD40-CD154 interactions (Shock, A., et al., *Arthritis Research & Therapy,* 17:234, 2015). While this approach may avoid the problem of thrombotic events, the fragments still are relatively bulky molecules that may be immunogenic. Other attempts have included using random peptides to bind to CD40 which may bind other targets in-vivo (Kitagawa, M., et al. *Modern Rheumatology,* 15:423, 2005), small organic molecules such as suramin have been proposed; however, these small organic molecules may have toxic side effects and may also lose their activity in protein-rich medium (Margolles-Clark, E., et al., *Biochemical Pharmacology,* 77:1236, 2009).

Accordingly, there exists a desire for safer and more effective methods for treatment and prevention of multiple sclerosis (MS). The present developments may address this by describing methods for treatment of MS by administration of a therapeutically effective amount of a CD40 binding peptide, CD154 derived peptide, or CD40 interfering peptide. Moreover, a therapeutic peptide as described herein may have additional characteristics that help to treat and/or modulate symptoms related to MS. Further, the present developments may provide a benefit of reducing the chances of complications by using a peptide that may be safer due to its smaller size compared to that of a full antibody. Moreover, the present developments may provide a benefit of preventing auto-antibody generation, and thus allow the resumption of normal immune function.

This statement of background is for information purposes only and is not intended to be a complete or exhaustive explication of all potentially relevant background.

SUMMARY

The present developments may provide novel methods and peptides for preventing, modulating, and/or reducing multiple sclerosis (MS) that arises in a corporeal body. MS may arise because of chronic inflammatory response of white blood cells in the central nervous system, including but not limited to the optic nerve, brain stem, basal ganglia, spinal cord, and lateral ventricles. It is postulated that the white blood cells and T cells may recognize the myelin sheaths of the neurons as foreign and attack, damage, and destroy the myelin as part of a chronic inflammatory response. This chronic inflammatory response and the subsequent damage to the myelin may be caused by environmental and genetic factors; however, the exact cause of MS is still unknown.

Given the aspects and problems encountered by others in the field, the current developments may provide a more targeted approach to inhibit the CD40-CD154 interaction and as a result prevent, reduce, modulate, and/or treat MS. Based on the protein domain of the CD154 that is essential for interaction with CD40, several peptides were formulated and designed that span the amino acids that may be critical to the interaction. Moreover, the peptides described and characterized herein have demonstrated the ability and capacity to bind Th40 and memory T cells, affecting the expression of CD69 and IL-10 in the CD4 T cell compartment, ultimately hampering disease development.

In the non-obese diabetic (NOD) mouse model of T1D, one particular 15-mer peptide was highly efficacious in preventing diabetes onset and even reversed hyperglycemia in 56% of newly hyperglycemic mice. However, the current developments alternatively propose using a smaller core region of the 15-mer peptide, a 6-amino acid sequence (which may be referred to as $KGYY_6$—which may reference SEQ ID NOs: 4, 27, 28, 29, and 30) to prevent or ameliorate EAE symptoms in the mouse model for MS. Peptides of other lengths may be used so long as the core sequence (SEQ ID NO: 3) is conserved in the peptide.

The present developments are based on the knowledge that interaction of CD40-ligand (CD154 protein) with CD40 protein expressed on T-cells (Th40 cells), may be involved in the development of MS and autoimmune diseases, more generally. The present developments may be based on the elucidation of the residues in CD40 and CD154 that may be important for this interaction. The present developments may be involved in modulating the interaction between a CD40 protein and a CD154 protein through the use of small peptides that interact with the CD40 protein at a site where the CD154 protein would normally bind. The present developments may in some instances also relate to using such peptides to reduce the level of Th40 cells, which may thereby reduce the severity of disease. Conversely, the present developments may reduce MS related symptoms without reducing the level of Th40 cells in a patient.

One implementation of the present developments is a method for preventing, modulating, treating, and/or reducing multiple sclerosis including contacting the CD40 protein with a peptide that interacts with the CD40 protein. Preferred peptides may be those that are less than 25 amino acids in length, and that bind to a CD40 protein, and may thereby inhibit its interaction with a CD154 protein.

One implementation of the present developments is a method for preventing, modulating, treating and/or reducing multiple sclerosis, the method including modulating an interaction between a CD40 protein and a CD154 protein with a peptide that may interact with the CD40 protein. Preferred peptides may interact with the CD40 protein at the CD154—binding site. Preferably such peptides are less than 25 amino acids in length. Even more preferred peptides are those amino acid sequences selected from SEQ ID NOs: 3-9 and SEQ ID NOs: 27, 28, 29, and 30.

One implementation of the present developments is a method for preventing, modulating, treating and/or reducing multiple sclerosis in a patient, the method including administering to a subject a peptide of six amino acids or less in length, selected from SEQ ID NOs: 4, 27, 28, 29 and 30.

An additional aspect of the current developments is a method for preventing, modulating, treating and/or reducing multiple sclerosis in a patient, the method including administering to a subject a peptide that inhibits the interactions between CD40 and CD154, the peptide containing the sequence of SEQ ID NO: 3.

One implementation of the present developments is a method for preventing, modulating, and/or reducing multiple sclerosis, the method including administering to a subject, a therapeutically effective amount of a peptide that affects the interaction of CD40 with CD154/CD40-ligand. An aspect of this development may be that the peptide binds to CD40. In this implementation, the peptide may bind to a CD40 protein with a Kd of less than 10'. Further, in this implementation, the peptide may affect the interaction between CD40 and CD154. Additionally, a preferred implementation may inhibit the binding of CD40 to CD154. Moreover, in this implementation, the peptide binds to CD40 at the site where CD40 interacts with CD154. In this implementation, the peptide affects the interaction of CD40 with CD154 in such a manner as to prevent the expansion of Th40 cells. In this implementation, the peptide may affect the interaction of CD40 with CD154 in such a manner as to alter the cytokine expression profile of a cell population, treated with said peptide.

In another implementation, a peptide hereof may affect the interaction of CD40 with CD154 in such a manner as to reduce the number of Th40 cells. Conversely, in other implementations such a peptide may have no effect on the number of Th40 cells in the treated subject.

Another implementation of the present developments may be a method to administer a CD40 peptide to prevent, modulate, and/or reduce multiple sclerosis, including selecting a peptide that interacts with CD40 at the CD154 binding site, selecting a delivery method selected from the group of intramuscular (IM) delivery, intravenous (IV) delivery, subcutaneous (SC) delivery, oral delivery, gavage delivery, emollient/skin delivery, or transdermal patch.

Another implementation of the present developments, may be a method to administer a CD40 peptide to prevent, modulate, and/or reduce multiple sclerosis in an animal, including selecting a peptide that interacts with a CD40 protein and CD154 binding site, using an extended delivery method selected from the group of an implantable device, a hydrophilic polymer formulation, a permeable polymeric membrane, injectable gel implants, solvent extraction system, phase inversion system, thermosensitive gels, pH dependent in situ gels, microparticles, microspheres, nanoparticles, nanospheres, bio-degradable implants, or photo-activated depot.

Another implementation of the present developments, may be a method for preventing multiple sclerosis in a subject including administering to the subject, a therapeutically effective amount of a peptide that affects the interaction of CD40 with CD154/gp39/CD40-ligand.

BRIEF DESCRIPTION OF THE DRAWINGS

In the drawings:

FIG. 9 is a table providing the relative peptide stability assessed by ExPaSY analysis.

FIG. 10 is comparison of the amino acid sequence of a CD154 protein of a mouse and a human.

DETAILED DESCRIPTION

Figure 1:
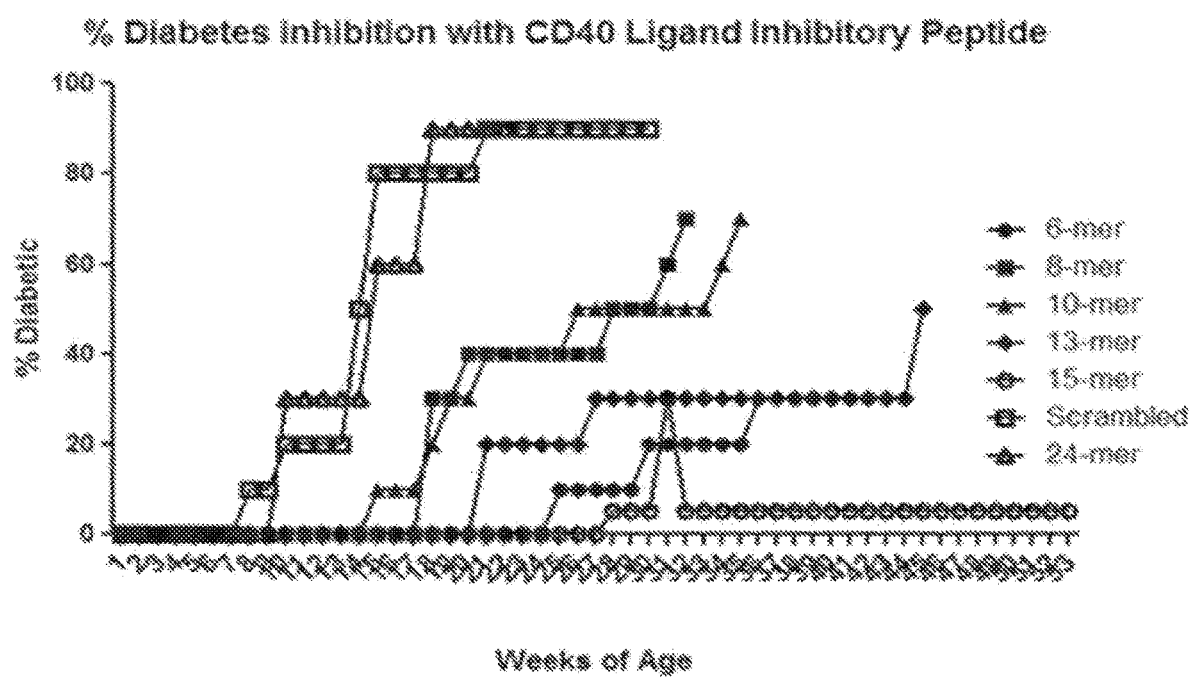
FIG. 1 is a chart of the effect of various peptides of CD154 on the development of diabetes in NOD mice. The 6-mer Form 2 (SEQ ID NO: 29), 8-mer (SEQ ID NO: 5), 10-mer (SEQ NO: 24), 13-mer (SEQ ID NO: 25), 15-mer (SEQ ID NO: 7), and 24-mer (SEQ ID NO: 26) were tested.

The present developments are based on the discovery that a unique subset of T-cells, which express CD40 protein, and thus are referred to as Th40 cells, may be useful in autoimmune inflammation. Moreover, involvement of Th40 cells in the autoimmune process may be dependent on the interaction between CD40 protein expressed on the surface of the T-cell, and CD154 protein. Interaction of CD40 and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction may modulate Th40 cell activity, and thereby affect inflammation. Thus the present developments relate to peptides that affect the interaction between a CD40 protein and a CD154 protein, thereby modulating inflammation. In particular, the present developments relate to peptides that may affect the interaction between CD40 protein expressed on the surface of a T-cell, and a CD154 protein, thereby affecting T-cell activity and modulating inflammation. The developments hereof also relate to methods of using such peptides to modulate inflammation and to treat autoimmune disease. The present developments also encompass the use of such peptides to detect Th40 cells.

Before the present developments are further described, it is to be understood that these developments are not strictly limited to particular implementations described, as such may of course vary. It is also to be understood that the terminology used herein is for the purpose of describing particular implementations only, and is not intended to be limiting, since the scope of the present developments will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

Unless defined otherwise, all technical and scientific terms used herein have the same meaning as commonly understood by one of ordinary skill in the art to which these developments belong. Although any methods and materials similar or equivalent to those described herein can also be used in the practice or testing of the present developments, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present developments are not entitled to antedate such publication by virtue of prior invention. Further, the dates of publication provided may be different from the actual publication dates, which may need to be independently confirmed.

It is appreciated that certain features of the developments, which are, for clarity, described in the context of separate implementations, may also be provided in combination in a single implementation. Conversely, various features of the developments, which are, for brevity, described in the context of a single implementation, may also be provided separately or in any suitable sub-combination. All combinations of the implementations are specifically embraced by the present developments and are disclosed herein just as if each and every combination was individually and explicitly disclosed. In addition, all sub-combinations are also specifically embraced by the present developments and are disclosed herein just as if each and every such sub-combination was individually and explicitly disclosed herein.

It is further noted that the claims may in some instances be drafted to exclude any optional element. As such, this statement is intended to serve as antecedent basis for use of such exclusive terminology as "solely," "only" and the like in connection with the recitation of claim elements or use of a "negative" limitation.

Furthermore, as used herein the term animal refers to a vertebrate, preferably a mammal, more preferably a human. Suitable mammals on which to use the methods of the present developments include but are not limited farm animals, sports animals, pets, primates, mice, rats, horses, dogs, cats, and humans. The term animal can be used interchangeably with the terms subject or patient.

One implementation of the present developments is a peptide that interacts with a CD40 protein in such a manner that may modulate inflammation. As used herein, the terms interact, interaction, and the like, mean that two molecules come into sufficient physical proximity such that they may cause a modulation of inflammation. One type of interaction is a binding interaction. In such an interaction the peptide associates with CD40 to form a complex. An example of complex formation is the association of an antigen with an antibody. According to the present developments, binding of a peptide of the present developments to a CD40 protein can be reversible (e.g., non-covalent binding interactions) or non-reversible (e.g., covalent binding interactions). Moreover, a reversible interaction can be strong or weak, the strength of the interaction being determined by the forces (e.g., ionic charges, hydrogen binding, Van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). Preferred peptides of the present developments are those that bind to a CD40 protein with a Kd of no more than about $1 \times 10^{-6}$ M, about $1 \times 10^{-7}$ M, or about $1 \times 10^{-8}$ M. Particularly preferred peptides are those having a Kd of less than about $1 \times 10^{-9}$ M. In one implementation, a peptide of the present developments binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art.

As used herein, to modulate inflammation means to change the level of inflammatory markers as may be known to an artisan skilled in the art. As used herein, the terms level, number, count and concentration may be used interchangeably. Modulation of inflammation may in some circumstances mean an increase or decrease in the number of Th40 cells present in the inflammatory environment; however, should not be construed as a limitation of the developments hereof. Consequently, modulation can be referred to as positive or negative. Positive modulation (also referred to as up-regulation) of inflammation may in some circumstances refer to an increase in the number of Th40 cells in the inflammatory environment. Negative modulation (also referred to as down-regulation) of inflammation may in some circumstances refer to a reduction in the number of Th40 cells present in the inflammatory environment. However, modulation of inflammation may mean the change in the level of inflammatory markers, biomarkers, or other measurable characteristics of a living body whether at the cellular level or on a more systemic level. In some circumstances, a preferred peptide may be one that down-regulates inflammation, thereby reducing the number of Th40 cells present in the inflammatory environment. Positive and negative modulation of inflammation may or may not result in a change in the type and amount of immunoregulatory molecules present in the inflammatory environment.

It will be appreciated by those skilled in the art that both a cell culture system and the immune system of an animal have basal levels of immune cells and immunoregulatory molecules. The phrases basal level and normal level can be used interchangeably. With regard to the immune system of an animal, as used herein, the basal level of a type of immune cell (e.g., Th40 cell), or a immunoregulatory molecule, refers to the average number of that cell type, or immunoregulatory molecule, present in a population of individuals considered healthy (i.e., free of metabolic, autoimmune, or infectious disease). With regard to a cell culture system, as used herein, the basal level of a type of immune cell, or an immunoregulatory molecule, refers to the average level of that cell type, or immunoregulatory molecule, present in a population of cells that is non-activated. Those skilled in the art are capable of determining if a T-cell, or a population of such cells, is activated. For example, the expression of CD69, CD25 and/or CD154 proteins by a cell indicates that the cell has been activated.

The basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Variability in this measurement can result from differences in the method used to determine the cell count. Furthermore, normal levels of cells can also be reported as a percentage of a total cell population. For example, in a healthy individual, Th40 cells make up less than 25% of the total T cell population. Thus, as used herein, the term inflammation refers to an inflammatory environment in which Th40 cells make up greater than about 25%, greater than about 30%, greater than about 35%, greater than about 40%, greater than about 45%, greater than about 50%, greater than about 55%, greater than about 60%, greater than about 65%, greater than about 70%, greater than about 75%, or greater than about 80% of the total T-cell population. Moreover, a preferred peptide of the present developments is one that reduces the level of Th40 cells to less than about 50%, less than about 45%, less than about 40%, less than about 35%, less than about 30%, less than about 27%, or equal to about 25% of the total T-cell population. Methods of measuring different types of T-cells in the T-cell population are known to those skilled in the art. Furthermore, a novel method for detecting Th40 cells using peptides of the present developments is disclosed herein.

As used herein, the phrase inflammatory environment refers to the overall population of immune cells, and related immunoregulatory molecules, that are present in a culture of cells, or in the body of an animal. As such, the phrase inflammatory environment encompasses the types, and/or the relative amounts of immune cells and immunoregulatory molecules (e.g., cytokines) present in a culture of cells, or in an animal, which are involved in affecting an inflammatory reaction. Examples of cells encompassed by the term inflammatory environment include, but are not limited to, T cells, neutrophils, macrophages, granulocytes, B cells, and the like. The inflammatory environment relates to cells and molecules that mediate both acute and chronic inflammation. It will be appreciated by those skilled in the art that the inflammatory environment refers to the system to which peptides of the present developments are administered. In one implementation, the system is a cell culture system. In one implementation, the system is a whole animal.

A preferred peptide of the present developments may be one that selectively interacts with a CD40 protein in solution, as determined using an assay such as an immunosorbent assay, or on the surface of a T-cell or other CD40 expressing cells. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one implementation, an assay can be performed using cells in culture, or it can be performed in a whole animal. Assays can be designed to give qualitative, quantitative or semi-quantitative results, depending on how they are used and the type of result that is desired.

One implementation of the present developments is a peptide that interacts with a CD40 protein in such a manner that may affect the interaction of the CD40 protein with a CD154 protein, and may thereby modulate inflammation. The effect of the peptide on the CD40/CD154 interaction can be positive or it can be negative. For example, the peptide can interact with the CD40 protein in such a manner that the strength of the interaction between the CD40 protein and a CD154 protein is increased. Alternatively, the peptide can interact with the CD40 protein such that the strength of the interaction between the CD40 protein and a CD154 protein is decreased. Methods of measuring the strength of binding between the peptide and a CD40 protein are known to those skilled in the art. A preferred peptide of the present developments is one that reduces the strength of the interaction between a CD40 protein and a CD154 protein. Preferred peptides of the present developments reduce the strength of binding between a CD40 protein and a CD154 protein by at least 10%, at least 20%, at least 30%, at least 40%, at least 50%, at least 60%, at least 70%, at least 80%, at least 90%, or at least 95%. A particularly preferred peptide is one that completely inhibits binding of CD40 to CD154. Complete inhibition of binding between CD40 and CD154 means that when a peptide of the present developments is brought into proximity with a CD40 protein and a CD154 protein under conditions that would normally allow the interaction of CD40 and CD154, no such interaction occurs and activation signals are not stimulated in the CD40-expressing cell. Consequently CD40/CD154 mediated modulation of inflammation does not occur. In one implementation, the peptide interacts with the CD40 protein in such a manner as to reduce the level of inflammation in the system. In one implementation, the peptide interacts with the CD40 protein in such a manner as to inhibit the development of inflammation in the system.

While peptides of the present developments can interact with any site on the CD40 protein, preferred peptides of the present developments interact with the CD40 protein at a location that overlaps with the CD154 binding site. In one implementation, a peptide of the present development interacts with the CD40 protein at the CD154 binding site. An example of such a peptide is a CD40 ligand competitive antagonist. As used herein, peptides that interfere with, or inhibit, the binding of a CD154 protein to a CD40 protein are referred to as small interfering peptides (SIPs). As used herein a small interfering peptide is a peptide that, through physio-chemical properties, interferes with the interaction of a CD40 protein with a CD154 protein, thereby preventing activation signals from being delivered to the CD40-bearing cell, thus limiting the activation of the CD40-bearing cell, and consequently, inflammation. As demonstrated herein, the consequences of such interference are prevention of T-cell activation and propagation, and a prevention or reduction of inflammation. Furthermore, one implementation of the present developments may be a peptide that modulates the CD40-CD154 signaling. In this aspect, the peptide may alter or modulate the CD40-CD154 signaling towards a more anti-inflammatory signal.

A peptide useful for practicing methods of the present developments should be of a size sufficient to interact with CD40 protein in such a manner that may modulate inflammation. It is understood by those skilled in the art that preferred peptides are relatively short since they are easier and less expensive to produce. Preferred peptides are those that are less than 20 amino acids in length. A preferred peptide is one that is 6, 13 or 15 amino acids in length. In one implementation, the peptide includes an amino acid sequence selected from the group of SEQ ID NO: 3, SEQ ID NO: 4, SEQ ID NO: 7, SEQ ID NO: 8, and SEQID NO: 9. In another implementation, the peptide includes an amino acid sequence select from the group of SEQ ID NOs: 4, 27, 28, 29, and 30. The sequences of such peptides are shown below in Table 1.

TABLE 1

| SEQ ID NO | SEQUENCE | Description |
|---|---|---|
| 1 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ IAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GFSSFGLLKL | SwissPro 27548.2 Mouse CD40 Ligand (CD154 Protein) |
| 2 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEETKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CD40 Ligand (CD154 Protein) |
| 3 | KGYY | Core-sequence |
| 4 | KKGYYT | 6-mer |
| 5 | AKKGYYTM | 8-mer-mouse |
| 6 | AEKGYYTM | 8-mer human |
| 7 | VLQWAKKGYYTMKSN | 15-mer-mouse |
| 8 | VLQWAEKGYYTMSNN | 15-mer human |
| 9 | NAASVLQWAKKGYYTMKSNLVMLE | 24-mer mouse |
| 10 | ISQAVHAAHAEINEAGR | 15-mer from ovalbumin; control peptide |
| 11 | G-L-Q-W-A-K-K-G-Y-Y-T-M-K-S-N | Gly-1 |
| 12 | V-G-Q-W-A-K-K-G-Y-Y-T-M-K-S-N | Gly-2 |
| 13 | V-L-G-W-A-K-K-G-Y-Y-T-M-K-S-N | Gly-3 |
| 14 | V-L-Q-G-A-K-K-G-Y-Y-T-M-K-S-N | Gly-4 |
| 15 | V-L-Q-W-G-K-K-G-Y-Y-T-M-K-S-N | Gly-5 |
| 16 | V-L-Q-W-A-G-K-G-Y-Y-T-M-K-S-N | Gly-6 |
| 17 | V-L-Q-W-A-K-G-G-Y-Y-T-M-K-S-N | Gly-7 |
| 18 | V-L-Q-W-A-K-K-G-G-Y-T-M-K-S-N | Gly-9 |
| 19 | V-L-Q-W-A-K-K-G-Y-G-T-M-K-S-N | Gly-10 |
| 20 | V-L-Q-W-A-K-K-G-Y-Y-G-M-K-S-N | Gly-11 |
| 21 | V-L-Q-W-A-K-K-G-Y-Y-T-G-K-S-N | Gly-12 |
| 22 | ISQAVHAAHAEINEAGR | 15-mer from ovalbumin; control peptide |
| 23 | YVQGKANLKSKLMYT | Scrambled peptide |
| 24 | WAKKGYYTMK | 10-mer mouse |

TABLE 1-continued

| SEQ ID NO | SEQUENCE | Description |
|---|---|---|
| 25 | VLQWAKKGYYTMK | 13-mer mouse |
| 26 | AASVLQW AKKGYYTMKSNLVMLEN | 24-mer mouse |
| 27 | KGYYTM | 6-mer (Form 2) human |
| 28 | AEKGYY | 6-mer (Form 3) human |
| 29 | AKKGYY | 6-mer (Form 4) mouse |
| 30 | AKGYYT | 6-mer (Form 5) synthetic |
| 31 | YKNVKQMAYWLTGKS | Scrambled peptide |

Interaction of a CD40 protein and a CD154 protein has been shown to occur at particular regions within each protein. Now shown is that, surprisingly, a peptide having only a short portion of the CD154 region that interacts with CD40 is capable of binding to a CD40 protein, thereby modulating inflammation, preventing disease progression, changing cytokine expression, and results that demonstrate the ability to prevent, treat, and/or reduce the effects of inflammatory diseases, including MS. Thus, an implementation of the present developments is a peptide that has at least a portion of the amino acid sequence of a CD154 protein such that the peptide interacts with CD40 protein in such a manner that may modulate inflammation and/or prevent, treat, or reduce the symptoms of MS. In one implementation, interaction of the peptide with CD40 protein results in negative modulation of inflammation. In one aspect, the peptide includes at least a portion of SEQ ID NO: 1 or SEQ ID NO: 2. In a preferred aspect, the peptide is as short as possible yet has enough of the CD154 protein to allow interaction with a CD 40 protein in such a manner that it may modulate inflammation. In one implementation, a peptide of the present developments has 6, 13 or 15 contiguous amino acids from SEQ ID NO: 1 or SEQ ID NO: 2, and interacts with CD40 in such a manner that it may modulate inflammation. A preferred peptide has a core sequence of lysine-glycine-tyrosine-tyrosine (KGYY; SEQ ID NO: 3), which corresponds to amino acids 142-145 of SEQ ID NO: 1 and amino acids 143-146 of SEQ ID NO: 2. Useful peptides can include additional regions of sequence from SEQ ID NO: 1 or SEQ ID NO: 2 that are adjacent to the core sequence, so long as the peptide is capable of modulating inflammation. In one implementation of the present development, a peptide has at least one sequence selected from the group of SEQ ID NO: 3, SEQ ID NO: 4, SEQ ID NO: 8, SEQ ID NO: 8, and SEQ ID NO: 9, so long as the peptide interacts with CD40 protein in such a manner that it may modulate inflammation. In one implementation of the present developments, a peptide includes a sequence selected from the group of SEQ ID NO: 3, SEQ ID NO: 4, SEQ ID NO: 7, SEQ ID NO: 8, and SEQ ID NO: 9. Another implementation of the present development, the peptide includes a sequence selected from the group of SEQ ID NO: 4, SEQ ID NO: 27, SEQ ID NO: 28, SEQ ID NO: 29, and SEQ ID NO: 30.

While peptides of the present development may entirely be of sequences that are responsible for the interaction of the peptide with CD40 protein, they may additionally contain amino acid sequences that do not interact with a CD40 protein, but which have other useful functions. Any useful, additional amino acid sequence can be added to the CD40-interacting sequence, so long as the additional sequences do not have an unwanted effect on the ability of the CD40 interacting sequence to interact with a CD40 protein. For example, in addition to the amino acid sequence responsible for interacting with a CD40 protein, a peptide of the present development can contain amino acid sequences that are useful for visualizing or purifying the peptide. Such sequences act as labels (e.g., enzymes) or tags (antibody binding sites). Examples of such labels and tags include, but are not limited to, B-galactosidase, luciferase, glutathione-s-transferase, thioredoxin, HIS-tags, biotin tags, and fluorescent tags. Other useful sequences for labeling and tagging proteins are known to those of skill in the art.

Likewise, peptides of the present developments can be modified, so long as such modification does not significantly affect the ability of the peptide that it may modulate the interaction between CD40 and CD154 and thus affect inflammation. Such modifications can be made, for example, to increase the stability, solubility or absorbability of the protein. Examples of such modifications include, but are not limited to pegylation, glycosylation, acetylation, amidation, and chemical modification of the peptide. Moreover, these modifications may include PASylation® (PASylation with Pro, Ala and Ser (PAS) sequences) (conjugation of a Pro-Arg-Lys tripeptide to another peptide), the use of polyglycerols, polyoxazolines, poly(amino acids), polyacrylamides, polyvinylpyrrolidones, and polyzwitterons, so long as such changes do not significantly affect the ability of the peptide to provide the therapeutic properties that have been observed.

Peptides of the present developments may be produced in a laboratory (e.g., recombinantly or synthetically). Preferred peptides may be those that are synthesized. Also encompassed are peptides that are combinations of natural and synthetic molecules. General methods for producing and isolating recombinant or synthetic peptides are known to those skilled in the art. It should be noted that, as used herein, an isolated, or biologically pure, molecule, is one that has been removed from its natural milieu. As such the terms isolated, biologically pure, and the like, do not necessarily reflect the extent to which the protein has been purified.

As has been described herein, interaction of the CD40 protein and the CD154 protein are necessary for involvement of Th40 cells in autoimmune inflammation. Consequently, modulation of the interaction between a CD40 and CD154 protein using peptides of the present developments is a useful method of affecting autoimmune inflammation. Thus, one implementation of the present developments is a method to reduce the interaction between a CD40 protein and a CD154 protein including introducing into an environment containing a CD40 protein and a CD154 protein a peptide that interacts with the CD40 protein in such a manner that it may reduce the interaction between the CD40 protein and the CD154 protein. In one aspect of the developments, the peptide reduces the interaction between the CD40 protein and the CD154 protein by at least 5%, at least 10%, at least 20%, at least 30%, at least 40%, at least 50%, at least 60%, at least 70%, at least 80%, at least 90%, or at least 95%. In an implementation, the peptide reduces the interaction between the CD40 protein and the CD154 protein by a factor of at least 10, at least 100, at least 1,000, at least 10,000. Methods of measuring the strength of the interaction between the CD40 protein and the CD154 protein have been discussed previously, and are also know to those of skill in the art.

One implementation of the present developments is a method to modulate inflammation including contacting a CD40 protein with a peptide that interacts to the CD40 protein in such a manner that may modulate inflammation. In one aspect of the developments, interaction of the peptide with the CD40 protein increases the number of Th40 cells by at least 5%, at least 10%, at least 20%, at least 30%, at least 40%, at least 50%, at least 60%, at least 70%, at least 80%, at least 90%, or at least 95%. In one implementation, interaction of the peptide with the CD40 protein increases the number of Th40 cells by a factor of at least 10, at least 100, at least 1,000, at least 10,000. One aspect of the present developments is a method to reduce inflammation in a patient, the method including administering a peptide of the present developments to the patient. In one implementation, the peptide includes an amino acid sequence selected from the group of SEQ ID NO: 3, SEQ ID NO: 4, SEQ ID NO: 7, SEQ ID NO: 8 and SEQ ID NO: 9. In one implementation, the peptide includes an amino acid sequence selected form the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30. In a preferred implementation, interaction of the peptide with the CD40 protein decreases the number of Th40 cells by at least 5%, at least 10%, at least 20%, at least 30%, at least 40%, at least 50%, at least 60%, at least 70%, at least 80%, at least 90%, or at least 95%. In another implementation, interaction of the peptide with the CD40 protein decreases the number of Th40 cells by a factor of at least 10, at least 100, at least 1,000, at least 10,000. In a preferred implementation, the level of Th40 cells is reduced so that Th40 cells have no more than about 20%, about 25%, about 30%, about 35%, or about 40% of the total T-cell population.

Peptides and methods of the present developments are suitable for use in cell culture as well as for treating a patient. As used herein the term patient may refer to any animal in need of such treatment. The animal can be a human or a non-human animal. A preferred animal to treat is a mammal. A peptide can be administered or applied per se, or as pharmaceutical compositions. A peptide of the present developments, or a pharmaceutical composition thereof, can be administered to a patient by a variety of routes, including, but not limited to, by injection (e.g., intravenous, intramuscular, subcutaneous, intrathecal, intraperitoneal), by inhalation, by oral (e.g., in a pill, tablet, capsule, powder, syrup, solution, suspension, thin film, dispersion or emulsion.), transdermal, transmucosal, pulmonary, buccal, intranasal, sublingual, intracerebral, intravaginal, rectal or topical administration or by any other convenient method known to those of skill in the art. A peptide of the present developments, or a pharmaceutical composition thereof, may also include the salt forms of the active compound contemplated by the peptides disclosed herein.

The amount of a peptide of the present development and/or a pharmaceutical composition thereof that will be effective can be determined by standard clinical techniques known in the art. Such an amount is dependent on, among other factors, the patient being treated, including, but not limited to the weight, age, and condition of the patient, the intended effect of the compound, the manner of administration and the judgment of the prescribing physician.

A peptide of the present development, or a pharmaceutical composition thereof, can be administered alone or in combination with one or more other pharmaceutical agents, including other compounds of the present developments. The specific pharmaceutical composition depends on the desired mode of administration, as is well known to the skilled artisan.

Because it has now been found that Th40 cells may be intimately involved in the development of autoimmune diseases, the peptides and methods disclosed herein can be used to affect inflammation resulting from such diseases. Thus, one implementation of the present developments is a method to treat autoimmune disease in a patient, the method including administering to a patient a peptide that interacts with the CD40 protein, thereby reducing inflammation. In one implementation the peptide interacts with the CD40 protein in such a manner as to affect the interaction of CD40 and CD154, thereby reducing inflammation. In one implementation, interaction of the peptide with the CD40 protein may reduce the number of Th40 cells in a patient to a level equal to that observed in subjects that do not have autoimmune disease. The present developments are suitable for treating any patient having an autoimmune disease the development of which is dependent on Th40 cells. More specifically, peptides of the present developments are suitable for reducing the level of Th40 cells in such patients. In a preferred implementation, a peptide of the present developments reduces the level of Th40 cells in a patient suffering from an autoimmune disease to no more than about 25% of the total T-cell population. Examples of such disease included, but are not limited to, asthma, type 1 diabetes; multiple sclerosis; systemic lupus erythematosa; rheumatoid arthritis; Crohn's disease; inflammatory bowel disease; chronic obstructive pulmonary disease (COPD) including types of autoimmune asthma; atherosclerosis; vasculitis; hypertension; thyroiditis including Hashimoto's and Graves diseases; primary biliary cirrhosis; Paget's disease; Addison's disease; acute respiratory distress syndrome, acute lung injury; ACI associated with organ transplantation; hypertension, etc.

One example of a disease that is particularly amenable to treatment using a peptide of the present developments is diabetes. In diabetes, the body's production of, or response to, insulin is impaired. Consequently cells are unable to utilize glucose in the blood, and the levels of this sugar become elevated. Mice are considered diabetic when their blood glucose level is greater than 250 mg/dl for three consecutive days. In humans, a normal, average blood glucose level is 60-110 mg/dl. However diabetics have blood glucose levels of at least 130 mg/dl, and usually much higher. Thus, one implementation of the present development is a method to prevent diabetes in an individual at risk for developing diabetes, the method including administering to the individual a peptide of the present developments. Such risk can result from familial factors (e.g., inheritance) or from other factors, such as the physical condition of the individual. Methods of risk assessment are known to those skilled in the art. In one implementation, the peptide is administered at a time when the individual's blood glucose level is from about 60 mg/dl to about 110 mg/dl. In one implementation, the peptide includes an amino acid sequence selected from the group of SEQ ID NO: 3, SEQ ID NO: 4, SEQ ID NO: 7, SEQ ID NO: 8, and SEQ ID NO: 9, so long as the peptide can down-regulate inflammation. In one implementation, the peptide includes an amino acid sequence selected from the group of SEQ ID NO: 3, SEQ ID NO: 4, SEQ ID NO: 7, SEQ ID NO: 8, SEQ ID NO: 9. In an alternative implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30.

The developments presented herein have also shown that, surprisingly, peptides of the present developments can be used to reverse the disease process in individuals already showing signs of multiple sclerosis. Thus, one aspect of the present developments is a method to slow or abate the progression of, or reverse multiple sclerosis in a patient including administering to a patient diagnosed as having multiple sclerosis, a peptide of the present developments. In one implementation, the peptide includes an amino acid sequence selected from the group of SEQ ID NO: 3, SEQ ID NO: 4, SEQ ID NO: 7, SEQ ID NO: 8, and SEQ ID NO: 9. In one implementation of the developments, the peptide includes an amino acid sequence selected from the group of SEQ ID NO: 3, SEQ ID NO: 4, SEQ ID NO: 7, SEQ ID: 8, SEQ ID NO: 9, SEQ ID NO: 27, SEQ ID NO: 28, SEQ ID NO: 29, and SEQ ID NO: 30, so long as the peptide can down-regulate inflammation. In one implementation, the peptide includes an amino acid sequence selected from the group of SEQ ID NO: 3, SEQ ID NO: 4, SEQ ID NO: 7, SEQ ID NO: 8, and SEQ ID NO: 9. In an alternative implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30. As used herein the phrase to limit progression of or reverse multiple sclerosis means to reduce inflammation and sclerotic regions of an afflicted individual to a level comparable to that observed in a non-diseased individual. During multiple sclerosis, cells of the immune system invade central nervous tissue and establish lesions. The lesions may be small but eventually may disseminate in both time and space—that is—the number of lesions will increase and size of the lesions may increase. Thus, one aspect of the present developments hereof may include a method to slow or abate the number of lesions and the size of the lesions in a patient suffering from MS.

One aspect of the developments hereof may include a method for preventing multiple sclerosis in a subject including administering to the subject in need thereof, a therapeutically effective amount of a peptide that abates the progression of or reverses the symptoms of the disease. Furthermore, one aspect of the developments hereof may further include administering a drug selected from at least one of Aubagio® (teriflunomide), Betaseron® (interferon-b (type 1)), Avonex® (interferon-b-1b), Rebif® (interferon-beta-la), Copaxone® (glatiramer acetate), Tysabri® (natalizumab), Novantrone® (mitoxantrone), Gilenya® (fingolimod), Tecfidera® (dimethyl fumarate), Rituxan® (rituximab), Ocrevus® (ocrelizumab) and Lemtrada® (alemtuzumab).

As has been described, peptides of the present developments may selectively bind to a CD40 expressing cell. Consequently, peptides of the present developments can be used to identify Th40 cells. Thus, one implementation of the present developments is a method to detect Th40, said method including contacting a T-cell population with a peptide of the present developments. In a preferred implementation, the peptide is labeled with a detectable marker, such as, for example, luciferase or alkaline phosphatase. Such detection can be performed using assay techniques known to those skilled in the art. In general, an assay for detecting Th40 cells using a peptide of the present developments includes (a) obtaining a sample of cells; (b) contacting a peptide of the present developments with said cells under conditions suitable to allow binding of the peptide to Th40 cells, if present; (c) washing said cells using conditions that disrupt non-specific interactions, and that remove unbound peptide; and (d) detecting peptide bound to cells. Detection of bound peptide can be achieved directly or indirectly. For example, direct detection can be achieved using a peptide labeled using a detectable marker, as disclosed herein. Following the wash step listed above, the cells are then simply screened for the presence of detectable marker. The presence of detectable marker in the cell sample indicates the presence of Th40 cells. Alternatively, indirect detection involves the use of a second molecule, such as an antibody, that binds to the peptide. In an indirect detection assay, following the wash step listed above, a detection molecule that binds the peptide is added to the cell sample. The detection molecule is labeled with a detectable marker. After washing away unbound detection molecule, the cells are screened for the presence of detectable marker. The presence of detectable marker in the cell sample indicates the presence of Th40 cells. It should be understood that the assays described herein are meant as examples of useful assays, and other assay techniques can be employed. Suitable assay techniques are known to those skilled in the art, and are also disclosed in, for example, Molecular Cloning: A Laboratory Manual, Sambrook, J., Fritsch, E. F., and Maniatis, T, Cold Spring Harbor Laboratory Press; 2nd Edition (December 1989). All referenced cited herein are incorporated herein in their entirety.

The assay technology described above can also be used to identify other molecules that affect the interaction of a CD40 protein with a CD154 protein. Examples of such molecules include, but are not limited to, proteins, peptides and small molecules. For example, assays can be designed that test the ability of molecules to compete with a peptide of the present development for binding to a Th40 cell. For instance, a peptide labeled with a detectable marker, can be mixed with a test molecule and a population of cells known to contain Th40 cells, under conditions that allow binding of the peptide to the Th40 cells. Following an appropriate incubation period, the cells are washed to remove unbound peptide, and the cells screened for the presence of detectable marker. Alternatively, the labeled peptide could be bound to Th40 cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the Th40 cells, while presence of the detectable marker would indicate the test molecule does not inhibit binding of the peptide to Th40 cells. Inhibition of binding need not be 100%, as such assay would also be useful for identifying molecules that partially inhibit binding of the peptide to Th40 cells. It is understood by those skilled in the art that such assays would involve the use of positive controls (e.g., unlabeled peptide) and negative controls (e.g., a protein/molecule that is known not to bind to Th40 cells).

Because increased levels of Th40 cells are associated with the development of autoimmune disease, the present developments can be used to identify patients at risk for developing autoimmune disease. Thus one implementation of the present developments is a method to identify a patient at risk for developing an autoimmune disease. In one implementation, patients at risk for developing an autoimmune disease are identified by obtaining a sample from a patient to be tested, contacting the T-cell portion said sample with a peptide of the present developments, and determining the level of Th40 cells present in the sample, wherein a level of Th40 cells greater than about 25% of the total T-cell population indicates the patient is at risk for developing an autoimmune disease. In one implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30, so long as the peptide binds to the CD40 protein. In one implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30. In a preferred implementation the peptide is labeled with a suitable detectable marker such as, for example, luciferase or alkaline phosphatase.

The present developments also include kits useful for practicing the methods disclose herein. One implementation is a kit for modulating inflammation in an animal or in cells in culture, the kit including a peptide that interacts with a cell in such a manner as to modulate inflammation. In one implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30, so long as the peptide can down-regulate inflammation. In one implementation, the peptide includes an amino acid sequence selected from the group of SEQ ID NO: 3, SEQ ID NO: 4, SEQ ID NO: 7, SEQ ID NO: 8, SEQ ID NO: 9, SEQ ID NO: 27, SEQ ID NO: 28, SEQ ID NO: 29, and SEQ ID NO: 30. Another implementation is a kit for determining the level of Th40 cells, the kit including a peptide that interacts with a CD40 protein, and systems, compositions and/or devices for detecting CD40-bound peptide. Kits can also contain associated reagents and components, such as, but not limited to, buffers, labels, containers, inserts, tubing, vials, syringes, and the like.

Primary progressive MS (PPMS) and secondary progressive MS (SPMS) are two types of MS that may be treated with the methods and peptides hereof. It is estimated that primary progressive MS (PPMS) occurs in approximately 10-20% of individuals, with no remission after the initial symptoms. It is characterized by progression of disability from onset, with little or minor improvements. Secondary progressive MS (SPMS) is estimated to occur in around 65% of those with initial relapsing-remitting MS (RRMS). SPMS usually shows progressive neurological decline between acute attacks without any definite periods of remission. The drug ocrelizumab (Ocrevus®) may be used for the treatment in PPMS and SPMS in patients. Therefore, the peptides of the present developments may be used to reverse the disease process in individuals already showing signs of multiple sclerosis, including PPMS and SPMS. Thus, one aspect of the present developments is a method to slow or abate the progression of, or reverse multiple sclerosis in a patient including administering to a patient diagnosed as having PPMS and SPMS, a peptide of the present developments.

The following examples are provided for the purpose of illustration and are not intended to limit the scope of the claims herein.

EXAMPLES

Example 1

This Example demonstrates the effect of various peptide fragments of CD154 on CD4/CD8 ratios and the development of diabetes in NOD mice.

Figure 2A:
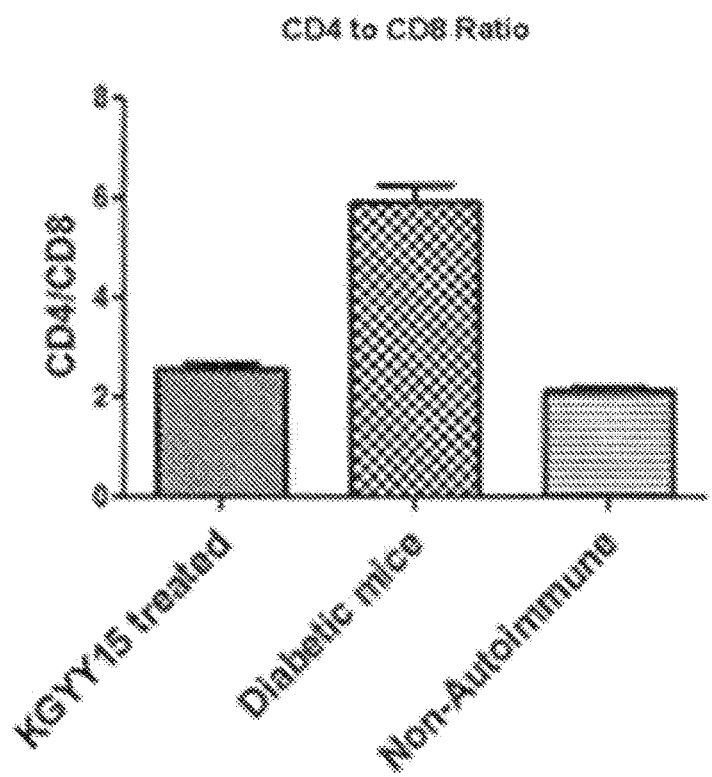
FIG. 2A is a chart of the effect of a 15-mer peptide from CD154 on the CD4/CD8 ratio in NOD mice.
Figure 2B:
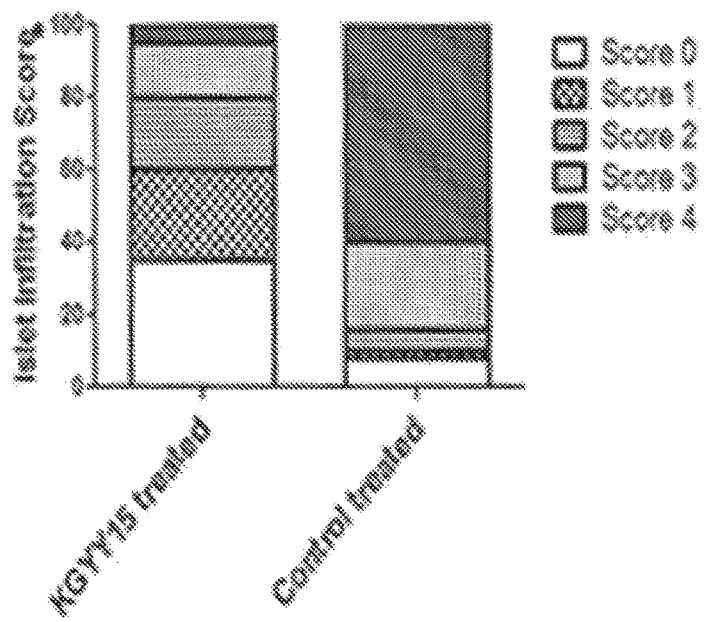
FIG. 2B is a chart of the effect of 15-mer peptide in treated versus control pancreata excised, examined, and scored.

Peptides were designed based on the amino acid sequence of mouse CD154 protein (SEQ ID NO: 1) in the SwissPro database. These pre-designed peptides were then ordered from as made-to-order by New England Peptide. The lyophilized peptides were suspended in phosphate buffered saline at 1 mg/ml. 100 µg of a particular peptide was then injected into the tail vein of 8-9 week old NOD mice. Control mice received 100 µl of phosphate buffered saline. This is well before the onset of diabetes, but after damage to pancreatic islets has begun. Three days after the initial injection, another 100 µg of peptide (or 100 µl of phosphate buffered saline in the case of the Control mice) was injected into the tail vein. Mice were then injected with peptide (or phosphate buffered saline) on a weekly basis. At 10 weeks of age, mice were monitored for diabetes, as indicated by a blood glucose level greater than 250 mg/dL for three consecutive days. The results of this study are shown in FIG. 1. During this time, blood was also taken from the tail vein, or by sub-mandibular venal puncture, and the level of CD4+ and CD8+ cells determined by flow cytometry using antibodies for CD4 protein and CD8 protein. The results of this analysis are shown in FIGS. 2A and 2B.

The results demonstrate that treatment with a scrambled peptide did not reduce the development of diabetes in NOD mice. In contrast, treatment of mice with a 15-mer peptide derived from the CD154 protein prevented the onset of diabetes. Further, both the 6-mer and 10-mer peptides derived from the CD154 protein had significant effects on the development of diabetes. In addition, the data demonstrate that the 15-mer peptide did not result in compromise of the immune system, as determined by the CD4/CD8 ratio.

Example 2

This Example demonstrates the effect of the 15-mer peptide on hyperglycemia in newly diabetic NOD mice.

Figure 3:
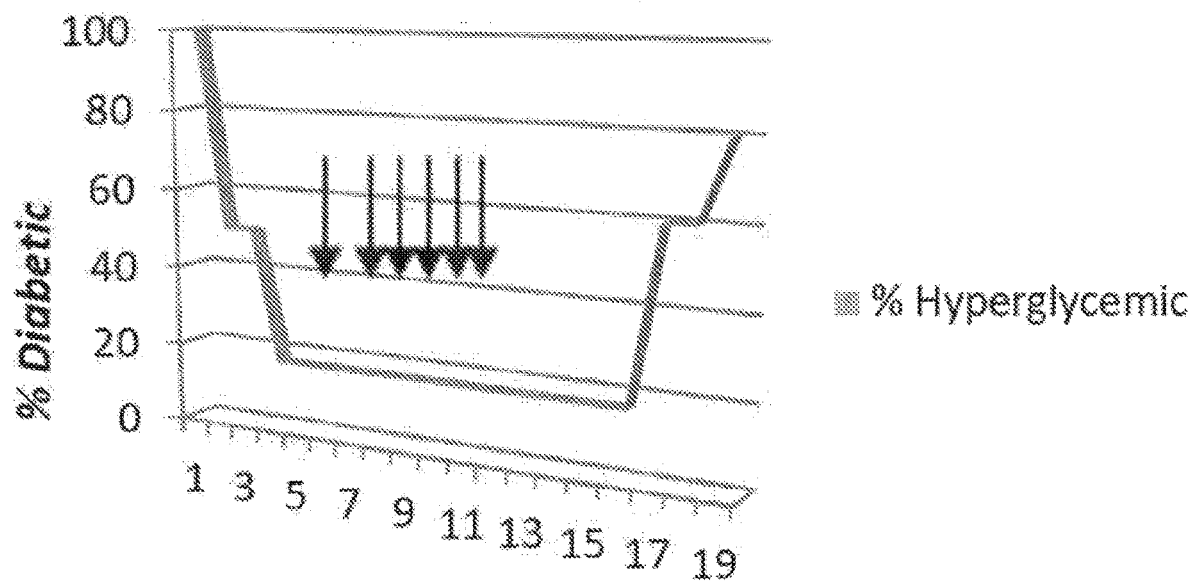
FIG. 3 is a graph of reversal of diabetes in NOD mice using a 15-mer peptide from CD154.

Six untreated mice that developed diabetes, were injected intravenously with 100 µg of the 15-mer peptide. These mice were then given weekly injections of the 15-mer peptide into their tail veins, and their blood glucose levels monitored twice-weekly. The 15-mer peptide was administered for a total of ten weeks, after which the treatment was stopped. The results of this study are shown in FIG. 3.

This study demonstrates that injection of the 15-mer peptide into already diabetic mice can reverse hyperglycemia. It also demonstrates that cessation of the treatment results in return of hyperglycemia within 7 weeks.

Example 3

This study demonstrates the ability of the 15-mer peptide to bind to Th40 cell and B cells.

Figure 4:
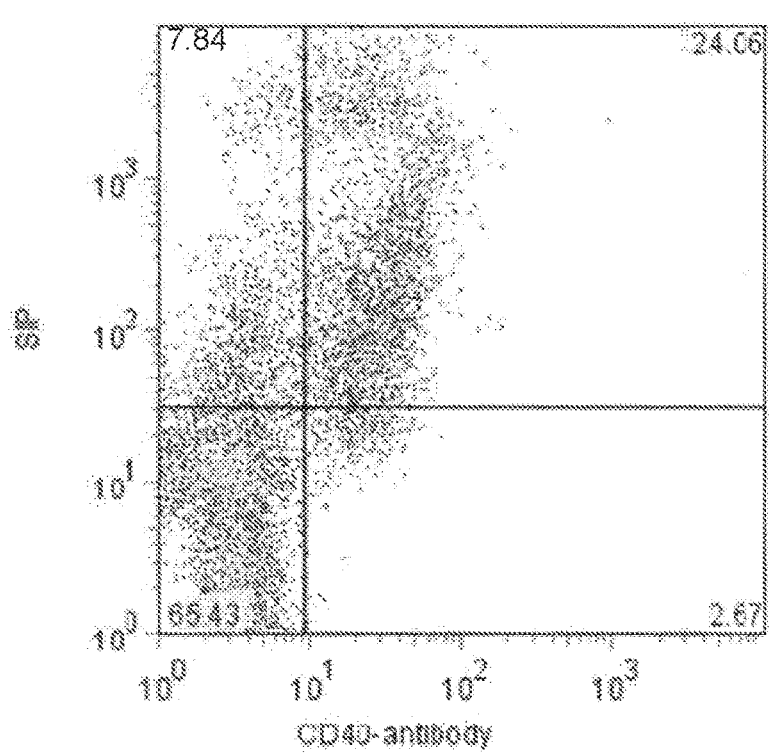
FIG. 4 is a dot-plot of the detection of Th40 cells using a 15-mer peptide from CD154.

Total lymphocytes were isolated from 9 week old NOD mice. The lymphocytes were incubated with anti-CD4, anti-CD8, and an FITC-labeled 15-mer peptide, and then analyzed by flow cytometry. Cells were gated for CD4 (both CD4hi and CD4lo populations were included) and CD4 versus the 15-mer peptide (small interfering peptide or "SIP"). The results of this analysis are shown in FIG. 4.

Figure 5:
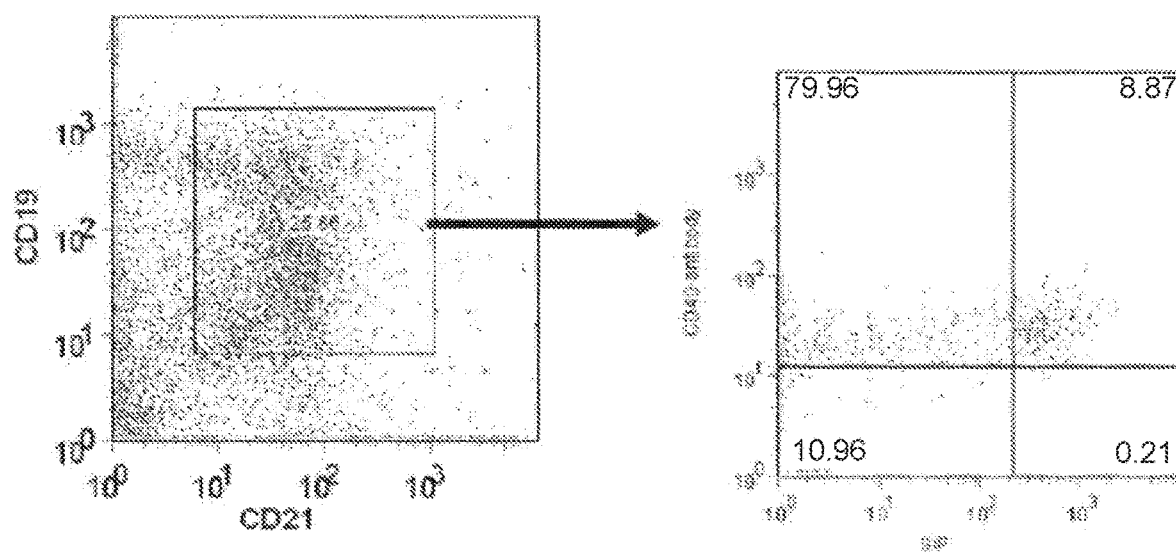
FIG. 5 is a dot-plot of a screening of B cells using a 15-mer peptide from CD154.

B cells were isolated from the spleens of NOD mice. Sorted MHC-II+ cells were purified from total lymphocytes. Cells were stained with FITC-labeled 15-mer peptide (SIP), anti-CD40, and B cell markers CD19 and CD21. MHC-II+ cells were gated for CD19+ and CD21+ and then 15-mer peptide (SIP) versus CD40 antibody was measured. The results of this study are shown in FIG. 5.

This study shows that a substantial majority, 90% of CD40+ T-cells, also bind the 15-mer peptide, thereby demonstrating that the 15-mer peptide is highly specific for CD40+ cells. It also shows that while 90% of B cells were CD40 positive, only 8% of B cells bound the 15-mer peptide.

Example 4

This example demonstrates the level of CD40 positive cells in the blood of type-I diabetic subjects and non-diabetic (control) subjects. Diabetic sample is the left bar on the graph and the right bar is non-diabetic.

Figure 6:
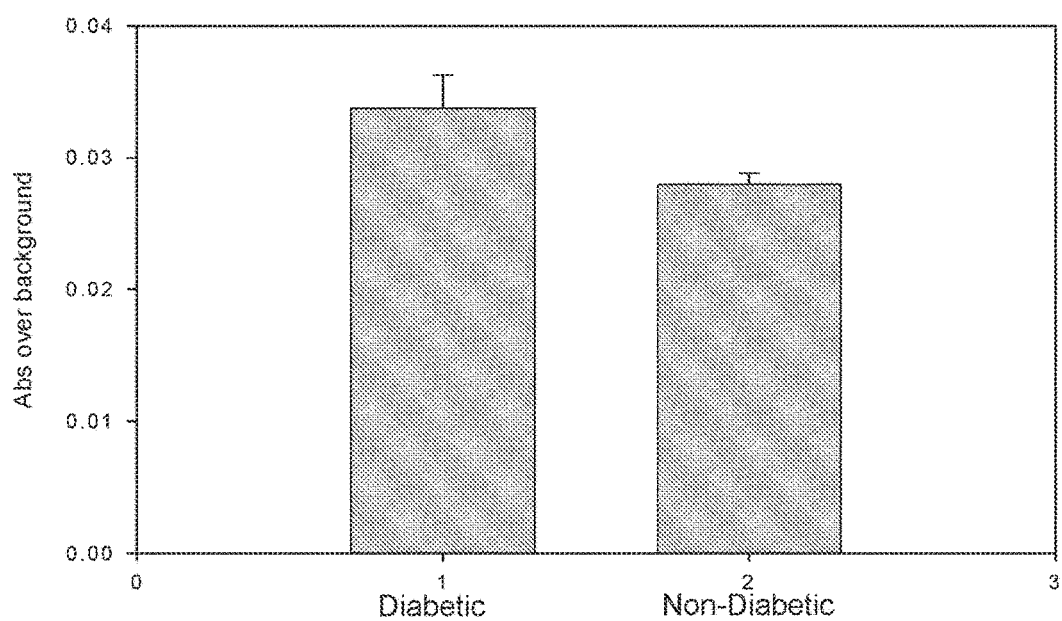
FIG. 6 is a chart demonstrating a comparison of Th40 cell levels in diabetic and non-diabetic mice.

One ml of whole blood was obtained from each individual and incubated with biotin-conjugated, 15-mer peptide. The cells were then exposed to horse radish peroxidase (HRP)-avidin, washed and the absorbance at 405 nm determined using a spectrophotometer. The results of this study are shown in FIG. 6.

This study demonstrates that blood cells from patients having type-I diabetes had higher 15-mer peptide binding activity than cells from non-diabetic controls.

Example 5

This example demonstrates the level of insulin granulation observed in the pancreas of NOD mice treated with either the 15-mer peptide or a peptide from ovalbumin.

Figure 7:
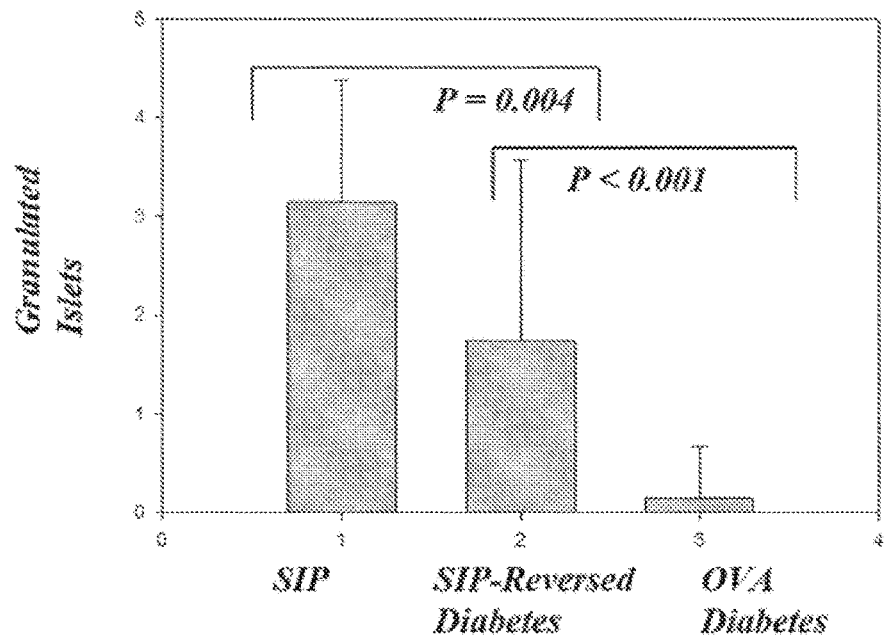
FIG. 7 is a chart demonstrating the effect of treatment with the 15-mer peptide on insulin granulation of the pancreas.
Figure 8:
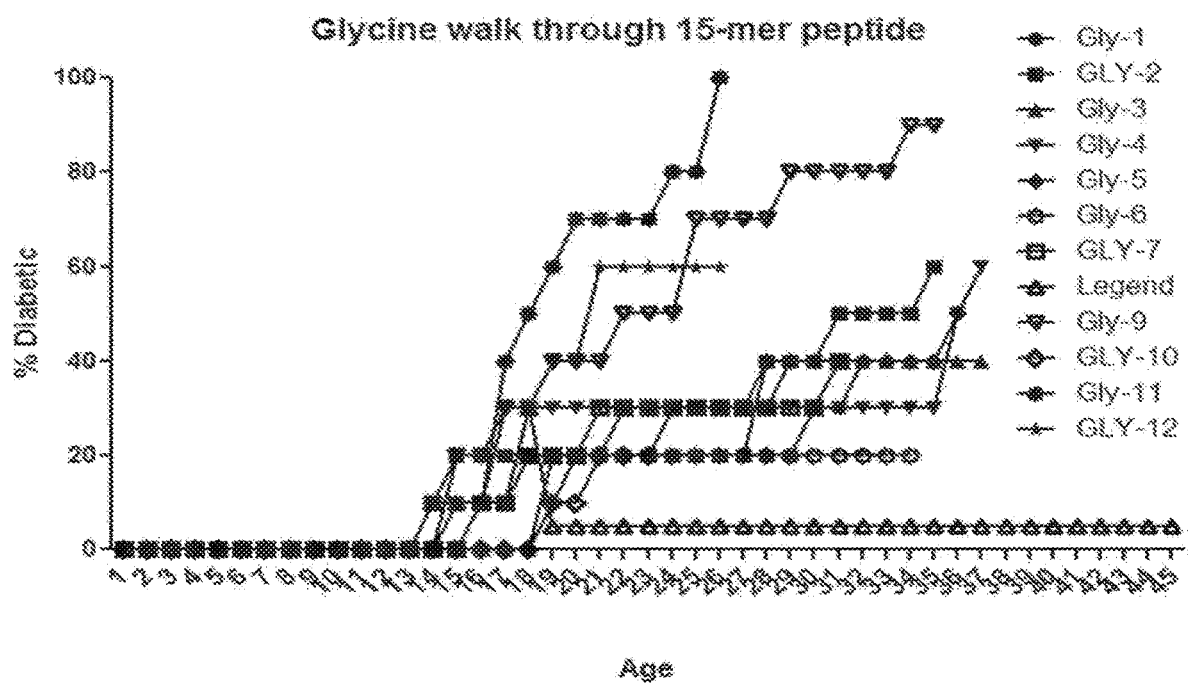
FIG. 8 is a graph that shows the effect of mutations in the 15-mer peptide on the ability of the 15-mer peptide to inhibit development of diabetes in NOD mice.

At the onset of diabetes, six NOD mice were injected with 100 μg of the 15-mer peptide (SEQ ID NO: 7), resulting in the reversal of hyperglycemia in 80% of the recipients. Six weeks after reversal of hyperglycemia, mice were sacrificed and the pancreas removed for analysis. The pancreas was fixed, sectioned and then stained using an aldehyde/fuschsin stain that allows detection of insulin granules. Granulation of the tissue was scored as follows: 4=completely granulated; 3=75% of islet granulated; 2=50% of islet granulated, and peri-insulitis; 1=25% of islet granulated; 0=no insulin granules detected. The results of this analysis are shown in FIG. 7.

This analysis demonstrates that the 15-mer peptide preserved insulin granules in the majority of the mice, and was significantly improved in peptide-reversed diabetic mice compared to diabetic mice that received an irrelevant peptide.

Example 6

This example demonstrates the effect of mutations in the 15-mer peptide on its ability to prevent the onset of diabetes.

Peptide were designed and produced as described in Example 1. Variant peptides were produced so that in each variant, a glycine was substituted for an amino acid corresponding to an amino acid in positions 1-7 or 9-12 of SEQ ID NO: 7, as follows:

| | | |
|---|---|---|
| Gly-1 | G-L-Q-W-A-K-K-G-Y-Y-T-M-K-S-N | (SEQ ID NO: 11) |
| Gly-2 | V-G-Q-W-A-K-K-G-Y-Y-T-M-K-S-N | (SEQ ID NO: 12) |
| Gly-3 | V-L-G-W-A-K-K-G-Y-Y-T-M-K-S-N | (SEQ ID NO: 13) |
| Gly-4 | V-L-Q-G-A-K-K-G-Y-Y-T-M-K-S-N | (SEQ ID NO: 14) |
| Gly-5 | V-L-Q-W-G-K-K-G-Y-Y-T-M-K-S-N | (SEQ ID NO: 15) |
| Gly-6 | V-L-Q-W-A-G-K-G-Y-Y-T-M-K-S-N | (SEQ ID NO: 16) |
| Gly-7 | V-L-Q-W-A-K-G-G-Y-Y-T-M-K-S-N | (SEQ ID NO: 17) |
| Gly-9 | V-L-Q-W-A-K-K-G-G-Y-T-M-K-S-N | (SEQ ID NO: 18) |
| Gly-10 | V-L-Q-W-A-K-K-G-Y-G-T-M-K-S-N | (SEQ ID NO: 19) |
| Gly-11 | V-L-Q-W-A-K-K-G-Y-Y-G-M-K-S-N | (SEQ ID NO: 20) |
| Gly-12 | V-L-Q-W-A-K-K-G-Y-Y-T-G-K-S-N | (SEQ ID NO: 21) |

NOD mice were placed in groups of 10, and the mice in each group injected IV weekly with 25 μg of either wild-type (WT; Legend) peptide or a variant peptide (in PBS, ph 7.2) listed above. The development of diabetes was monitored by measuring blood glucose levels on a weekly basis. Mice were considered "diabetic" when blood glucose was 250 mg/dl or greater for 2 consecutive readings. Injections began at 6 weeks of age=pre-diabetes.

This example demonstrates that substitution of a glycine at any of positions 1-7, or 9-12, reduces the ability of the 15-mer peptide to inhibit the development of diabetes. It also shows that such mutations do not completely abolish the ability of the mutated 15-mer peptide to inhibit the development of diabetes. FIG. 9 provides for different varieties of the SIP peptide, the length of the peptide, the sequence of the peptide, and the predicted stability of the peptide. FIG. 10 provides a comparison of the sequence of the mouse and human versions of the peptide.

Example 7

Figure 11:
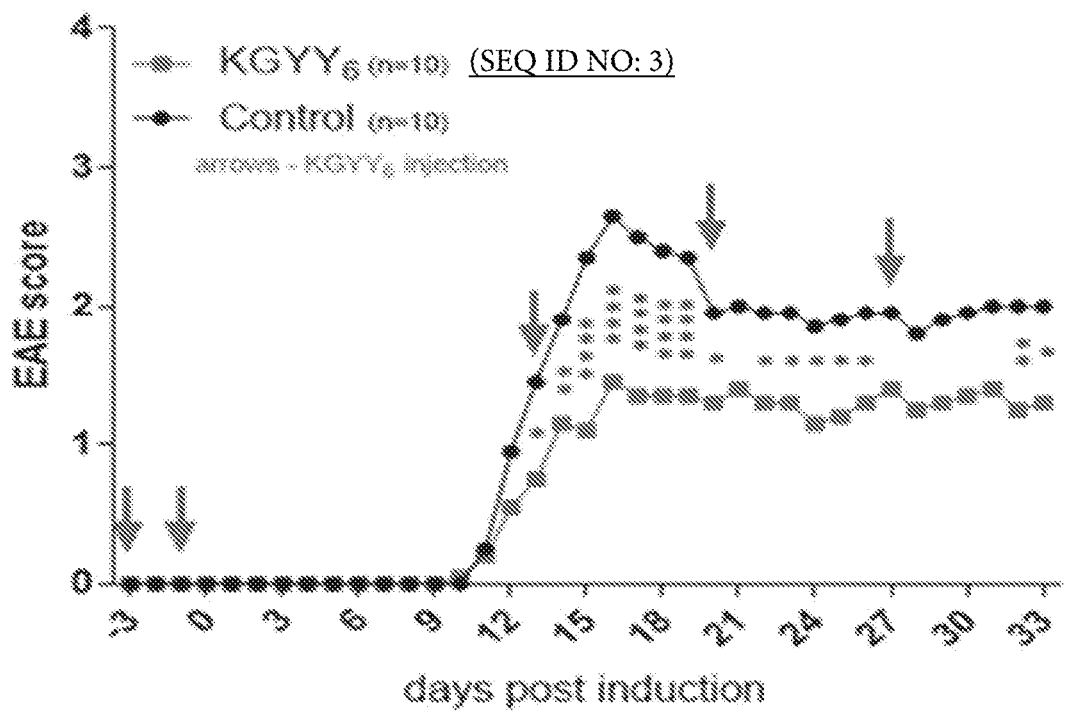
FIG. 11 is a graph that demonstrates that the administration of $KGYY_6$ may ameliorate EAE.

One group of mice—C57BL/6 mice from Taconic (Hudson, N.Y., USA) received KGYY$_6$ (SEQ ID NO: 29) intravenous (IV) injections 3 days and 1 day prior to EAE induction, while another control group received a vehicle of phosphate buffered saline (PBS). EAE was then induced and the mice started to show symptoms on day 10, which is standard for these mice under these conditions. This is further depicted in FIG. 11. On days 13, 20, and 27, the KGYY$_6$ group of mice receive a boost of peptide, while the other group again received PBS via IV injection. The disease course was significantly less severe in the KGYY$_6$ treated group compared to the control group (see FIG. 11, p<0.0001; two-way ANOVA (Analysis of Variance)). By day 13, there was a statistically significant difference that lasted throughout the experiment. In FIG. 11—*—asterisks—denote p-value: *—one asterisk is <0.05; —two asterisks is <0.01; *—three asterisks is <0.001; and ****—four asterisks is <0.0001. This is a two-way ANOVA with Sidak's multiple comparisons test. Arrows in above lines in FIG. 11 represent days −3, −1, 13, 20, and 27, which correspond to days on which the mice received the KGYY$_6$. Mice were disease scored daily in this study as described in more detail below.

The EAE mouse model can be highly variable even when attempting to control all possible parameters. This variability in EAE may be due to seasonal variations as well as litter differences in the mice. In order to minimize litter-to-litter and seasonal variations, experiments and studies were performed that had 10 mice per group and the mice were randomly mixed once they arrived from the vendor. Female 10-12 week old C57BL/6 mice were immunized subcutaneously on the upper back/neck with 100 μl completely emulsified MOG$_{35-55}$ peptide (50 μg in 50 μl PBS) and complete Freund's adjuvant (CFA; 75 μg M. Tuberculosis H37 RA (Becton Dickinson and Company (Franklin Lake, N.J., USA)) in 50 μl incomplete Freund's adjuvant (mineral oil)), followed by i.p. pertussis toxin (PT; 200 ng (Sigma-Aldrich® (St. Louis, Mo., USA)) in 100 μl PBS) injections. Mice were then randomly assigned to a treatment cohort or vehicle control cohort. One cohort of mice received intravenous injections of the KGYY$_6$ (SEQ ID NO: 29)–25 μg in 100 μl PBS per mouse on days −3, −1, 13, 20, and 27 as described above. Day 0 is the reference starting point for EAE induction. Another cohort received peptide on days −3, −1, 6, 11, 13, and 15. Vehicle control mice received injections of PBS.

All mice were monitored daily for disease and scored in the following manner: 0—no abnormalities; 0.5—clutching hind limbs; 1— limp tail or weak hind limbs and/or wobbly gait; 1.5—limp tail and clutching hind limbs; 2— limp tail and weak hind limbs and/or wobbly gait wherein the mouse supports itself and propels itself using hind limbs; 2.5—limp tail and weak hind limbs and/or wobbly gait wherein the mouse cannot support and propel itself using hind limbs, but the paws are moving. 3—limp tail and one weak hind limb, while the other hind limb is completely paralyzed wherein the mouse uses the weak hind limb to propel itself in some fashion. 3.5—limp tail and one weak hind limb, while the other hind limb is completely paralyzed where in the mouse does not use the weak hind limb, which is almost at paralysis. 4—limp tail and complete hind limb paralysis wherein the mouse often displays spastic hypertonia and involuntarily crosses its hind limbs. 5— complete paralysis of hind quarter and weak forelimb(s). The data are reported as the mean daily clinical score for all animals in each group. Mice reaching a level 5 or losing more than 20% of their bodyweight are euthanized.

Figure 12:
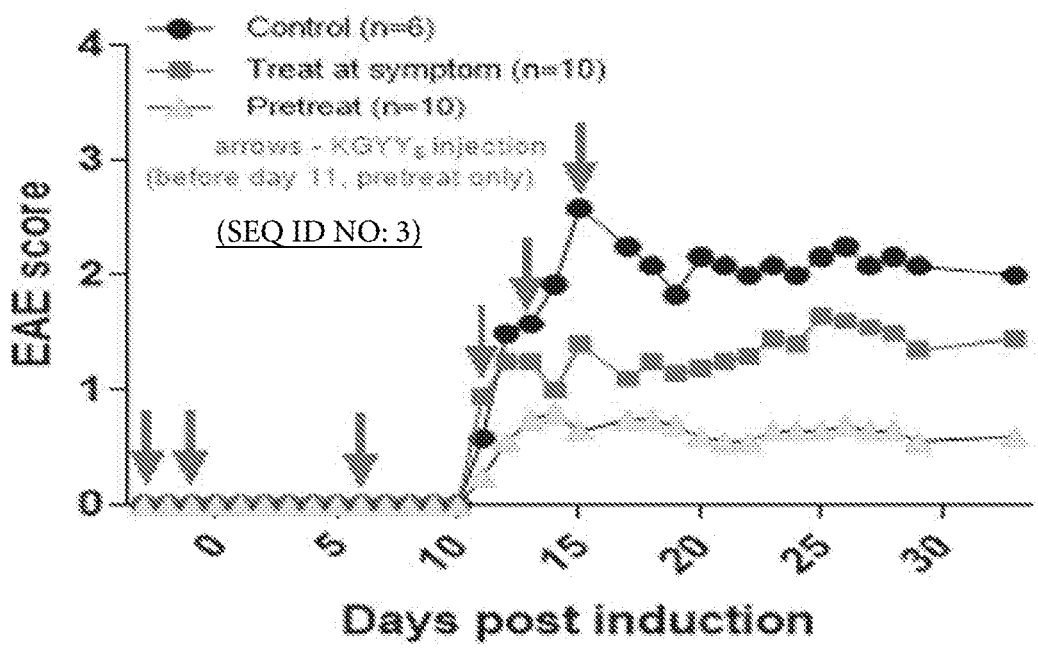
FIG. 12 is a graph that demonstrates that pre-treatment with $KGYY_6$ may result in better amelioration of EAE than starting treatment at first symptom.
Figure 13:
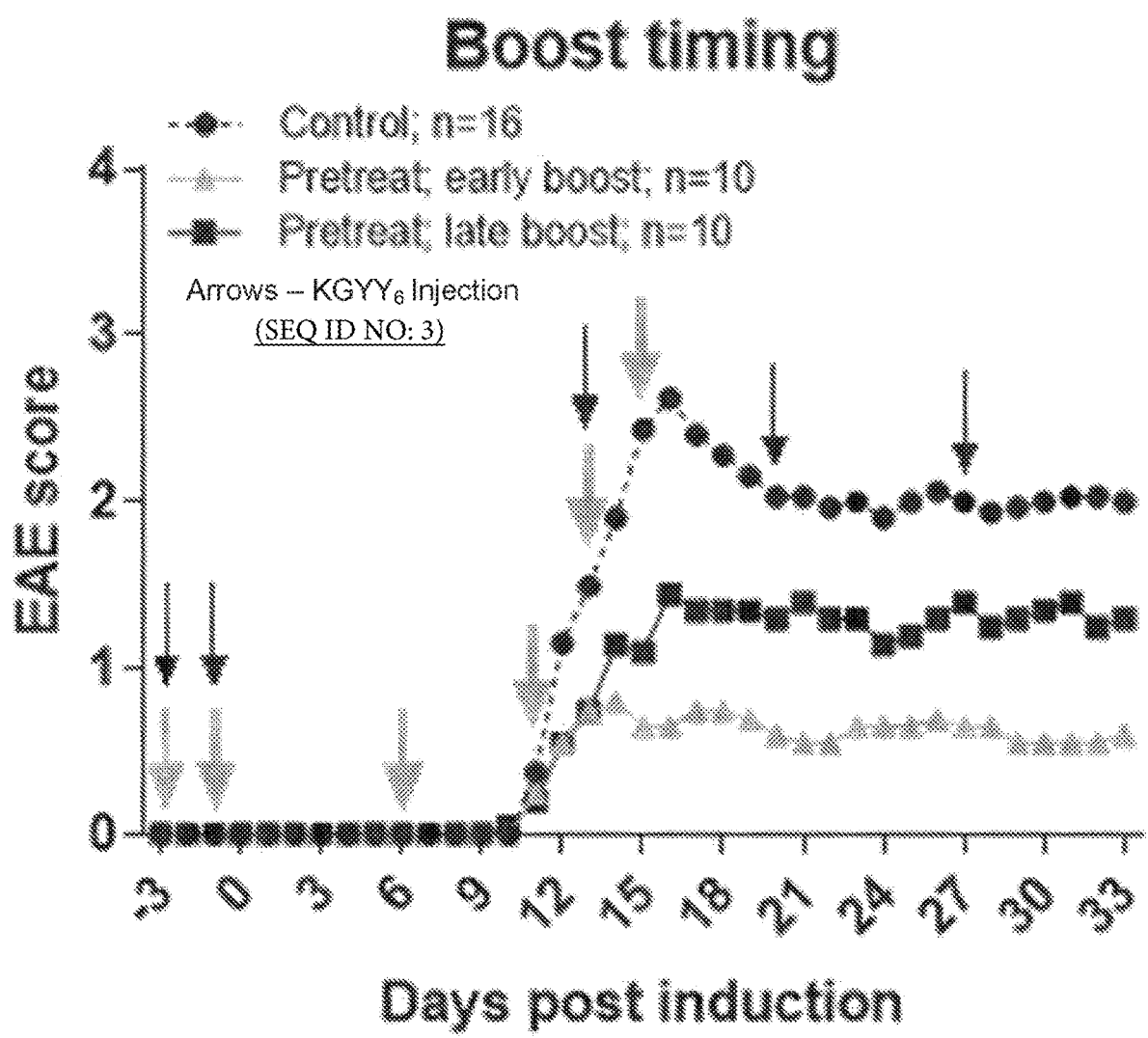
FIG. 13 is graph comparing pre-treated mice and the effect of early and later boosts on the progression of EAE.

The results of this study are shown in FIGS. 12 and 13, demonstrate that the administration of KGYY$_6$ may ameliorate EAE, and that earlier boosts of the peptide may have a greater impact.

Example 8

This study demonstrates that starting treatments at early signs of EAE may ameliorate symptoms in the EAE mouse model. For this study, a group of EAE induced mice were treated with KGYY$_6$ via intravenous (IV) injections on days 11, 13, and 15. Another group of mice were pretreated on days −3 and −1, and received further treatments on days 6, 11, 13, and 15. Another group of mice served as control for disease induction and received no treatments.

The control group demonstrated a disease course identical to the previous experiment (as in Example 7, above), while the pretreated mice, again, had a significantly less severe disease course (see FIG. 12, p<0.0001; Two-way ANOVA with Tukey's multiple comparison test). The treat-at-symptom group also demonstrated a less severe disease course compared to control but was more severe than the pretreated group (see FIG. 12, p<0.0001 for both comparisons; two-way ANOVA with Tukey's multiple comparison test).

FIG. 12 is a graph that demonstrates that starting treatment at the first symptoms may ameliorate EAE. In this example C57BL/6 mice were either pretreated at days −3 and −1, or not, with KGYY$_6$ peptide. Then EAE was induced. Mice pretreated with KGYY$_6$ received boosters on days 6, 11, 13, and 15, as indicated by the arrows in FIG. 12. Another group, that was not pretreated, received the KGYY$_6$ peptide as first symptoms appeared on day 11, and received boosters on days 13 and 15. Mice were disease scored daily using the same methodology as described in Example 7. Results are displayed in FIG. 12. The line with solid circles represents the control group EAE score. The line with solid squares represents the EAE score of the group treated at first sign of symptoms. The line with the solid triangles represents the EAE score of the group that was pretreated as described above.

Example 9

This study demonstrates that earlier treatment with KGYY$_6$ may have an increased impact on the EAE disease course. The disease course in the pretreated group in FIG. 11 appeared to be more severe than the disease course of the pretreated group in FIG. 12. The difference between these two studies was the timing of the peptide boosts that were administered after the initial pre-treatment at days −3 and −1. The disease courses of the groups with different boost schedules were compared and this data demonstrated that there was a significant difference in disease severity, with overall less severe disease if the boosts started early, at 6 days, rather than at 13 days. (See FIG. 13, p<0.0001; Two-way ANOVA with Tukey's multiple comparison test).

FIG. 13 is a graph that demonstrates that earlier boosts with KGYY$_6$ may have an increased impact on the EAE disease course. In this study, C57BL/6 mice were either pretreated, or not, with KGYY$_6$ peptide and then EAE was induced. KGYY$_6$ pretreated mice received boosters of KGYY$_6$ on days 6, 11, 13, 15. Another group of pretreated mice received boosters of KGYY$_6$ on 13, 20, and 27. Mice were disease scored daily. The results are presented in FIG. 13.

Example 10

This study examined T cells from KGYY$_6$ treated mice regarding expression of CD69 levels.

CD69 expression traditionally is described as an early or very early activation marker on T cells and is induced by TCR recognition of antigen and subsequent CD3 stimulation. (Miller, S. D., et al., Current Protocols in Immunology, 15.1.1-15.1.20, 2010). However, studies that are more recent have focused on the function of the molecule. CD69 is a membrane-bound, type II, C-lectin receptor that interacts with galectin-1 as a trans-ligand, and interacts with sphingosine-1-phospate receptor (S1P1R) as a cis-ligand. (Miller, S. D., et al., Current Protocols in Immunology, 15.1.1-

15.1.20, 2010). S1P1 promotes egress of T cells from lymph nodes and from tissues and CD69 interaction with S1P1R prolongs tissue retention. (Cibrián, D., et al. Eur. J. of Immunol. 47(6):946, 2017). This is particularly relevant given that S1P1R super-agonist, Gilenya®, is one of the disease modulating therapies that is FDA approved for MS. (Mackay, L. K., et al., J. Immunol. 194(5):2059, 2015). Gilenya's® mechanism of action is to bind S1P1R and to down regulate its surface expression, which then retards T cells in lymph nodes. Based on this information, CD69 expression on cells from lymph nodes may indicate cells poised for nodal retention.

Figure 14A:
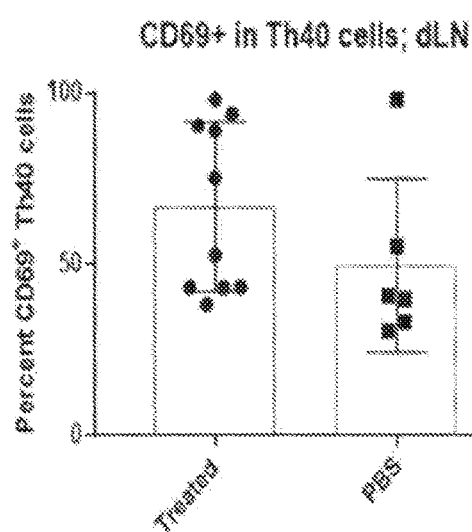
FIG. 14A, FIG. 14B, FIG. 14C and FIG. 14D are charts comparing CD69 percentage levels in Th40 and CD4 samples from draining Lymph Nodes (dLN) and spleens of treated and non-treated subjects.
Figure 14B:
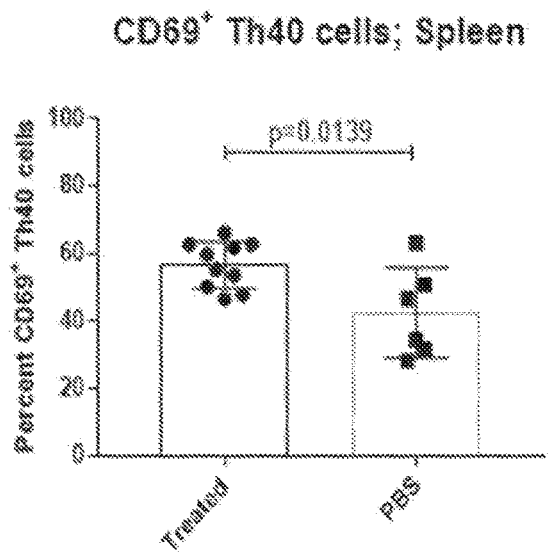
Figure 14C:
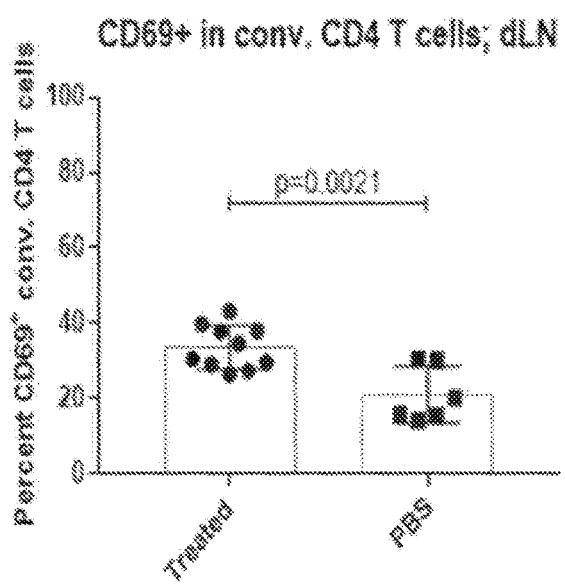
Figure 14D:
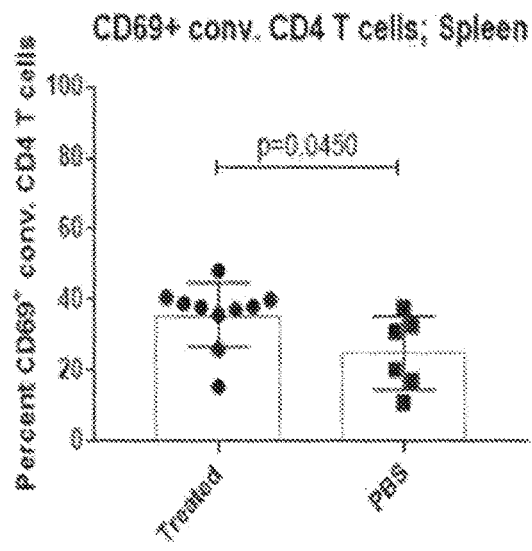
Figure 15A:
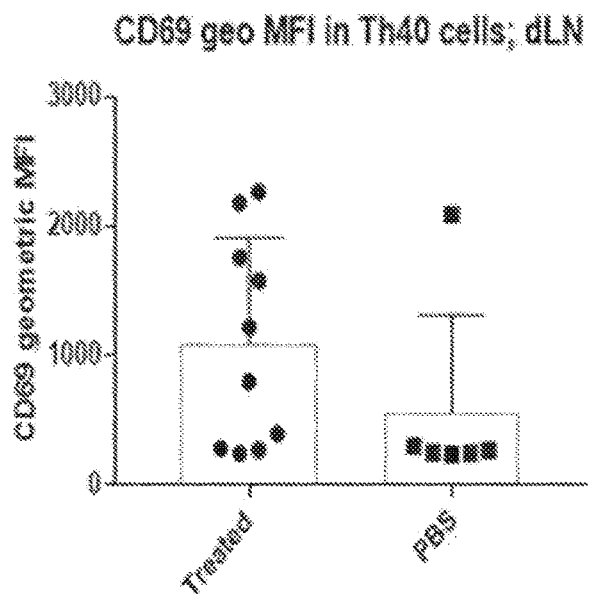
FIG. 15A, FIG. 15B, FIG. 15C and FIG. 15D are charts demonstrating CD69 levels on a per cell basis in T cells from $KGYY_6$ treated mice compared to non-treated.
Figure 15B:
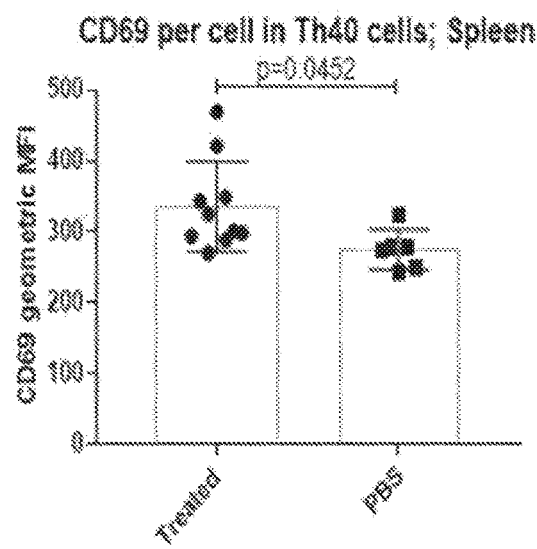
Figure 15C:
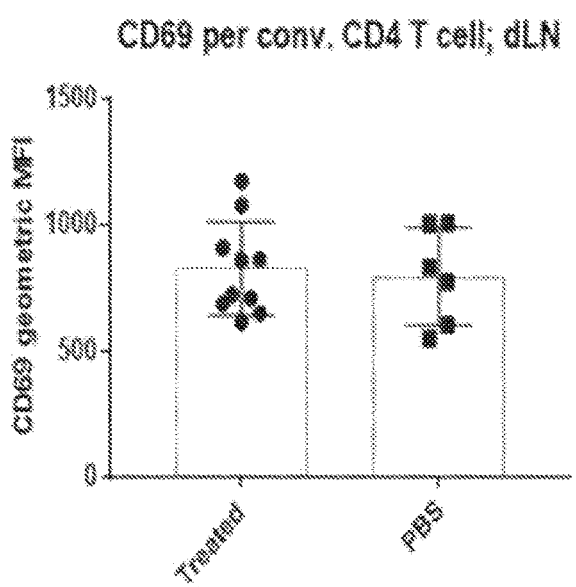
Figure 15D:
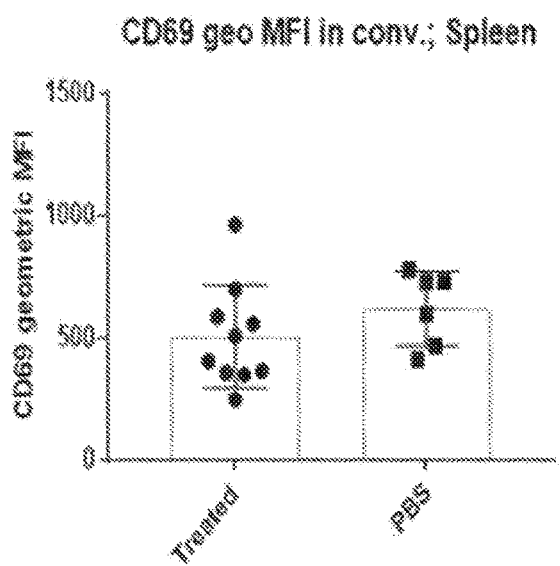
Figure 16A:
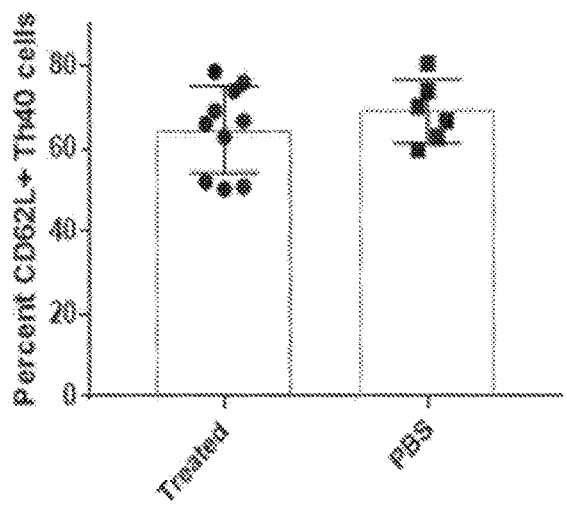
FIG. 16A, FIG. 16B, FIG. 16C and FIG. 16D are charts showing the level of CD62L expressing cells in treated and untreated subjects.
Figure 16B:
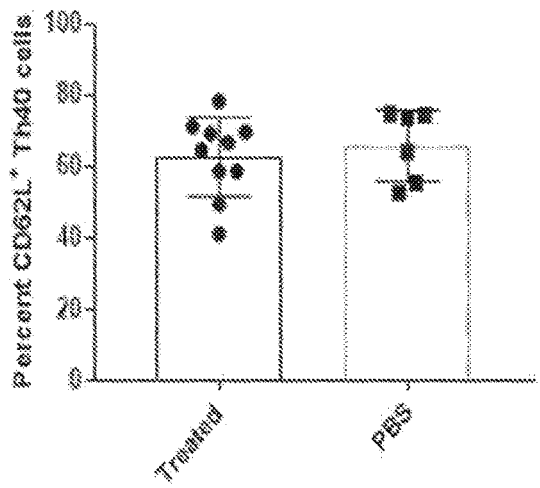
Figure 16C:
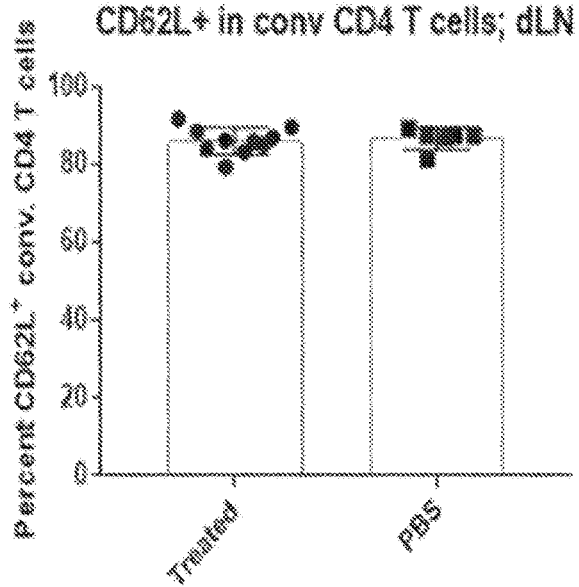
Figure 16D:
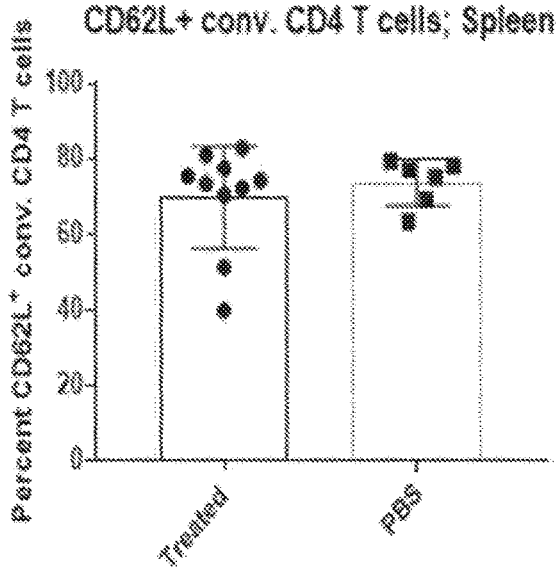

In this study, the number of CD69 expressing cells were measured and determined in draining lymph nodes (dLN) and spleens harvested from EAE mice at the end of the studies as described in Examples 7, 8, and 9 and the administration of $KGYY_6$, after 33 days. The number of Th40 cells in dLN of treated mice expressing CD69 was increased when compared to vehicle treated controls as demonstrated in FIG. 14A. A significantly greater number of Th40 cells from spleens of $KGYY_6$ treated mice expressed CD69 compared to untreated mice, as in FIG. 14B. FIG. 14B demonstrates this with a p=0.0139 using a t-test. Overall, fewer of the conventional CD4 T cells from dLN and spleen expressed CD69 compared to Th40 cells (compare FIGS. 14A, B, C, and D); however, the number of conventional CD4 T cells expressing CD69 was increased by $KGYY_6$ treatment compared to the same cells from controls. This is demonstrated by FIG. 14 C and FIG. 14D, wherein the p=0.0450 in spleen and p=0.0021 in dLN comparison using a t-test.

CD69 expression on a per cell basis was measured and it was found that in Th40 cells there was an increase in the amount of CD69 expressed per cell as in FIGS. 15A, 15B, 15C and 15D. Th40 cells from spleens of treated mice expressed significantly more CD69 per cell than the same cells from vehicle controls (see FIG. 15B, p=0.0452, t-test). While the percentage of CD4 T cells that expressed CD69 was increased by $KGYY_6$ treatment, that treatment did no change the amount of CD69 per cell, in this cell type.

FIGS. 14A-D and 15A-D demonstrate that T cells from $KGYY_6$ treated mice express more CD69. Lymphocytes from dLN or spleen were stained and gated on the Th40 or conventional CD4 T cells then CD69 expression was analyzed. Significance was calculated by t-test and p-values are indicated in the figures and described above.

Example 11

This study examined T cells from $KGYY_6$ treated mice regarding expression of CD62L.

L-selectins are expressed on T cells and, depending upon activation status, expression rapidly cycles between high and low levels, thus allowing cells to crawl to areas of inflammation, and to extravasate into the tissue. (Mao-Draayer, Y., et al., Clinical Immunol. 175:10-5, 2017; Butcher, E. C., et al., Science, 272(5258):60-6, 1997). CD62L is an L-selectin that has generally been associated with naïve T cells, given its importance in lymph node retention. (Chao, C. C., et al., J. Immunol., 159:1686, 1997; Tedder, T. F., et al., Behring Inst. Mitt., 92:165, 1993). Rather than considering CD62L as a biomarker for naïve T cells, it may be possible that CD62L may be involved in lymph node retention of potentially pathogenic effector cells. The number of CD62L expressing Th40 and conventional CD4 T cells from both spleens and dLN of $KGYY_6$ treated mice were compared to mice treated with vehicle (PBS) only (the control). There was no difference in number of CD62L expressing cells between treated and untreated as demonstrated in FIGS. 16A, 16B, 16C and 16D.

Example 12

This study demonstrates that $KGYY_6$ treatment alters IL-10 production by conventional CD4 T cells.

Figure 17A:
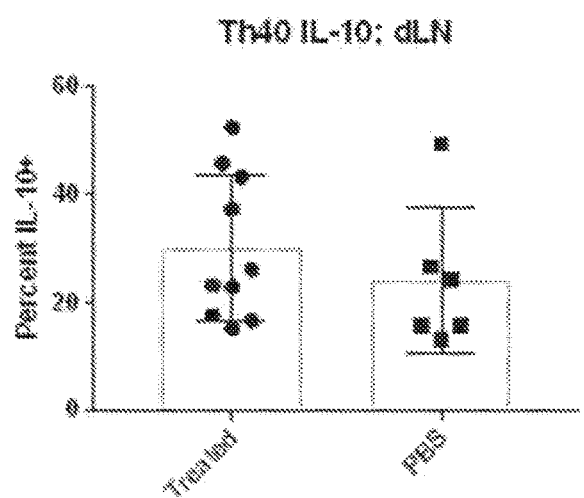
FIG. 17A, FIG. 17B, FIG. 17C and FIG. 17D demonstrate the effect that administration of the $KGYY_6$ had on IL-10 levels in Th40 cells and conventional CD4 T cells from the dLN and spleen of treated and untreated mice.
Figure 17B:
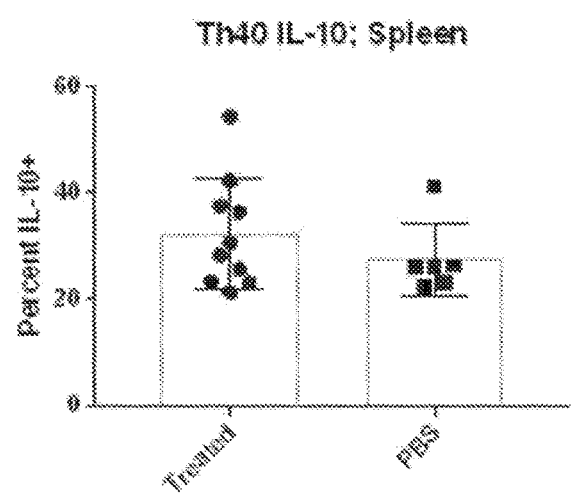

Intracellular cytokine expression profiles in Th40 and conventional CD4 T cells were examined immediately ex-vivo after 33 days and at the end of the study as described in Example 7. In conventional CD4 T cells from dLN, but not spleen, of $KGYY_6$ treated mice, there was an increase in intracellular IL-10 (interleukin-10) compared to the same cells from untreated mice. This is demonstrated in FIG. 17C. In Th40 cells, there was no difference in intracellular IL-10 expression between $KGYY_6$ treated and untreated mice in dLN or spleen, as demonstrated in FIGS. 17A and 17B.

Figure 17C:
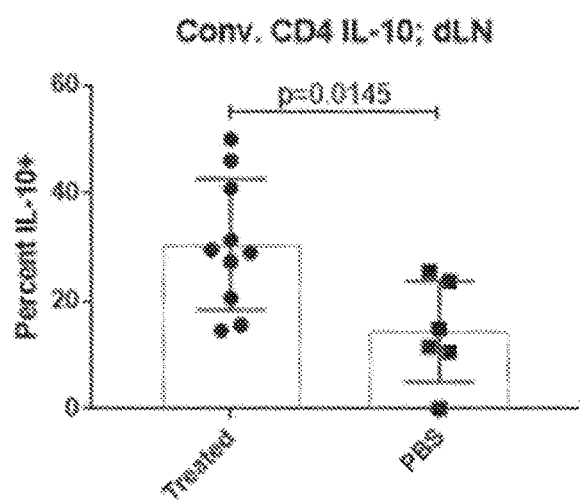
Figure 17D:
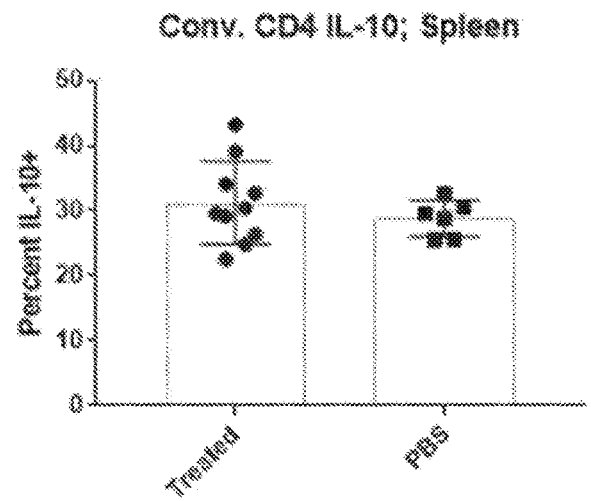
Figure 18A:
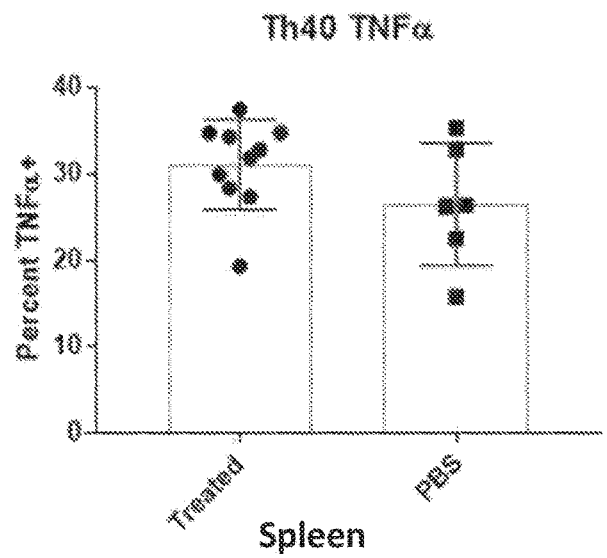
FIG. 18A, FIG. 18B, FIG. 18C and FIG. 18D are charts demonstrating the levels of TNFα, IFNγ, IL-2, and IL-17A in Th40 cells from spleen of $KGYY_6$ treated and untreated mice.
Figure 18B:
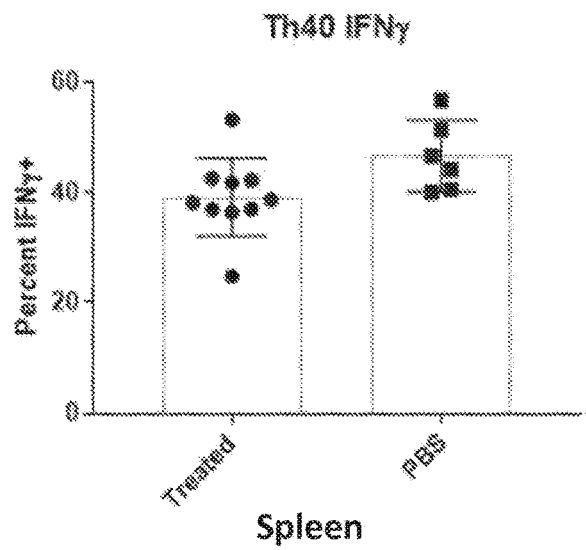
Figure 18C:
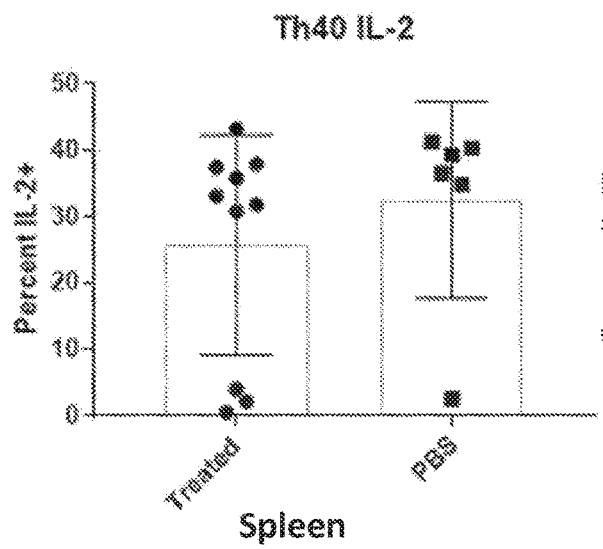
Figure 18D:
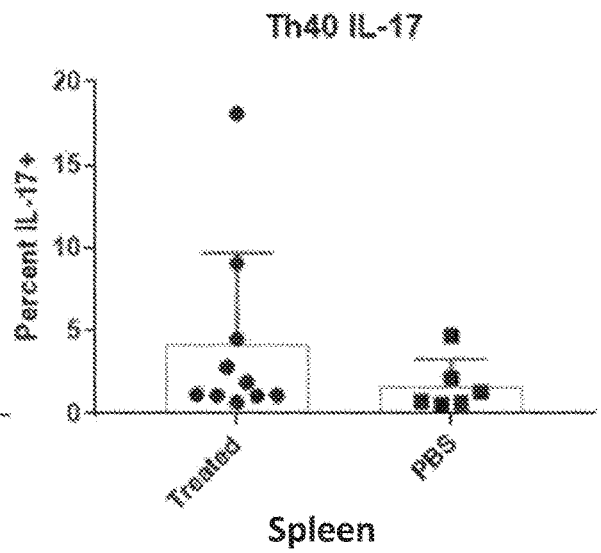
Figure 19A:
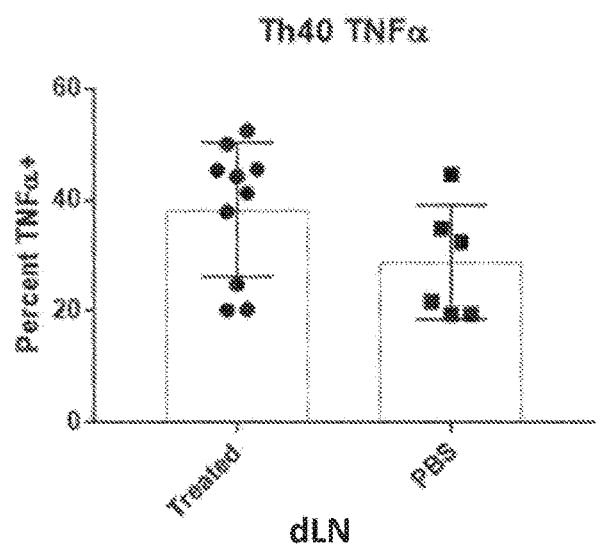
FIG. 19A, FIG. 19B, FIG. 19C and FIG. 19D are charts demonstrating the levels of TNFα, IFNγ, IL-2, and IL-17A in Th40 cells from dLN of $KGYY_6$ treated and untreated mice.
Figure 19B:
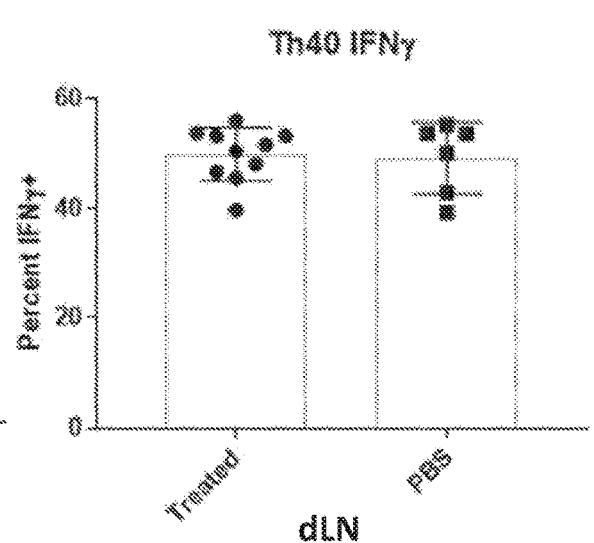
Figure 19C:
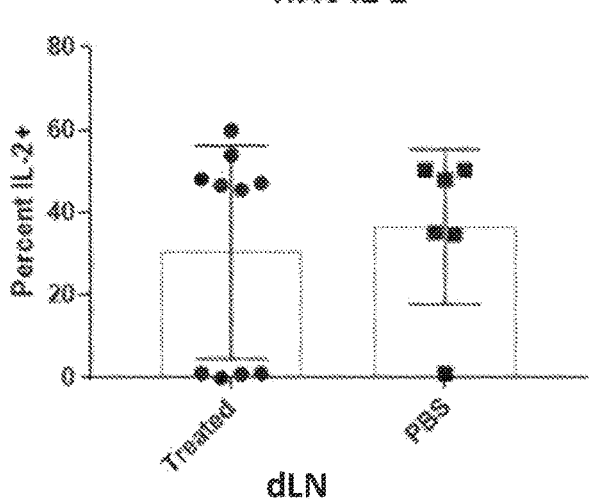
Figure 19D:
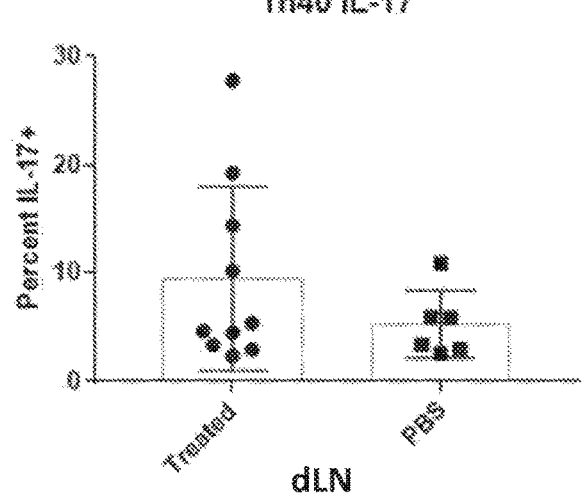
Figure 20A:
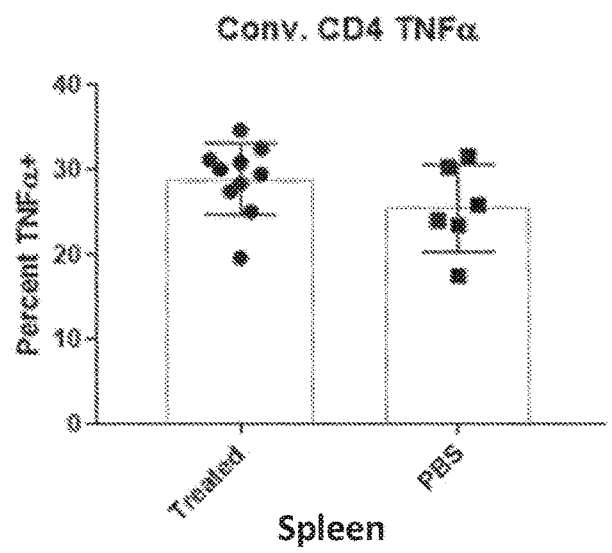
FIG. 20A, FIG. 20B, FIG. 20C and FIG. 20D are charts demonstrating the levels of TNFα, IFNγ, IL-2, and IL-17A in conventional CD4 T cells from the spleen of $KGYY_6$ treated and untreated mice.
Figure 20B:
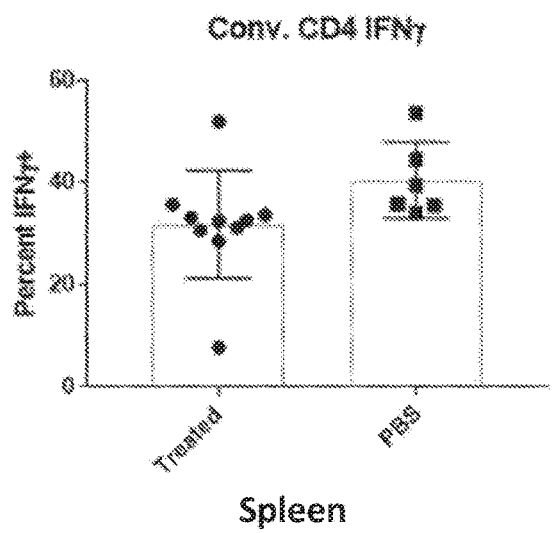
Figure 20C:
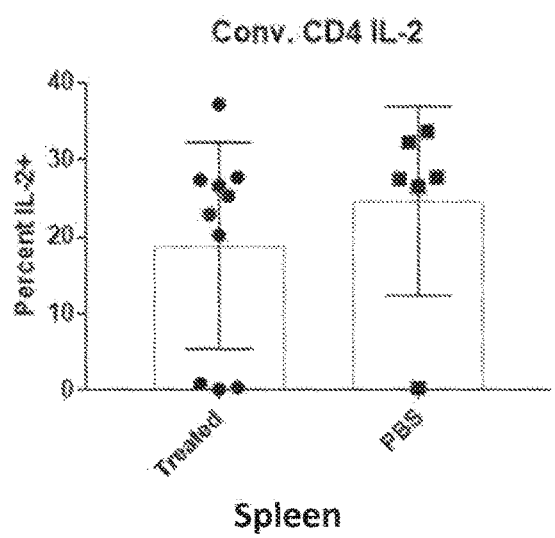
Figure 20D:
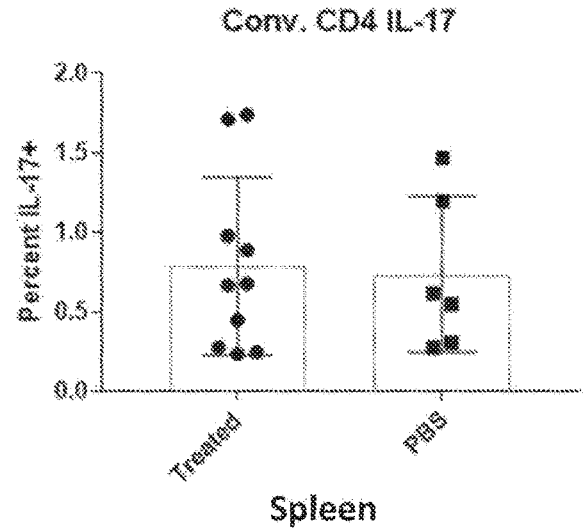
Figure 21A:
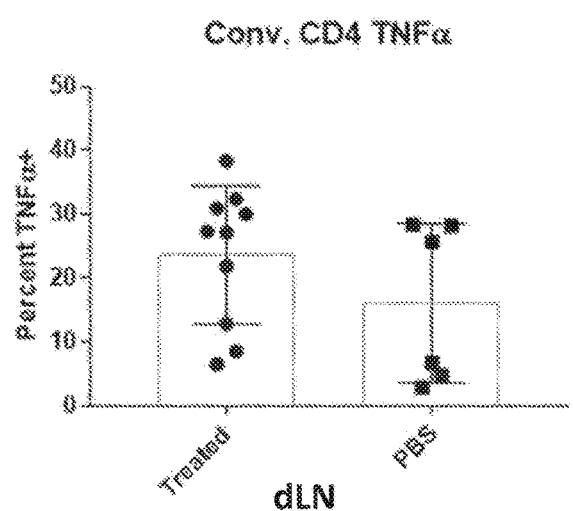
FIG. 21A, FIG. 21B, FIG. 21C and FIG. 21D are charts demonstrating the levels of TNFα, IFNγ, IL-2, and IL-17A in conventional CD4 T cells from the dLN of $KGYY_6$ treated and untreated mice.
Figure 21B:
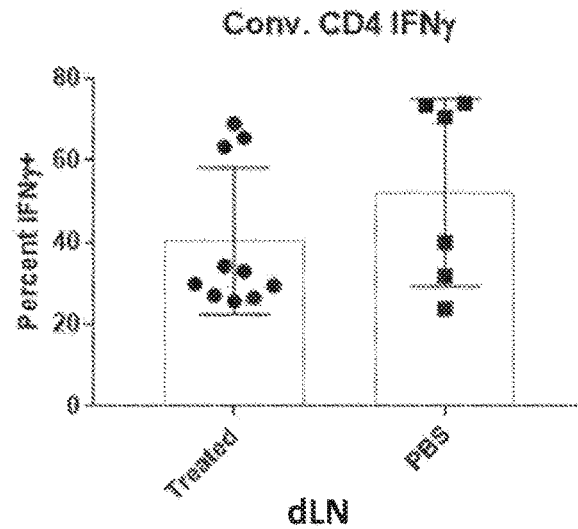
Figure 21C:
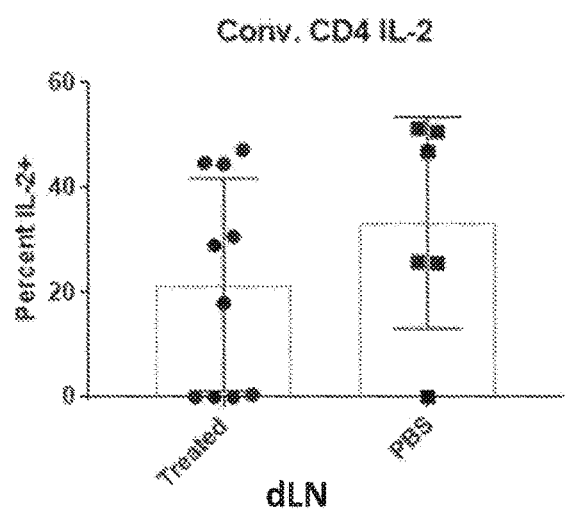
Figure 21D:
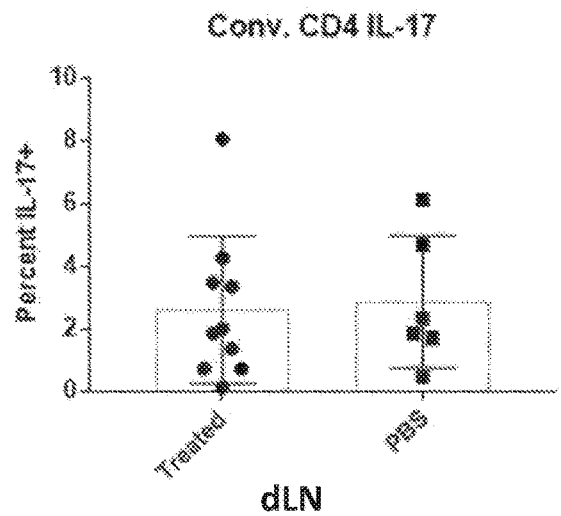
Figure 22A:
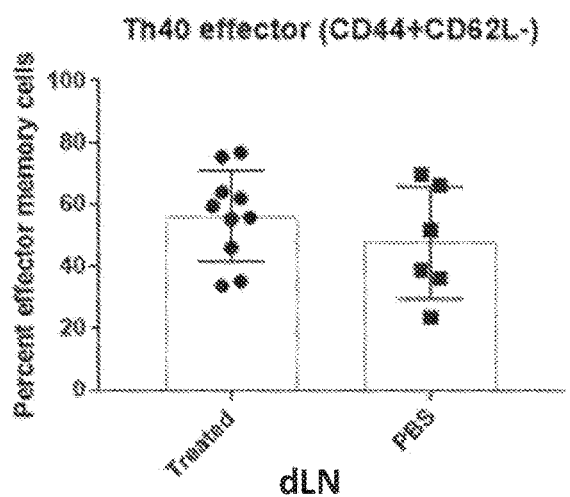
FIG. 22A, FIG. 22B, FIG. 22C and FIG. 22D are charts demonstrating the effect that $KGYY_6$ may have on memory cell levels in dLN of treated and untreated mice.
Figure 22B:
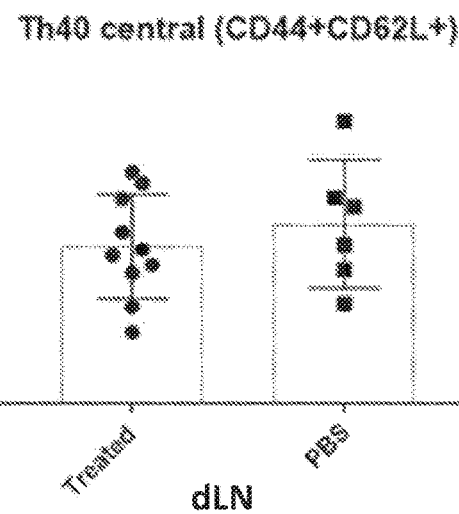
Figure 22C:
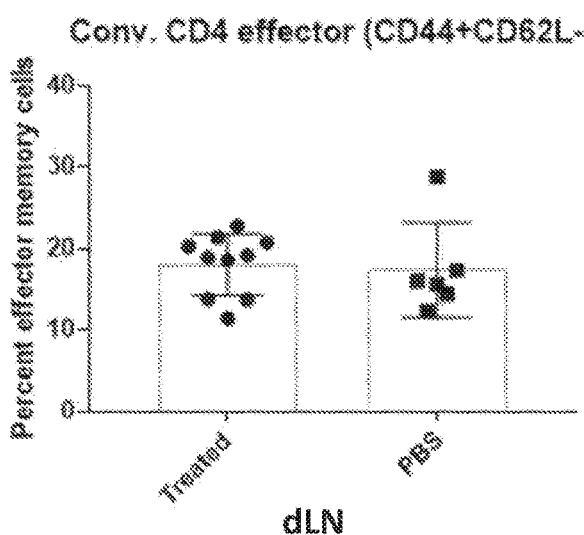
Figure 22D:
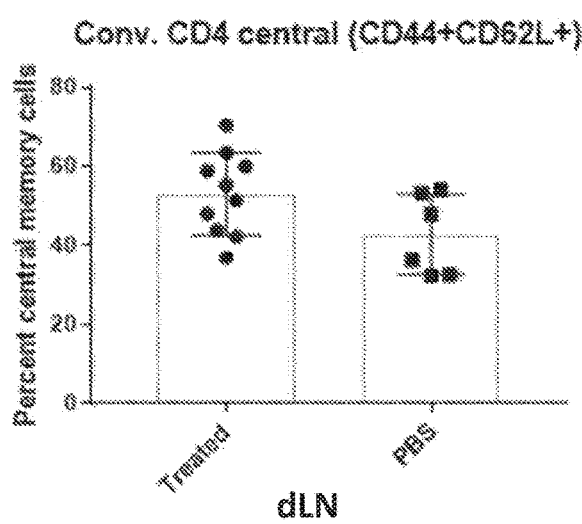
Figure 23A:
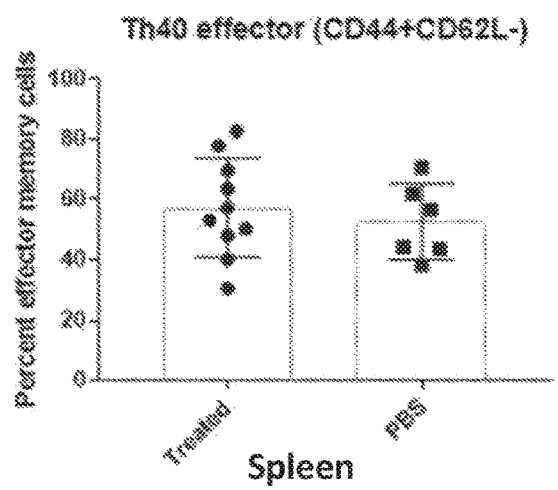
FIG. 23A, FIG. 23B, FIG. 23C and FIG. 23D are charts demonstrating the effect that $KGYY_6$ may have on memory cell levels in spleen of treated and untreated mice.
Figure 23B:
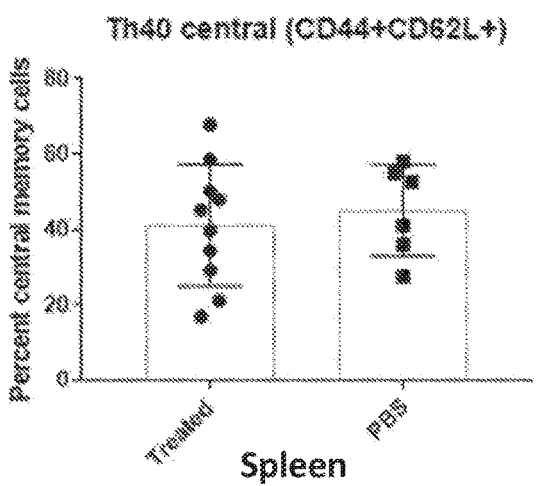
Figure 23C:
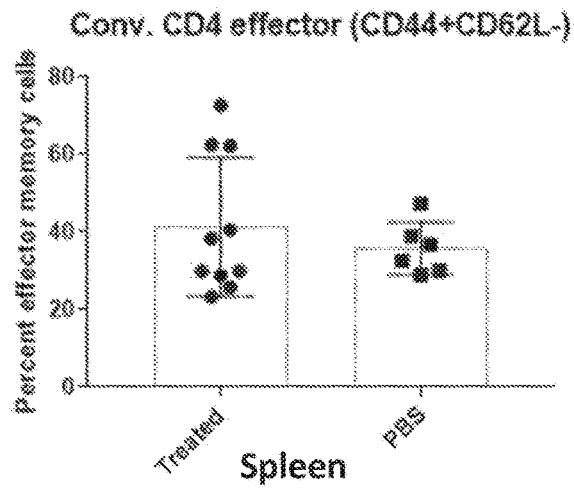
Figure 23D:
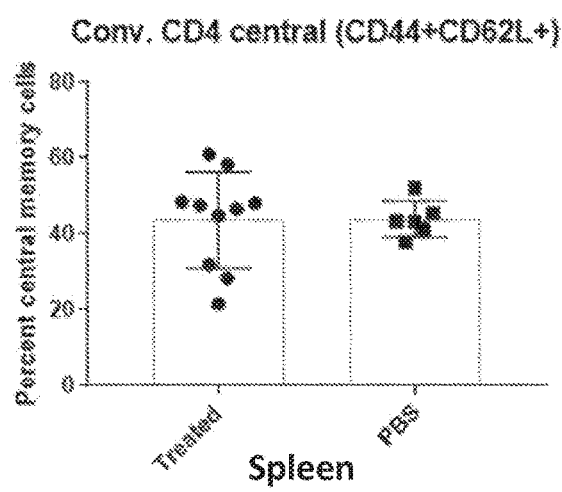

FIGS. 17A to 17D demonstrate the effect that administration of the $KGYY_6$ had on IL-10 levels in Th40 cells from the spleen and dLN of treated and untreated mice. In FIG. 17C, significance was calculated by t-test and p-values are indicated in the figure and the text.

Other cytokines, such as TNFα, IFNγ, IL-2, and IL-17A were unchanged in response to $KGYY_6$ treatment in both cell types. This is demonstrated in FIGS. 18A, 18B, 18C, and 18D, 19A, 19B, 19C, and 19D, 20A, 20B, 20C, and 20D, and 21A, 21B, 21C, and 21D. Lymphocytes from dLN or spleen were stained and gated on the Th40 or conventional CD4 T cells then intracellular levels were analyzed. FIGS. 18A-D represent the Th40 cells from spleen. FIGS. 19A-D represent the Th40 cells from dLN. FIGS. 20A-D represent conventional CD4 T cells from the spleen. FIGS. 21A-D represent conventional CD4 T cells from dLN.

Example 13

This study sought to determine whether treatment with $KGYY_6$ had any effect on memory cell levels when administered as described in Example 7 above. When examining the expression of $CD44^+CD62L^-$ (effector memory) and $CD44^+CD62L^+$ (central memory) in both spleens and dLN there was no difference in the levels of those memory phenotypes between treated and untreated Th40 or conventional CD4 T cells.

FIGS. 22A, 22B, 22C, and 22D and FIGS. 23A, 22B, 22C, and 22D demonstrate that $KGYY_6$ may not affect memory cell levels. C57BL/6 mice were EAE induced then lymphocytes were stained and gated on Th40 or conventional CD4 T cells and effector and central memory cell levels analyzed in dLN (FIGS. 22A-22D) and spleen (FIGS. 23A-D). Significance was calculated by t-test.

Example 14

To confirm that $KGYY_6$ binds to the intended target cells, peripheral blood was harvested from mononuclear cells (PBMC), dLN lymphocytes, and splenic lymphocytes from mice at 6 and 13 days out from receiving the full EAE regimen. These cells were then stained with an FITC-conjugated $KGYY_6$. The peptide stained the CD4+CD40+ cells but not the $CD40^-$ cells in PBMC, dLN, and spleen samples. This is demonstrated in FIG. 24A (left panels). When gating on memory cells (CD62L versus CD44) the peptide stained primarily effector ($CD44^+CD62L^-$) and central memory ($CD44^+CD62L^+$) cells in PBMC and spleen samples, but had a more diffuse pattern in dLN samples, as shown in the right panel in FIG. 24A.

To confirm that the KGYY$_6$ peptide binds specifically to CD40, PBMC was stained from C57BL/6 mice that have the CD154-interacting domain of CD40 knocked out (B6.CD40KO). Clearly, the peptide did not stain the B6.CD40KO cells while it readily stained both the non-induced and EAE-induced C57BL/6 mice (FIG. 24B), demonstrating the specificity of the peptide for CD40.

Figure 24A:
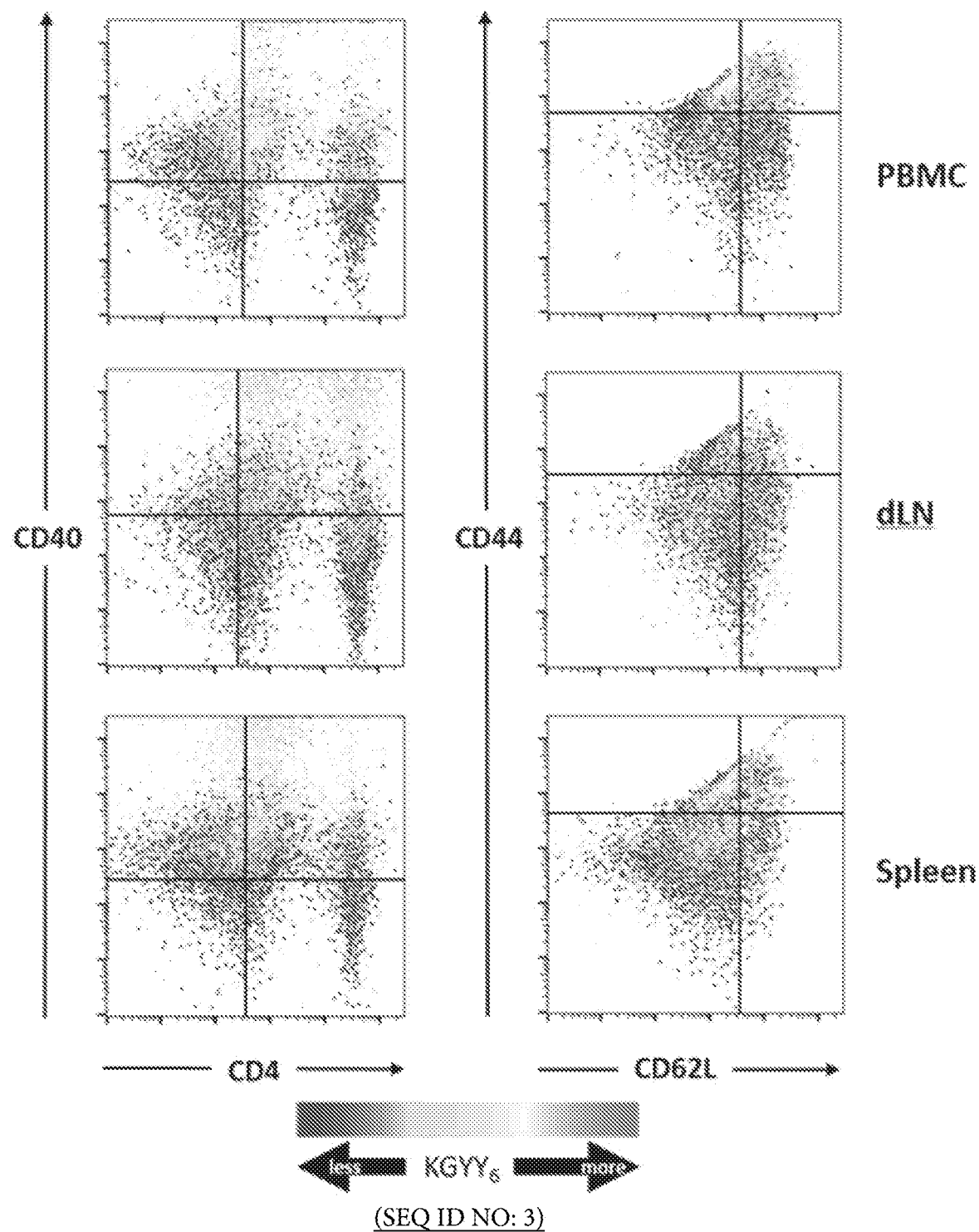
FIG. 24A is a dot plots of PBMC, dLN, and splenic lymphocytes that were harvested and then stained. Cells were gated on CD4 and CD40 (left column) or CD62L and CD44 (right column) then levels of $KGYY_6$ staining were gaged, depicted as colors according to scale below dot plots.
Figure 24B:
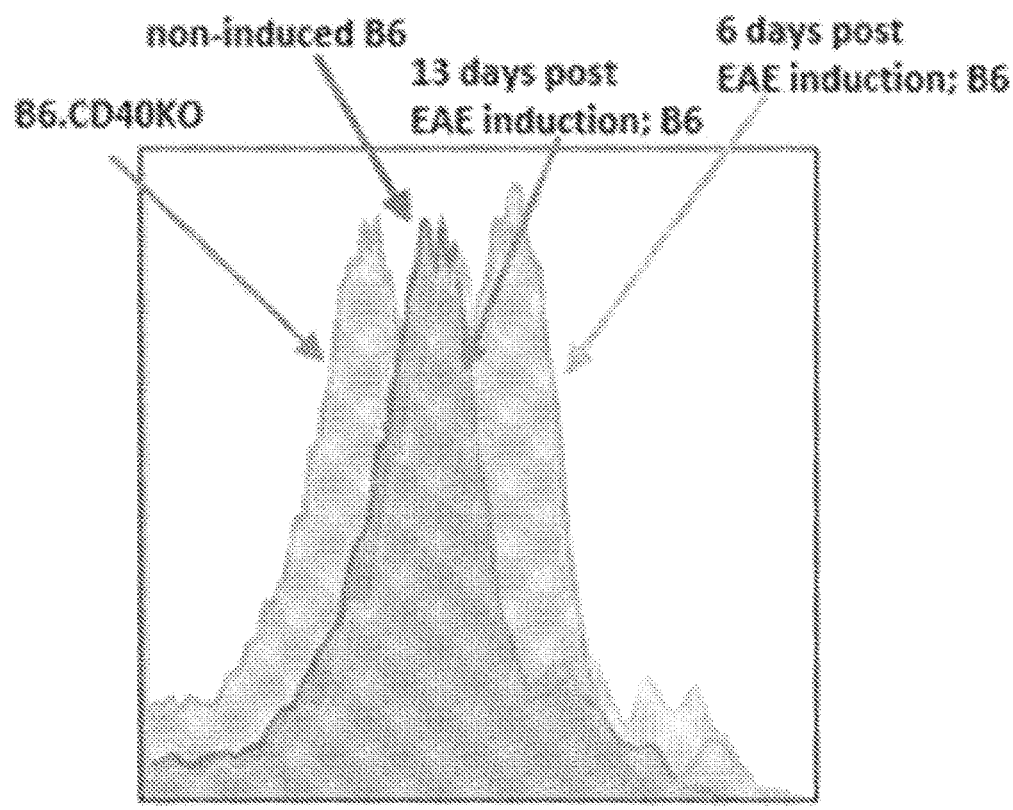
FIG. 24B is a histogram depicting $KGYY_6$ staining of B6.CD40KO, control, non-induced C57BL/6, and EAE-induced C57BL/6 mice, 6 and 13 days post induction.
Figure 25:
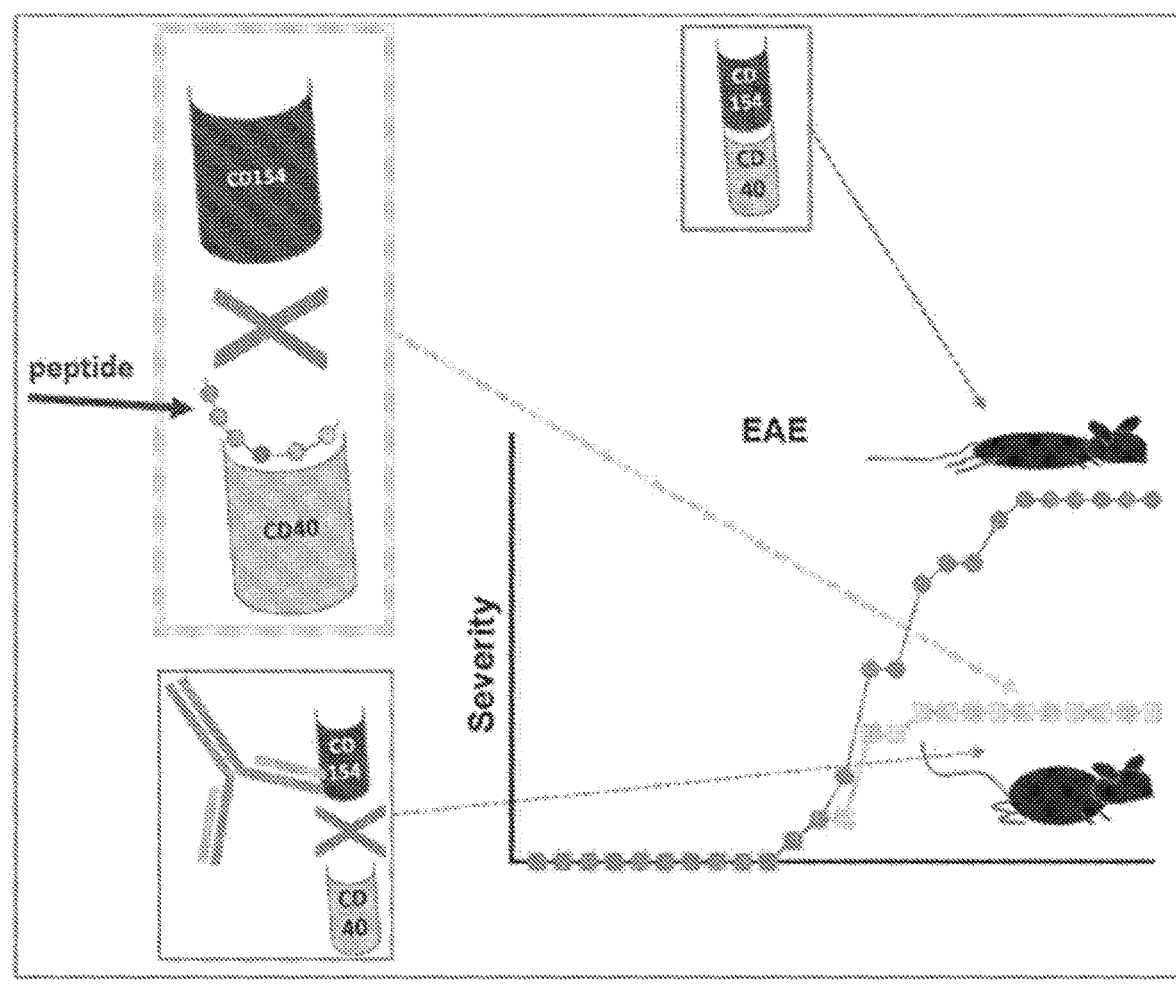
FIG. 25 is a simplified graphical representation and abstract of one implementation of the developments hereof.

FIG. 24A demonstrates that KGYY$_6$ binds Th40 and memory cells. FIG. 24A is a dot plot of PBMC, dLN, and splenic lymphocytes that were harvested and then stained. The left displays are CD4 v. CD40 with heat-mapping for KGYY$_6$. Dot plots on the right are CD62L v. CD44 with heat-mapping for KGYY$_6$. The staining shows that there is increased binding of CD4 and CD40 as in the left column. The results shown in FIG. 24A are from 6 days post EAE induction. FIG. 24B is a histogram depicting KGYY$_6$ staining of B6.CD40KO, control, non-induced C57BL/6, and EAE-induced C57BL/6 mice, 6 and 13 days post induction. Data represents two mice at day 6, three mice at day 13, all with similar results.

Example 15

Figure 26:
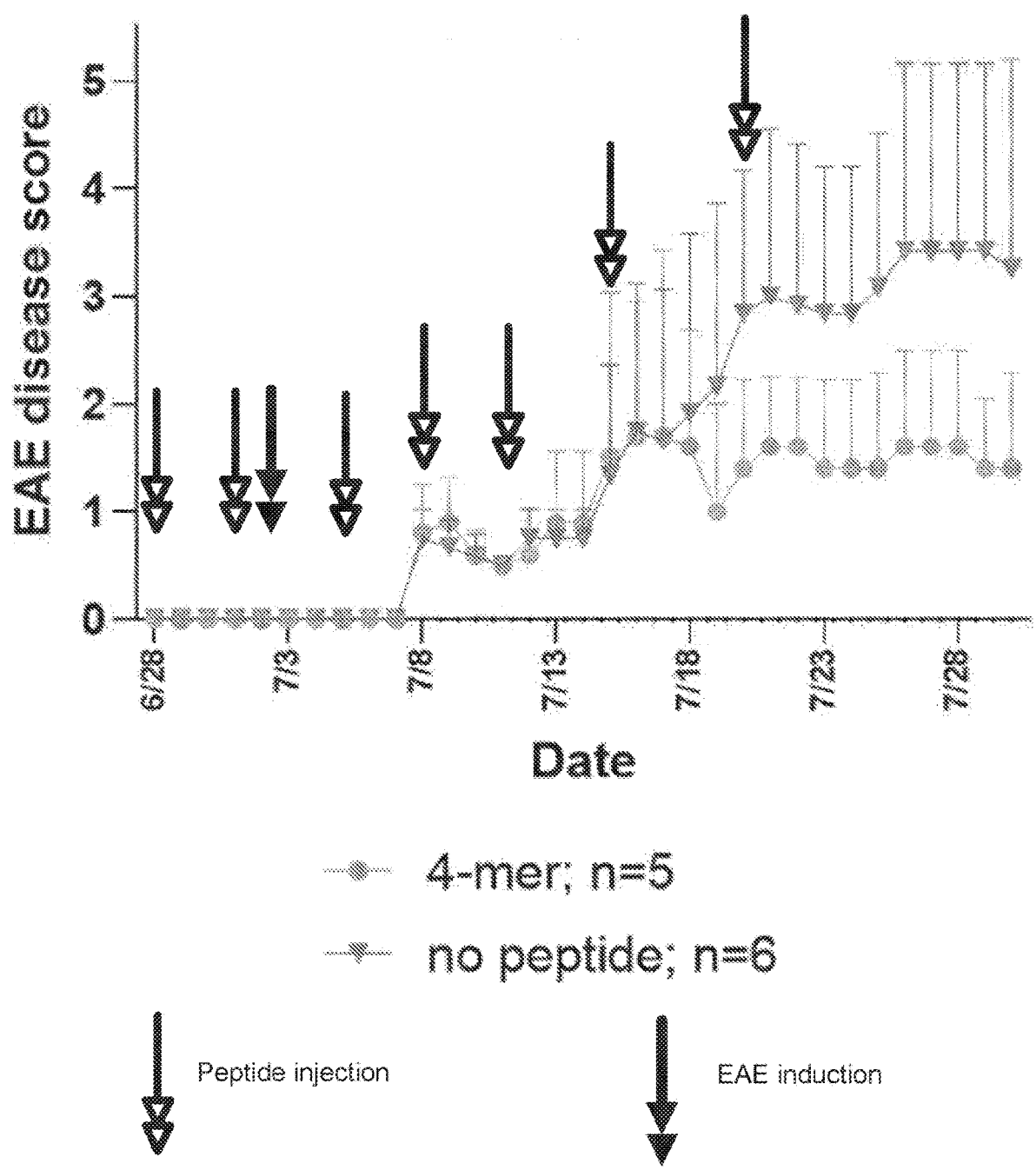
FIG. 26 is a graph of EAE disease score over time for mice treated with a 4-mer peptide.

FIG. 26 demonstrate that a KGYY (4-mer peptide) provides a desirable effect on EAE in mice when administered prior to onset and then post on-set. FIG. 26 provides support and evidence that EAE mice treated with a 4-mer (KGYY) peptide have lower EAE scores compared to untreated mice.

Example 16

Figure 27:
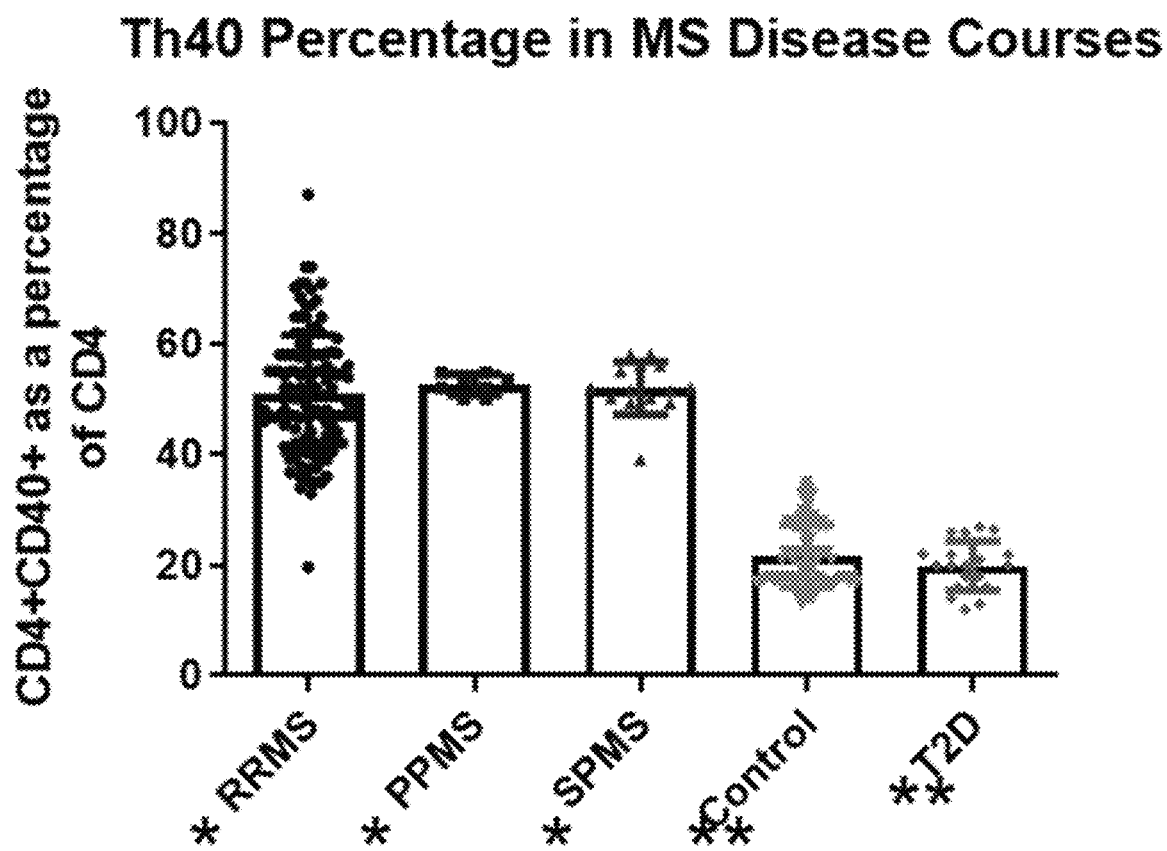
FIG. 27 is a graph of Th40 cell levels in MS.

FIG. 27 demonstrates Th40 cell levels in MS. Here, Th40 cell levels were determined from peripheral blood of Relapsing/Remitting (RRMS, n=168), RRMS, primary progressive (PPMS, n=9), secondary progressive (SPMS, n=22) and non-autoimmune control patients (n=112) Headache clinic (n=42), infectious disease (n=39). MS subjects met McDonald criteria. Average age of all MS cohorts is 41.1 and of controls is 39.7; male and female subjects are represented. Peripheral blood lymphocytes (purified) were stained with anti-CD4, anti-CD40, and anti-TCR. HLA+ antigen presenting cells and CD8+ cells were removed. Data have been collected over 6 years. Statistics were obtained using unpaired t-test and ANOVA done using Graph Pad Prism program.

Discussion

Early and ongoing treatment with disease-modifying therapy is currently the best care in relapsing remitting MS (RRMS). Such treatments can reduce the number of relapses, delay progression of disability, and limit new lesions as seen on MRI. When severe relapses occur, corticosteroids are used to manage and reduce the inflammation in the CNS. Many of the current treatments for MS often have the side effect of broadly suppressing the immune system. While that may decrease disease symptoms, it also leads to an increased susceptibility to opportunistic infections. Therefore, the search for treatments that have a more targeted effect on the actual culprit immune cells is ongoing.

Prior studies have demonstrated that Th40 cells drive a more severe form of EAE than conventional CD4 T cells do. (Vaitaitis, G. M., et al., PLoS ONE 12:2, 2017). Th40 cells express the alternative costimulatory molecule CD40 which is also expressed by other immune cells and is known to be a major target in autoimmune diseases. (Kansas, G. S., APMIS, 100(4):287, 1992; Baker, R. L., et al., J. of Autoimmunity, 31:385, 2008).

In the set of studies described herein, a 6-mer peptide that spans the core region of the domain in the CD154 protein that interacts with CD40 to affect CD40 signals during the EAE disease process was used. Clearly, administration of the peptide ameliorated the symptoms whether pretreated then boosted or just treated at the first sign of symptoms. Pretreatment followed by boosts worked better than just treating at signs of symptoms. Obviously, by treating at the first signs of symptoms, is approximating human disease where it is desirable to treat only when disease symptoms onset rather than continually administering therapy. The limitation with the EAE studies is that the mice cannot communicate when they start feeling unwell, so therefore each mouse subject must be gaged for onset of EAE disease by visual clues such as a limp tail or wobbly gait. In human disease, an MS patient who is experiencing a relapse may very well be aware of telltale signs much earlier than the appearance of actual disability. Peptide therapy could therefore commence at much earlier stages, possibly having a greater impact. In the EAE experiments here, there was certainly a significantly better outcome if the peptide boosts were administered earlier, before any visible signs of disease. It would also be possible to keep those with diagnosed MS who are in remission in treatment with periodic peptide doses and then increase the dosing frequency if the patient reports early signs of a relapse.

Interestingly, treating EAE mice with KGYY$_6$ induced a significant increase in CD69 expression in dLN and spleen CD4 T cells (Th40 and conventional CD4 T cells), which recently was shown to prolong tissue retention of T cell. KGYY$_6$ treatment also induced an increase in IL-10 expression in conventional CD4 T cells from dLN samples. Therefore, it is possible that the T cells are retained longer in dLN and spleen, possibly experiencing anti-inflammatory signals by way of IL-10, causing them to miss the window of opportunity to cause maximal damage in concert with other immune cells in the CNS. KGYY$_6$ did not cause a decrease in the Th40 cell population, rather it appears that it affected the timing of trafficking and possibly the sub-phenotype of the culprit cells. KGYY$_6$ appears to directly target the culprit cells as we could demonstrate binding specifically to Th40 cells from EAE induced mice.

The present data support a more targeted effect on the culprit cells in EAE in that the peptide does not eliminate or depress all T cells or even all Th40 cells. Therefore, it is likely that the KGYY$_6$ peptide would not be generally immunosuppressive. If so, KGYY$_6$ therapy would be advantageous compared to many current MS drug therapies that often immune suppress the patients. Therefore, one implementation of the current developments may also include the administration of the peptide with a known drug approved to treat MS.

The above discussion is directed to various implementations of the developments hereof. Although one or more of these implementations may be preferred, the implementations disclosed should not be interpreted, or otherwise used, as or for limiting the scope of the disclosure, including the claims. In addition, one skilled in the art will understand that the above description has broad applications, and the discussion of any implementation is meant only to exemplary of that implementation and is not intended to intimate that the scope of the disclosure, including the claims, is limited to that implementation.

We claim:

1. A method for reducing symptoms of multiple sclerosis in a subject comprising administering to the subject a therapeutic amount of a 6 amino acid long peptide having the amino acid sequence of SEQ ID NO: 28.

2. The method of claim 1, wherein the therapeutic amount of the peptide is administered by a delivery method comprising intramuscular (IM) delivery, intravenous (IV) delivery, subcutaneous (SC) delivery, oral delivery, gavage delivery, emollient/skin delivery, intrathecal delivery, intranasal delivery, sublingual delivery, intracerebral delivery, or transdermal patch.

3. The method of claim 1, further comprising using an extended delivery method selected from one or more of an implantable device, a hydrophilic polymer formulation, a permeable polymeric membrane, injectable gel implants, solvent extraction system, phase inversion system, thermosensitive gels, pH dependent in situ gels, microparticles, microspheres, nanoparticles, nanospheres, bio-degradable implants, and photoactivated depot.

4. The method of claim 1, further comprising administering a composition selected from one or more of Aubagio® (teriflunomide), Betaseron (interferon-b (type 1)), Avonex® (interferon-b-1 b), Rebif® (interferon-beta-1a), Copaxone® (glatiramer acetate), Tysabri® (natalizumab), Novantrone® (mitoxantrone), Gilenya® (fingolimod), Tecfidera® (dimethyl fumarate), Rituxan® (rituximab), Ocrevus® (ocrelizumab) and Lemtrada® (alemtuzumab).

5. A method for alleviating symptoms in primary progressive MS (PPMS) or secondary progressive MS (SPMS) in a subject comprising administering a 6 amino acid long peptide having the amino acid sequence of SEQ ID NO: 28 to the subject.

6. The method of claim 5, further comprising administering a composition selected from one or more of Aubagio® (teriflunomide), Betaseron® (interferon-b (type 1)), Avonex® (interferon-b-1 b), Rebif® (interferon-beta-1a), Copaxone® (glatiramer acetate), Tysabri® (natalizumab), Novantrone® (mitoxantrone), Gilenya® (fingolimod), Tecfidera® (dimethyl fumarate), Rituxan® (rituximab), Ocrevus® (ocrelizumab) and Lemtrada® (alemtuzumab).

7. The method of claim 5, wherein the peptide is configured to have one or more modifications selected from: pegylation, glycosylation, acetylation, amidation; PASylation with Pro, Ala and Ser (PAS) sequences, or including polyglycerols, polyoxazolines, poly(amino acids), polyacrylamides, polyvinylpyrrolidones, and polyzwitterions; synthetization; and being configured as a salt.

8. The method of claim 5, further comprising:
slowing or abating the growth of number of lesions;
slowing or abating the size of lesions; and/or
prolonging tissue retention of T cells.

* * * * *